United States Patent
Fan

(10) Patent No.: US 8,076,063 B2
(45) Date of Patent: Dec. 13, 2011

(54) MULTIPLEXED METHYLATION DETECTION METHODS

(75) Inventor: Jian-Bing Fan, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1010 days.

(21) Appl. No.: 10/537,204

(22) PCT Filed: Dec. 3, 2003

(86) PCT No.: PCT/US03/38582

§ 371 (c)(1),
(2), (4) Date: Feb. 6, 2007

(87) PCT Pub. No.: WO2004/051224

PCT Pub. Date: Jun. 17, 2004

(65) Prior Publication Data

US 2007/0269801 A1    Nov. 22, 2007

Related U.S. Application Data

(63) Continuation-in-part of application No. 10/309,803, filed on Dec. 3, 2002.

(51) Int. Cl.
- *C12Q 1/68* (2006.01)
- *C12P 19/34* (2006.01)
- *C07H 21/02* (2006.01)
- *C07H 21/04* (2006.01)
- *C07H 21/00* (2006.01)

(52) U.S. Cl. ......... 435/6; 435/91.1; 435/91.2; 536/23.1; 536/24.3; 536/24.33; 536/25.3

(58) Field of Classification Search ............. 435/6, 91.1, 435/91.2, 183; 436/94, 501; 536/23.1, 24.3, 536/24.33, 25.3
See application file for complete search history.

(56) References Cited

U.S. PATENT DOCUMENTS

| | | |
|---|---|---|
| 4,200,110 A | 4/1980 | Peterson et al. |
| 4,499,052 A | 2/1985 | Fulwyler |
| 4,563,419 A | 1/1986 | Ranki et al. |
| 4,582,789 A | 4/1986 | Sheldon |
| 4,682,895 A | 7/1987 | Costello |
| 4,683,195 A | 7/1987 | Mullis et al. |
| 4,683,202 A | 7/1987 | Mullis |
| 4,687,732 A | 8/1987 | Ward |
| 4,751,177 A | 6/1988 | Stabinsky |
| 4,785,814 A | 11/1988 | Kane |
| 4,822,746 A | 4/1989 | Walt |
| 4,824,789 A | 4/1989 | Yafuso et al. |
| 4,876,187 A | 10/1989 | Duck et al. |
| 4,882,269 A | 11/1989 | Schneider et al. |
| 4,883,750 A | 11/1989 | Whiteley et al. |
| 4,921,805 A | 5/1990 | Gebeyehu et al. |
| 4,988,617 A | 1/1991 | Landegren et al. |
| 4,999,306 A | 3/1991 | Yafuso et al. |
| 5,002,867 A | 3/1991 | Macevicz |
| 5,011,769 A | 4/1991 | Duck et al. |
| 5,028,545 A | 7/1991 | Soini |
| 5,043,272 A | 8/1991 | Hartley |
| 5,104,791 A | 4/1992 | Abbott |
| 5,105,305 A | 4/1992 | Betzig et al. |
| 5,114,864 A | 5/1992 | Walt |
| 5,130,238 A | 7/1992 | Malek |
| 5,132,242 A | 7/1992 | Cheung |
| 5,143,853 A | 9/1992 | Walt |
| 5,175,082 A | 12/1992 | Jeffreys |
| 5,185,243 A | 2/1993 | Ullman et al. |
| 5,194,300 A | 3/1993 | Cheung |
| 5,202,231 A | 4/1993 | Drmanac et al. |
| 5,232,829 A | 8/1993 | Longiaru et al. |
| 5,242,794 A | 9/1993 | Whiteley et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt et al. |
| 5,298,741 A | 3/1994 | Walt et al. |
| 5,302,509 A | 4/1994 | Cheeseman |
| 5,314,809 A | 5/1994 | Erlich et al. |
| 5,320,814 A | 6/1994 | Walt et al. |
| 5,357,590 A | 10/1994 | Auracher |
| 5,380,489 A | 1/1995 | Sutton et al. |
| 5,387,505 A | 2/1995 | Wu et al. |
| 5,399,491 A | 3/1995 | Kacian et al. |
| 5,403,711 A | 4/1995 | Walder et al. |
| 5,409,818 A | 4/1995 | Davey et al. |
| 5,427,930 A | 6/1995 | Birkenmeyer et al. |
| 5,435,724 A | 7/1995 | Goodman et al. |
| 5,445,934 A | 8/1995 | Fodor et al. |
| 5,455,166 A | 10/1995 | Walker |
| 5,474,895 A | 12/1995 | Ishii et al. |

(Continued)

FOREIGN PATENT DOCUMENTS

EP        0 139 489        5/1985

(Continued)

OTHER PUBLICATIONS

Document for Hpa II from NEB. Printed on Sep. 8, 2010.* Documents for exonuclease I and Msp I from NEB. Printed on Sep. 9, 2010.*
U.S. Appl. No. 09/189,543, filed Mar. 1, 2001, Chee.
U.S. Appl. No. 09/500,555, filed Feb. 9, 2000, Stuelpnagel.
U.S. Appl. No. 09/606,369, filed Jun. 28, 2000, Stuelpnagel.
Abramson et al., "Nucleic acid amplification technologies," *Current Opinion in Biotechnology* 4:41-47 (1993).
Akama et al., "Restriction landmark genomic scanning (RLGS-M)-based genome-wide scanning of mouse liver tumors for alterations in DNA methylation status," *Cancer Res.* 57:3294-3299 (1997).
Baner et al., "Signal amplification of padlock probes by rolling circle replication," *Nuc. Acids Res.* 26:5073-5078 (1998).
Barany, "Mutation detection and single-molecule counting using isothermal rolling-circle amplification," *Proc. Natl. Acad. Sci. USA* 88:189-193 (1991).
Baylin and Herman, "DNA hypermethylation in tumorigenesis: epigenetics joins genetics." *Trends Genet.* 16:168-174 (2000).
Bestor, "Gene silencing. Methylation meets acetylation," *Nature* 393:311-312 (1998).
Corder et al., "Gene dose of apolipoprotein E type 4 allele and the risk of alzheimer's disease in late onset families," *Science* 261:921-923(1993).
Costello et al., "Aberrant CpG-island methylation has non-random and tumour-type specific patterns," *Nat. Genet.* 24:132-138 (2000).
Dragich et al., "Rett syndrome: a surprising result of mutation in MECP2," *Hum. Mol. Genet.* 9:2365-2375 (2000).

(Continued)

*Primary Examiner* — Frank W Lu
(74) *Attorney, Agent, or Firm* — Jones Day

(57) ABSTRACT

The present invention is directed to sensitive and accurate multiplexed assays for target analyte detection and detection of methylation in nucleic acid samples.

6 Claims, 14 Drawing Sheets

U.S. PATENT DOCUMENTS

| | | | |
|---|---|---|---|
| 5,481,629 A | 1/1996 | Tabuchi |
| 5,489,507 A | 2/1996 | Chehab |
| 5,494,798 A | 2/1996 | Gerdt et al. |
| 5,494,810 A | 2/1996 | Barany et al. |
| 5,496,997 A | 3/1996 | Pope |
| 5,503,980 A | 4/1996 | Cantor |
| 5,512,490 A | 4/1996 | Walt et al. |
| H1531 H | 5/1996 | Blumentals |
| 5,516,635 A | 5/1996 | Ekins et al. |
| 5,521,065 A | 5/1996 | Whiteley et al. |
| 5,525,464 A | 6/1996 | Drmanac et al. |
| 5,541,311 A | 7/1996 | Dahlberg et al. |
| 5,545,531 A | 8/1996 | Rava et al. |
| 5,554,516 A | 9/1996 | Kacian et al. |
| 5,565,324 A | 10/1996 | Still et al. |
| 5,567,587 A | 10/1996 | Kohne |
| 5,571,639 A | 11/1996 | Hubbell et al. |
| 5,573,907 A | 11/1996 | Carrino et al. |
| 5,573,909 A | 11/1996 | Singer et al. |
| 5,575,849 A | 11/1996 | Honda et al. |
| 5,578,832 A | 11/1996 | Trulson et al. |
| 5,593,840 A | 1/1997 | Bhatnagar et al. |
| 5,595,890 A | 1/1997 | Newton et al. |
| 5,601,978 A | 2/1997 | Burczak et al. |
| 5,604,097 A | 2/1997 | Brennar |
| 5,614,402 A | 3/1997 | Dahlberg et al. |
| 5,632,957 A | 5/1997 | Heller et al. |
| 5,633,972 A | 5/1997 | Walt et al. |
| 5,639,603 A | 6/1997 | Dower et al. |
| 5,656,241 A | 8/1997 | Seifert et al. |
| 5,660,988 A | 8/1997 | Duck et al. |
| 5,679,524 A | 10/1997 | Nikiforov et al. |
| 5,681,697 A | 10/1997 | Urdea et al. |
| 5,690,894 A | 11/1997 | Pinkel et al. |
| 5,695,940 A | 12/1997 | Drmanac et al. |
| 5,705,365 A | 1/1998 | Ryder et al. |
| 5,710,029 A | 1/1998 | Ryder et al. |
| 5,733,729 A | 3/1998 | Lipshutz et al. |
| 5,744,305 A | 4/1998 | Fodor et al. |
| 5,763,175 A | 6/1998 | Brenner |
| 5,780,231 A | 7/1998 | Brenner |
| 5,786,146 A | 7/1998 | Herman et al. |
| 5,792,607 A | 8/1998 | Backman et al. |
| 5,795,714 A | 8/1998 | Cantor et al. |
| 5,795,716 A | 8/1998 | Chee et al. |
| 5,800,992 A | 9/1998 | Fodor et al. |
| 5,804,376 A | 9/1998 | Braxton et al. |
| 5,807,522 A | 9/1998 | Brown et al. |
| 5,814,524 A | 9/1998 | Walt |
| 5,830,655 A | 11/1998 | Monforte et al. |
| 5,830,711 A | 11/1998 | Barany et al. |
| 5,834,758 A | 11/1998 | Trulson et al. |
| 5,840,256 A | 11/1998 | Demers et al. |
| 5,843,669 A | 12/1998 | Kaiser et al. |
| 5,846,710 A | 12/1998 | Bajaj |
| 5,846,717 A | 12/1998 | Brow et al. |
| 5,846,719 A | 12/1998 | Brenner |
| 5,849,544 A | 12/1998 | Harris |
| 5,853,989 A | 12/1998 | Jeffreys et al. |
| 5,854,033 A | 12/1998 | Lizardi |
| 5,854,684 A | 12/1998 | Stabile et al. |
| 5,856,083 A | 1/1999 | Chelsky et al. |
| 5,858,732 A | 1/1999 | Solomon et al. |
| 5,863,708 A | 1/1999 | Zanzucchi et al. |
| 5,866,321 A | 2/1999 | Matsue et al. |
| 5,869,252 A | 2/1999 | Bouma et al. |
| 5,871,917 A | 2/1999 | Duffy |
| 5,871,928 A | 2/1999 | Fodor et al. |
| 5,874,219 A | 2/1999 | Rava et al. |
| 5,876,924 A | 3/1999 | Zhang et al. |
| 5,888,723 A | 3/1999 | Sutton et al. |
| 5,888,778 A | 3/1999 | Shuber |
| 5,888,779 A | 3/1999 | Kacian et al. |
| 5,888,819 A | 3/1999 | Goelet et al. |
| 5,900,481 A | 5/1999 | Lough et al. |
| 5,935,793 A | 8/1999 | Wong et al. |
| 5,942,391 A | 8/1999 | Zhang et al. |
| 5,952,174 A | 9/1999 | Nikiforov et al. |
| 5,974,164 A | 10/1999 | Chee et al. |
| 5,976,797 A | 11/1999 | Mitsuhashi |
| 5,994,066 A | 11/1999 | Bergeron et al. |
| 5,998,175 A | 12/1999 | Akhavan-Tafti |
| 6,001,564 A | 12/1999 | Bergeron et al. |
| 6,013,440 A | 1/2000 | Lipshutz et al. |
| 6,013,456 A | 1/2000 | Akhavan-Tafti |
| 6,017,738 A | 1/2000 | Morris et al. |
| 6,023,540 A | 2/2000 | Walt et al. |
| 6,025,601 A | 2/2000 | Trulson et al. |
| 6,027,889 A | 2/2000 | Barany et al. |
| 6,040,138 A | 3/2000 | Lockhart et al. |
| 6,045,996 A | 4/2000 | Cronin et al. |
| 6,051,380 A | 4/2000 | Sosnowski et al. |
| 6,054,564 A | 4/2000 | Barany et al. |
| 6,060,245 A | 5/2000 | Sorge et al. |
| 6,066,454 A | 5/2000 | Lipshutz et al. |
| 6,083,753 A | 7/2000 | Kelly et al. |
| 6,083,763 A | 7/2000 | Balch |
| 6,090,558 A | 7/2000 | Butler et al. |
| 6,096,496 A | 8/2000 | Frankel |
| 6,110,678 A | 8/2000 | Weisburg et al. |
| 6,124,102 A | 9/2000 | Fodor et al. |
| 6,143,495 A | 11/2000 | Lizardi et al. |
| 6,172,218 B1 | 1/2001 | Brenner et al. |
| 6,183,960 B1 | 2/2001 | Lizardi |
| 6,185,561 B1 | 2/2001 | Balaban et al. |
| 6,188,783 B1 | 2/2001 | Balaban et al. |
| 6,197,506 B1 | 3/2001 | Fodor et al. |
| 6,200,737 B1 | 3/2001 | Walt et al. |
| 6,200,756 B1 | 3/2001 | Herman et al. |
| 6,210,884 B1 | 4/2001 | Lizardi |
| 6,214,556 B1 | 4/2001 | Olek et al. |
| 6,221,603 B1 | 4/2001 | Mahtani |
| 6,225,064 B1 | 5/2001 | Uematsu et al. |
| 6,225,625 B1 | 5/2001 | Pirrung et al. |
| 6,229,911 B1 | 5/2001 | Balaban et al. |
| 6,248,539 B1 | 6/2001 | Ghadiri et al. |
| 6,251,594 B1 | 6/2001 | Gonzalgo et al. |
| 6,251,639 B1 | 6/2001 | Kurn |
| 6,261,776 B1 | 7/2001 | Pirrung et al. |
| 6,265,171 B1 | 7/2001 | Herman et al. |
| 6,266,459 B1 | 7/2001 | Walt et al. |
| 6,268,148 B1 | 7/2001 | Barany et al. |
| 6,274,323 B1 | 8/2001 | Bruchez et al. |
| 6,280,935 B1 | 8/2001 | Macevicz |
| 6,280,949 B1 | 8/2001 | Lizardi |
| 6,284,465 B1 | 9/2001 | Wolber |
| 6,291,166 B1 | 9/2001 | Gerdes et al. |
| 6,291,183 B1 | 9/2001 | Pirrung et al. |
| 6,300,071 B1 | 10/2001 | Vuylsteke et al. |
| 6,306,643 B1 | 10/2001 | Gentalen et al. |
| 6,308,170 B1 | 10/2001 | Balaban et al. |
| 6,309,822 B1 | 10/2001 | Fodor et al. |
| 6,316,229 B1 | 11/2001 | Lizardi et al. |
| 6,327,410 B1 | 12/2001 | Walt et al. |
| 6,329,150 B1 | 12/2001 | Lizardi |
| 6,331,393 B1 | 12/2001 | Laird et al. |
| 6,335,165 B1 | 1/2002 | Navot et al. |
| 6,342,389 B1 | 1/2002 | Cubicciotti |
| 6,346,413 B1 | 2/2002 | Fodor et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,399,365 B2 | 6/2002 | Besemer et al. |
| 6,403,320 B1 | 6/2002 | Read et al. |
| 6,416,952 B1 | 7/2002 | Pirrung et al. |
| 6,429,027 B1 | 8/2002 | Chee et al. |
| 6,440,667 B1 | 8/2002 | Fodor et al. |
| 6,451,536 B1 | 9/2002 | Fodor et al. |
| 6,491,871 B1 | 12/2002 | Fodor et al. |
| 6,511,810 B2 | 1/2003 | Bi et al. |
| 6,534,293 B1 | 3/2003 | Barany et al. |
| 6,544,732 B1 | 4/2003 | Chee et al. |
| 6,544,739 B1 | 4/2003 | Fodor et al. |
| 6,576,424 B2 | 6/2003 | Fodor et al. |
| 6,604,902 B2 | 8/2003 | Norris et al. |
| 6,605,432 B1 | 8/2003 | Huang |
| 6,610,482 B1 | 8/2003 | Fodor et al. |

| | | | |
|---|---|---|---|
| 6,618,679 B2 | 9/2003 | Loehrlein et al. | |
| 6,627,402 B2 | 9/2003 | Wallace | |
| 6,646,243 B2 | 11/2003 | Pirrung et al. | |
| 6,812,005 B2 | 11/2004 | Fan et al. | |
| 6,858,394 B1 | 2/2005 | Chee et al. | |
| 6,942,968 B1 | 9/2005 | Dickinson et al. | |
| 7,033,754 B2 | 4/2006 | Chee et al. | |
| 7,060,431 B2 | 6/2006 | Chee et al. | |
| 7,115,884 B1 | 10/2006 | Walt et al. | |
| 7,510,841 B2 | 3/2009 | Stuelpnagel et al. | |
| 7,582,420 B2 | 9/2009 | Oliphant et al. | |
| 7,612,020 B2 | 11/2009 | Stuelpnagel et al. | |
| 2001/0029049 A1 | 10/2001 | Walt et al. | |
| 2002/0006617 A1 | 1/2002 | Fan et al. | |
| 2002/0039728 A1 | 4/2002 | Kain | |
| 2002/0051971 A1 | 5/2002 | Stuelpnagel | |
| 2002/0064779 A1 | 5/2002 | Landegren | |
| 2002/0132241 A1 | 9/2002 | Fan et al. | |
| 2002/0137086 A1 | 9/2002 | Olek et al. | |
| 2002/0150921 A1 | 10/2002 | Barany et al. | |
| 2002/0168645 A1 | 11/2002 | Taylor | |
| 2002/0177141 A1 | 11/2002 | Chee et al. | |
| 2003/0027126 A1 | 2/2003 | Walt | |
| 2003/0036064 A1 | 2/2003 | Stuelpnagel et al. | |
| 2003/0082600 A1 | 5/2003 | Olek et al. | |
| 2003/0108900 A1 | 6/2003 | Oliphant et al. | |
| 2003/0119025 A1 | 6/2003 | Olek et al. | |
| 2003/0122612 A1 | 7/2003 | Kawai et al. | |
| 2003/0129620 A1 | 7/2003 | Olek et al. | |
| 2003/0162194 A1 | 8/2003 | Olek et al. | |
| 2003/0170684 A1 | 9/2003 | Fan | |
| 2003/0211489 A1 | 11/2003 | Shen et al. | |
| 2004/0023230 A1 | 2/2004 | Olek et al. | |
| 2004/0072197 A1 | 4/2004 | Jones et al. | |
| 2004/0101835 A1 | 6/2004 | Willis et al. | |
| 2004/0137473 A1 | 7/2004 | Wigler et al. | |
| 2004/0137498 A1 | 7/2004 | Fan et al. | |
| 2004/0234960 A1 | 11/2004 | Olek et al. | |
| 2004/0248090 A1 | 12/2004 | Olek et al. | |
| 2004/0259100 A1 | 12/2004 | Gunderson et al. | |
| 2004/0265814 A1 | 12/2004 | Distler et al. | |
| 2005/0053937 A1 | 3/2005 | Berlin | |
| 2006/0008824 A1 | 1/2006 | Ronaghi et al. | |
| 2006/0275782 A1 | 12/2006 | Gunderson et al. | |
| 2009/0233802 A1 | 9/2009 | Bignell et al. | |

FOREIGN PATENT DOCUMENTS

| | | |
|---|---|---|
| EP | 0 238 332 | 9/1987 |
| EP | 0 246 864 | 11/1987 |
| EP | 0 269 764 | 6/1988 |
| EP | 0 357 336 | 3/1990 |
| EP | 0 392 546 | 10/1990 |
| EP | 0 478 319 | 4/1992 |
| EP | 0 320 308 | 11/1993 |
| EP | 0 336 731 | 5/1994 |
| EP | 0 614 987 | 9/1994 |
| EP | 0 439 182 | 4/1996 |
| EP | 0 723 146 | 7/1996 |
| EP | 0 799 897 | 10/1998 |
| EP | 1 121 465 | 9/2002 |
| GB | 2156074 | 10/1985 |
| WO | WO 86/03782 | 7/1986 |
| WO | WO 89/09835 | 10/1989 |
| WO | WO 89/11101 | 11/1989 |
| WO | WO 90/01069 | 2/1990 |
| WO | WO 90/01564 | 2/1990 |
| WO | WO 91/06678 | 5/1991 |
| WO | WO 91/17442 | 11/1991 |
| WO | WO 93/02360 | 2/1993 |
| WO | WO 93/25563 | 12/1993 |
| WO | WO 94/02515 | 2/1994 |
| WO | WO 95/00667 | 1/1995 |
| WO | WO 95/01416 | 1/1995 |
| WO | WO 95/04160 | 2/1995 |
| WO | WO 95/05480 | 2/1995 |
| WO | WO 95/16918 | 6/1995 |
| WO | WO 95/21271 | 8/1995 |
| WO | WO 95/25538 | 9/1995 |
| WO | WO 96/03212 | 2/1996 |
| WO | WO 96/15271 | 5/1996 |
| WO | WO 96/17958 | 6/1996 |
| WO | WO 96/30392 | 10/1996 |
| WO | WO 96/31622 | 10/1996 |
| WO | WO 97/14028 | 4/1997 |
| WO | WO 97/31256 | 8/1997 |
| WO | WO 97/40385 | 10/1997 |
| WO | WO 97/45559 | 12/1997 |
| WO | WO 97/46704 | 12/1997 |
| WO | WO 98/04746 | 2/1998 |
| WO | WO 98/13523 | 4/1998 |
| WO | WO 98/31836 | 7/1998 |
| WO | WO 98/37230 | 8/1998 |
| WO | WO 98/40726 | 9/1998 |
| WO | WO 98/50782 | 11/1998 |
| WO | WO 98/53093 | 11/1998 |
| WO | WO 98/53300 | 11/1998 |
| WO | WO 89/12696 | 12/1998 |
| WO | WO 98/56952 | 12/1998 |
| WO | WO 98/59243 | 12/1998 |
| WO | WO 99/01580 | 1/1999 |
| WO | WO 99/18434 | 4/1999 |
| WO | WO 99/39001 | 8/1999 |
| WO | WO 99/60170 | 11/1999 |
| WO | WO 99/64867 | 12/1999 |
| WO | WO 99/67414 | 12/1999 |
| WO | WO 99/67641 | 12/1999 |
| WO | WO 00/04372 | 1/2000 |
| WO | WO 00/13004 | 3/2000 |
| WO | WO 00/14193 | 3/2000 |
| WO | WO 00/16101 | 3/2000 |
| WO | WO 00/26401 | 5/2000 |
| WO | WO 00/39587 | 7/2000 |
| WO | WO 00/47996 | 8/2000 |
| WO | WO 00/48000 | 8/2000 |
| WO | WO 00/58516 | 10/2000 |
| WO | WO 00/63437 | 10/2000 |
| WO | WO 00/70090 | 11/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/06012 | 1/2001 |
| WO | WO 01/20035 | 3/2001 |
| WO | WO 01/77377 | 4/2001 |
| WO | WO 02/00927 | 7/2001 |
| WO | WO 01/57269 | 8/2001 |
| WO | WO 01/62961 | 8/2001 |
| WO | WO 02/18649 | 8/2001 |
| WO | WO 02/34942 | 10/2001 |
| WO | WO 99/53102 | 10/2001 |
| WO | WO 02/083705 | 4/2002 |
| WO | WO 02/57491 | 7/2002 |
| WO | WO 02/057491 | 7/2002 |
| WO | WO 02/61143 | 8/2002 |
| WO | WO 02/086163 | 10/2002 |
| WO | WO 03/048732 | 6/2003 |
| WO | WO 2004/051224 | 6/2004 |
| WO | WO 2005/068656 | 7/2005 |

OTHER PUBLICATIONS

Drmanac et al., "Sequencing of megabase plus DNA by hybridization: theory of the method," *Genomics* 4:114-128 (1989).

Feil et al., "Methylation analysis on individual chromosomes: improved protocol for bisulphite genomic sequencing," *Nucleic Acids Res.* 22:695-696 (1994).

Frommer et al., "A genomic protocol that yields a positive display of 5-methylcytosine residues in individual DNA strands," *Proc. Natl. Acad. Sci. USA* 89:1827-1831 (1992).

Golub et al., "Molecular classification of cancer: class discovery and class prediction by gene expression monitoring," *Science* 286:531-537 (1999).

Gonzalgo et al., "Rapid quantitation of methylation differences at specific sites using methylation-sensitive single nucleotide primer extension (Ms-SNuPE)," *Nucleic Acids Res.* 25: 2529-2531 (1997).

Goto, "Regulation of X-chromosome inactivation in development in mice and humans," *Microbiol. Mol. Biol. Rev.* 62:362-378 (1998).

Herman et al., "Inactivation of the CDKN2/p16/MTS1 gene is frequently associated with aberrant DNA methylation in all common human cancers," *Cancer Res.* 55:4525-4530 (1995).

Herman, et al., "Methylation-specific PCR: a novel PCR assay for methylation status of CpG islands," *Proc. Natl. Acad. Sci. USA* 93:9821-9826 (1996).

Hermanson, *Bioconjugate Techniques* Academic Press, San Diego, CA, pp. 640-643 (1996).

Huang et al., "Methylation profiling of CpG islands in human breast cancer cells," *Hum. Mol. Genet.* 8: 459-470 (1999).

Issa, et al., "Methylation of the oestrogen receptor CpG island links ageing and neoplasia in human colon," *Nat. Genet.* 7:536-540 (1994).

Jones and Laird, "Cancer epigenetics comes of age." *Nat. Genet.* 21:163-167 (1999).

Kawai, et al., "Comparison of DNA methylation patterns among mouse cell lines by restriction landmark genomic scanning." *Mol. Cell. Biol.* 14:7421-7427 (1994).

Koster et al., "A strategy for rapid and efficient DNA sequencing by mass spectrometry," *Nature Biotechnology* 14:1123-1128 (1996).

Kumar, "Rett and ICF syndromes: methylation moves into medicine," *J. Biosci.* 25:213-214 (2000).

Kuppuswamy et al., "Single nucleotide primer extension to detect genetic diseases: experimental application to hemophilia B (factor IX) and cystic fibrosis genes,"0 *Proc. Natl. Acad Sci. USA* 88:1143-1147 (1991).

Lizardi et al., "Mutation detection and single-molecule counting using isothermal rolling-circle amplification," *Nat. Genet.* 19:225-232 (1998).

Lockhart and Winzeler, "Genomics, gene expression and DNA arrays," *Nature*, 405:827-836 (2000).

Nickerson, "Gene probe assays and their detection," *Current Opinion in Biotechnology* 4:48-51 (1993).

Otterson et al., "CDKN2 gene silencing in lung cancer by DNA hypermethylation and kinetics of p16INK4 protein induction by 5-aza 2'deoxyxytidine," *Oncogene* 11:1211-1216 (1995).

Pierce Chemical Company catalog, technical section on cross-linkers, pp. 155-200 (1994).

Razin, "CpG methylation, chromatin structure and gene silencing-a three-way connection," *Embo J.* 17:4905-4908 (1998).

Reik et al., "Epigenetic reprogramming in mammalian development." *Science* 293:1089-1093 (2001).

Roth, "Bringing out the best features of expression data," *Genome Res.* 11:1801-1802 (2001).

Schafer et al., "DNA variation and the future of human genetics," *Nature Biotechnology* 16:33-39 (1998).

Singer-Sam et al., "A quantitative HpaII-PCR assay to measure methylation of DNA from a small Number of cells," *Nucleic Acids Res.* 18:687 (1990).

Taylor et al., "The diagnostic significance of Myf-3 hypermethylation in malignant lymphoproliferative disorders," *Leukemia* 15:583-589 (2001).

Whitcombe et al., "Detection of PCR products using self-probing amplicons and fluorescence," *Nature Biotechnology* 17:804-807 (1999).

Yan, et al., "Role of DNA methylation and histone acetylation in steroid receptor expression in breast cancer," *J. Mammary Gland Biol. Neoplasia*, 6:183-192 (2001).

Zhong et al., "A survey of FRAXE allele sizes in three populations," *Am. J. Med. Genet.* 64:415-419 (1996).

Abel, "Fiber-Optic Evanescent Wave Biosensor for the Detection of Oligonucleotides," *Anal. Chem.*, 68:2905-2912 (1996).

Anonymous, "Fluorescent Microspheres," Tech. Note 19:1-9 *Bangs Laboratories*. (1997).

Anonymous, "Microsphere Detection Guide," 1-8, *Bangs Laboratories* (1998).

Baner, et al., "More keys to padlock probes," *Curr. Opin. in Biotech.*, 12:11-15.

Bangs, "Immunological Applications Labs of Microspheres," *The Latex Course*, Bangs Labs (1996).

Barany, "Genetic disease detection and DNA amplification using cloned thermostable ligase," *PNAS*, 88:189-193 (1991).

Barnard, et al. "A Fibre-Optic Chemical Sensor with Discrete Sensing Sites," *Nature*, 353:338-340 (1991).

Berg, et al., "Hybrid PCR Sequencing: Sequencing of PCR products using a universal primer," *BioTech.*, 17 (5):896-901 (1994.

Boguszewski, et al., "Cloning of Two Novel Growth Hormone Transcripts Expressed in Human Placenta," *J. of Clinical Endo. and Metabolism*, 83(8):2878-2885 (1998).

Broude, et al., "Enhanced DNA sequencing by hybridization," *PNAS*, 91:3072-3076 (1994).

Chen, "A Microsphere-Based Assay for Multiplexed Single Nucleotide Polymorphism Analysis Using Single Base Chain Extension," *Genome Research*, 10(4):549-557 (2000).

Connor, et al., "Detection of side cell Bs-globin allele by hybridication with synthetic oligonucleotides," *PNAS*, 80:272-282 (1983).

Cunin, "Biomolecular screening with encoded porous-silicon photonic crystals," *Nature*, 39-41 (2002).

Czarnik "Illuminating the SNP Genomic Code," *Mod. Drug Disc.*, 1(2):49-55 (1998).

Dahl, et al., "DNA methylation analysis techniques," *Biogerontology*, 4(4):233-250 (2003).

Drmanac, et al., "Prospects for a Minaturized, Simplified and Frugal Human Genome Project,", *Scientia Yugoslavick*, 16(1-2):97-107 (1990).

Drmanac, "Sequencing by Hybridization," *Auto. DNA Seq and Anal.*, ed. M. (1994).

Drmanac, et al., "Sequencing by Hybridization (SBH) with Oligonucleotide Probes as an Integral Approach for the Analysis of Complex Genomes," *Inter. J. of Genome Research* vol. 1 No. 1, World Scientific Publishing Co., 1992. p. 59-79.

Drmanac, et al., "Sequencing by Oligonucleotide Hybridization: A Promising Framework in Decoding of the Genome Project," *The First Intl. Conf. of Electrophoresis*, 10-13 (1990).

Eads, et al., "MethyLight: a high-throughput assay to measure DNA methylation," *Nucleic Acids Research*, 28(8), e32:i-viii (2000).

Fan, "Parallel Genotyping of Human SNPs Using Generic High-density Oligonucleotide Tag Arrays," *Genome Research*, 10:853-860 (2000).

Feinberg, et al., "Hypomethylation distinguishes genes of some human cancers from their normal counterparts", *Nature*, 301 (5895):89-92 (1983).

Ferguson, J A. et al., "A Fiber-Optic DNA Biosensor Microarray for the Analysis of Gene Expression," *Nature Biotechnol.*, 14:1681-1684 (1996).

Fodor, "Light-Directed, Spatially Addressable Parallel Chemical Synthesis," *Science*, 251:767-773 (1991).

Fuh, "Single Fibre Optic Fluorescene pH Probe", *Analyst*, 112:1159-1163 (1987).

Gonzalgo, et al., "Identification and characterization of differentially methylates religions of genomic DNA by methylation-sensitive arbitrarily primed PCR," *Cancer Res.* 57(4): 594-599 (1997).

Gonzalgo, M. et al., "Quantitative methylation anaylsis using methylation sensitive single nucleotide primer extension (Ms-SNuPE)", *Methods*, 27:128-133 (2002).

Hanada, et al., "bcl-2-gene hypomethylation and high-level expression in B-cell chronic lymphocytic leukemia", *Blood.* 82 (6):1820-1828 (1993).

Hatch, et al., "Rolling circel amplification of DNA immovilized on solid surfaces and its application to multiplex mutation detection," *Genetic Anal. Biomolecular Eng.,*. 15:35-40 (1999).

Hayashizaki, et al., "Restriction landmark genomic scanning method and its various applications," *Electrophoresis*, 14 :251-258 (1993).

Healey, et al., "Development of a Penicillin Biosensor Using a Single Optical Imaging Fiber," *SPIE Proc.*, 2388:568-573 (1995).

Healey, et al., "Fiber Optic DNA Sensory Array Capable of Detecting Point Mutations," *Anal. Biochemistry*, 251(2): 270-279 (1997).

Healey, et al., "Improved Fiber-Optic Chemical Sensor for Penicillin," *Anal. Chemistry*, 67(24):4471-4476 (1995).

Heid, et al., "Real time quantitative PCR", *Genomic Res* 6(10):986-994 (1996).

Hendrickson, E. R. et al., "High sensitivity multianalyte immunoassay using covalent DNA-labeled antibodies and polymerase chain reaction", *Nuc. Acids Res.*, 23(3):522-529 (1995). XP002151883.

Hermanson, "Bioconjugate Techniques", *San Diego Academic Press*, 640-643 (1996).

Hirshfeld, "Laser-Fiber-Optic 'Optrode' for Real Time In Vivo Blood Carbon Dioxide Level Monitoring," *J. of Lightwave Tech.*, LT-5(7):1027-1033 (1987).

Hirschhorn, "SBE TAGS: An Array Based Method for Efficient Nucleotide Polymorphisms Genotyping," *PNAS*, 97:(22)12164-12169 (2000).

Hsuih, "Novel, ligation-dependent PCR assay for detection of Hepatitis C Virus in Serum," *J. of Clinical Microb.*, 34(3):501-507 (1996).

Iannone, "Multiplexed Single Nucleotide Polymorphism Genotyping by Oligonucleotide Ligation and Flow Cytometry," *Cytometry*, 39:131-140 (2000).

Jones, "A iterative and regenerative method for DNA sequencing," *Biotechniques*. 22:939 (1997).

Khanna, et al., "Mutiplex PCR/LDR for detection of K-ras mutations in primary colon tumors," *Oncogens*, 18, 27-38 (1999).

Kozal, "Extensive polymorphisms observed in HIV-1 clade B protease gene using high-density oligonucleotide arrays," *Nature*, (2)753-759 (1996).

Ladner, et al., "Multiplex detection of hotspot mutations by rolling circle-enabled universal microarrays," *Lab. Invest: J. Tech. Meth. Path* 81:1079-1086 (2001).

Lewin, et al., "The Mystique of Epigenetics," *Cell* 93:301-303 (1998).

Lyamichev, "Polymorphism identification and quantitative detection of genomic DNA by invasive cleavage of oligonucleotide probes," *Nature Biotech.*, 17:292-296 (1999).

Metzger, "Termination of DNA syntehsis by novel 3'-modified-deoxyribonucleoside 5'-triphosphases", *Nuc. Acids Res.*, 22(20)4259-4267 (1994).

Michael, et al., "Fabrication of Micro- and Nanostructures Using Optical Imaging Fibers and Their Use as Chemical Sensors", *Proc. 3rd Intl Symp, Microstructures and Microfab. Systems,*, 152-157 (1997).

Michael, et al., "Making Sensors out of Disarray: Optical Sensor Microarrays", *Proc. SPIE*,3270:34-41 (1998).

Michael, et al., "Randomly Ordered Addressable High-Density Optical Sensor Arrays", *Anal. Che.*, 70(7):1242-1248 (1998).

Mignani(Grazia), "In-Vivo Biomedical Monitoring by Fiber-Optic Systems,"*J. of Lighware Tech.*, 13(7):1396-1406 (1995).

Myer, et al., "Synthesis and application of circularizable ligation probes," *BioTechniques*, 30:584-593 (2001).

Newton, et al., "Analysis of any refractory mutation in DNA. The amplification refractory mutation system (ARMS)", *Nucleic Acid Research*, (17)25203-256 (1989).

Nikiforov, et al., "Genetic Bit Analysis: a solid phase method for typing single nucleotide polymorphisms," *Nucl. Acids* Res., 22(20):4157-4175 (1994).

Nilsson, et al., "Padlock probes: circularizing oligonucleotides for localized DNA detection," *Science*, 265:2085-2088 (1994).

Oakeley, "DNA methylation analysis: A review of current methodologies.", *Pharm. Thera*, 84: 389-400 (1999).

Pantano, et al., "Ordered Nanowell Arrays," *Chem Mater*, 8(12):2832-2835 (1996).

Pease, et al., "Light-generated oligonucleotide array for rapid DNA sequence analysis", *PNAS*, 91(11):5502-5026 (1994).

Peterson, et al., "Fiber Optic pH Probe for Physiological Use," *Analytical Chem.*, 52(6):864-869 (1980).

Peterson, et al., "Fiber-Optic Sensors for Biomedical Applications," *Science.*, 13:123-127 (1984).

Piunno, "Fiber-Optic DNA Sensor for Fluorometric Nubleic Acid Determination," *Anal. Chem.*, 67(15):2635-2643 (1995).

Pope, "Fiber Optic Chemical Microsensors Employing Optically Active Silica Microspheres," *SPIE*, 2388:245-266 (1995).

Prezant and Fischel-Ghodsian, "Trapped oligonucleotide nucleotide incorporation (TONI) assay, a simple method for screening point mutations,", *Hum. Mutat.*, 1(2):159-164 (1992).

Ranki, et al., "Sandwich hybridization as a convenient method for the detection of nucleic acids in crude samples," *Gene*, 21:77-85 (1983).

Rein, et al., "Identifying 5-methylcytosine and related modifications in DNA genomes," *Nucleic Acids Res.*, 26(10):2255-2264 (1998).

Ronaghi, et al., "A Sequencing Method Based on Real-Time Phyrophosphate," *Science*, 281 (5375):363-365 (1998).

Roth, et al., "Biotin-avidin microplate assay for the quantitative analysis of enzymatic methylation of DNA by DNA methyltransferase," *Biol. Chem.*, 381:269-272 (2000).

Seradyn, "Sera-Mag Streptavadin Magnetic Microparticles," *Particle Tech.*, 1-7 (1996).

Sheldon, et al., "C-reactive protein and its cytokine mediators in intensive-care patients," *Clin. Chem.*, 39:147-150 (1993).

Shoemaker, "Quantitative phenotypic analysis of yeast deletion mutants using a highly parallel molecular bar-coding strategy," *Nature Genetics*, 14(4):450-456 (1996).

Shuber, A., et al., "High throughput parallel analysis of patient sample for more than 100 mutations disease genes," *Human Molecular Genetics*, 6(3): 337-347 (1996).

Smiraglia, et al., "A new tool for the rapid cloning of amplified and hypermethylated human DNA sequences from restriction landmark genome scanning gels," *Genomics* 58 (3):254-262 (1999).

Smith, et al., "Fluorescence detection in automated DNA sequence analysis", *Nature*, 321:674-679 (1986).

Sooknanan, et al., "Nucleic Acid Sequence-Based Amplification", *Molecular Meth. for Virus Detect.*, Academic Press, Ch. 12, p. 261-285 (1995).

Strachan, "A Rapid General Method for the IDentification of PCR Products Using a Fibre-Optic Biosensor and its Application to the Detection of Listeria,", *Letters in App. Microbiology*, 21(1):5-9 (1995).

Syvanen, "From gels to chips: "Minisequencing" Primer Extension for Analysis of point Mutations and Single Nucleotide Polymorphisms," *Human Mutation*, 13:1-10 (1999).

Thomas, et al., "Amplification of padlock probes for DNA diagnostics by cascade rolling circle amplification or the polymerase chain reaction," *Arch. Pathol. Lab. Med.*, 123:1170-1176 (1999).

Toyota, et al., "Identification of differentially methylated sequences in colorectal cancer by methylated CpG island amplification," *Cancer Res.* 59(10):2307-2312 (1999).

Trinh, et al., "DNA Methylation Analysis by MethyLight Technology", *Methods*, 25:456-462 (2001).

Ugozzoli, "Detection of Specific Alleles by Using Allele-Specific Primer Extension Followed by Capture on Solid Support," *GATA* 9(4):107-112 (1992).

Wallace, et al., "Hybridization of synthetid oligodeoxyribonucleotides to phi chi 174 DNA: the effect of single base pair mismatch," *Nucl. Acid. Res.*, 6:3543-3547 (1979).

Walt, "Bead Based Fiber-Optic Arrays," *Science*, 287:451-452 (1999).

Walt, "Fiber-Optic Imaging Sensors," *Accts. of Chem. Res.*, 31(5)267-278 (1998).

Walt, "Fiber-Optic Sensors for Continuous Clinical Monitoring," *Proc. IEEE*, 80(6) 903-911 (1992).

Xu, et al., "High sequence fidelity in a non-enzymatic DNA autoligation reaction," *Nucl. Acids Research*, (27)875-881 (1999).

Yan, et al., "CpG island Arrays: An application toward deciphering epigenetic signatures of breast cancer," *Clin. Cancer Res.*, 6:1432-1438 (2000).

Yeakley, et al., "Profiling alternative splicing on fiber-optic arrays," *Nature*, 20:353-358 (2002).

Gerry et al., "Universal DNA Microarray Method for Multiplex Detection of Low Abundance Point Mutations," *J. Mol. Biol.* 292:251-262 (1999).

Costello, J F., "Methylation Matters", *Journal of Medical Genetics*, vol. 38(5): 285-303 (May 2001).

Hammons, et al., "Specific site methylation in the 5'-flanking region of *CYP1A2*: Interindividual differences in human livers", *Life Sciences*, 69:839-845 (2001).

Office Action from U.S. Appl. No. 10/194,958, mailed Mar. 13, 2008.
Office Action from U.S. Appl. No. 11/238,826, mailed Mar. 17, 2008.
US 5,719,029, 02/1998, Ohkubo (withdrawn)

* cited by examiner

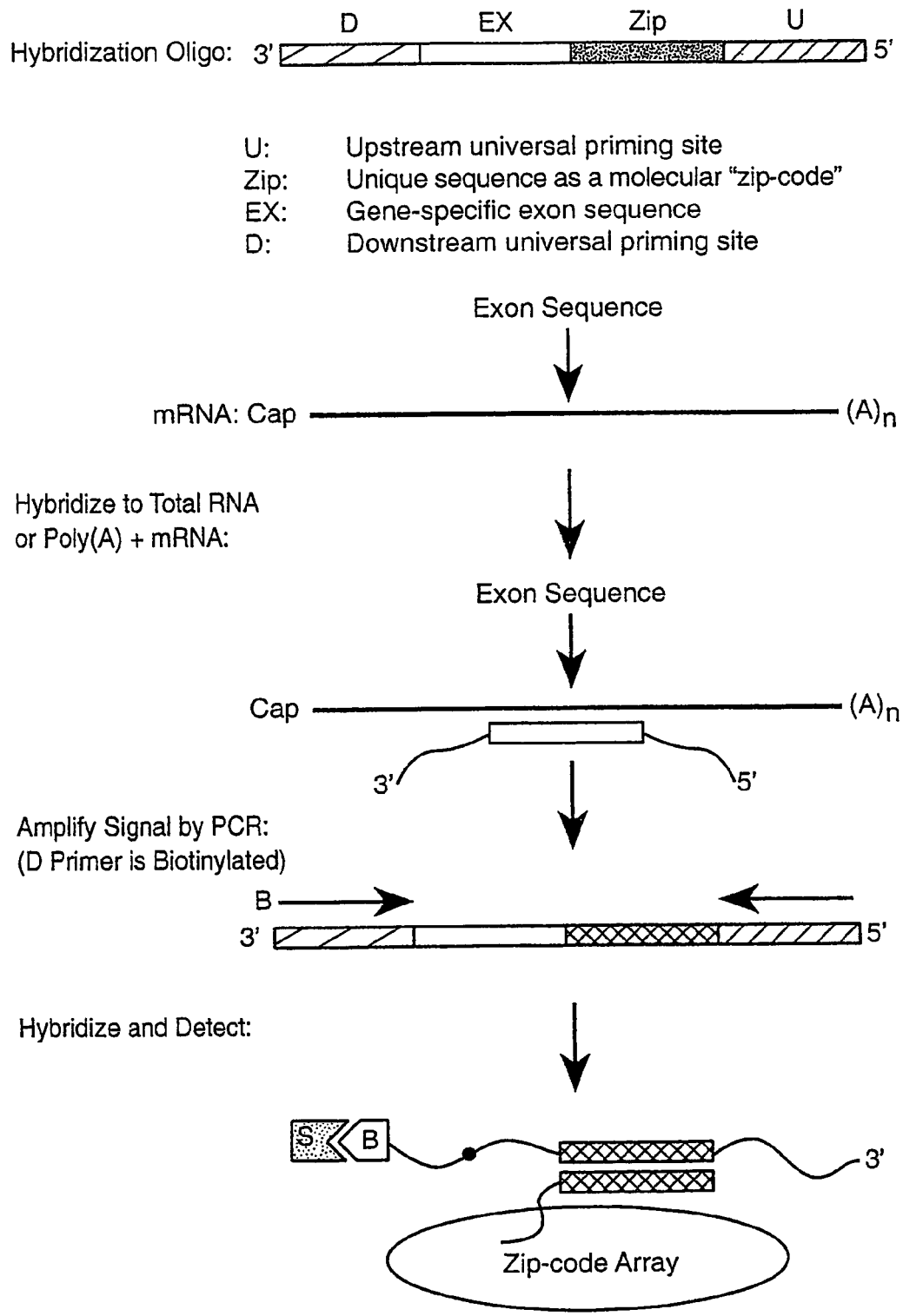
FIG._1

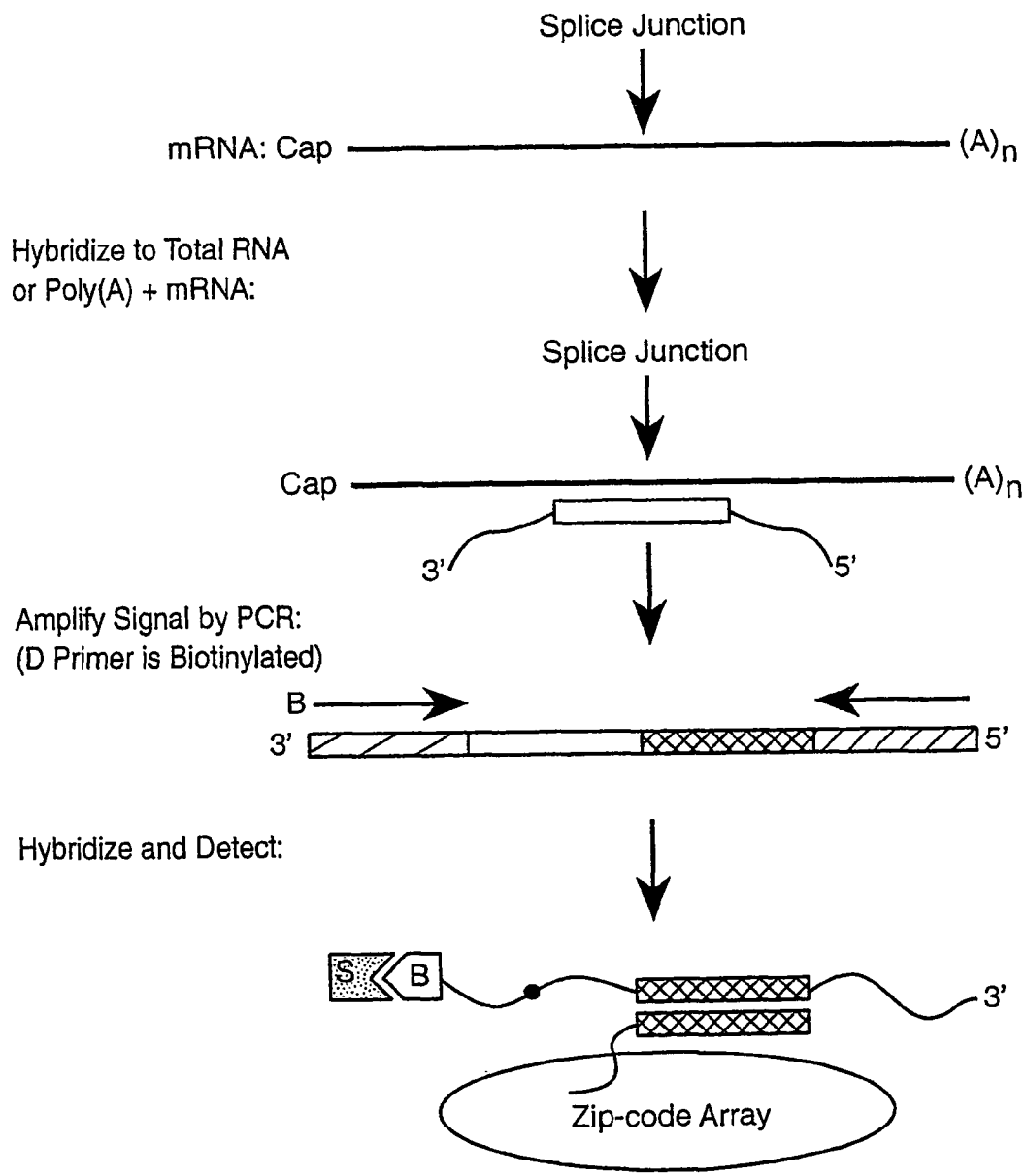
FIG._2

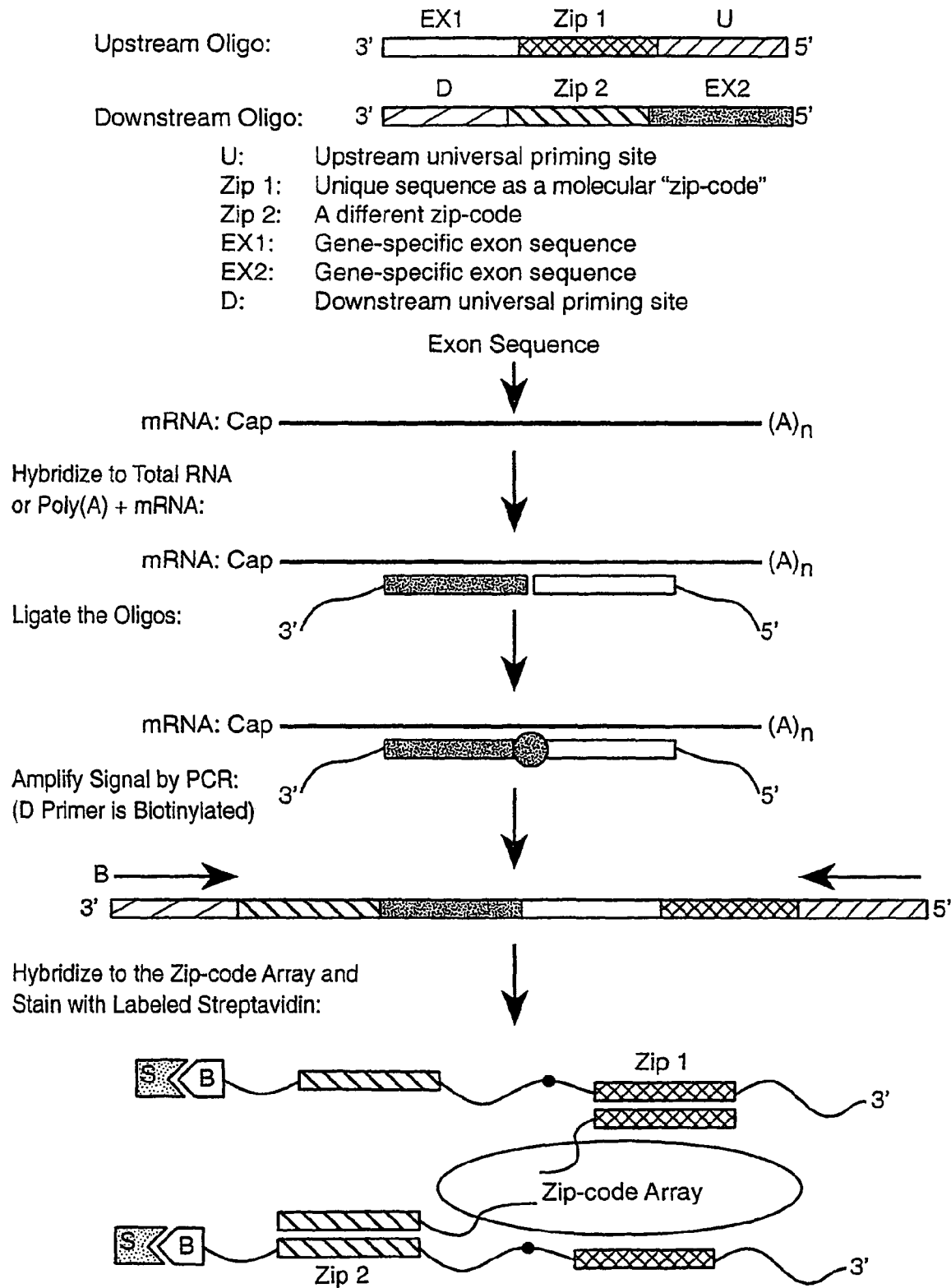
FIG._3

Genome-wide RNA Alternative Splicing Monitoring Using Oligo-Ligation Strategy
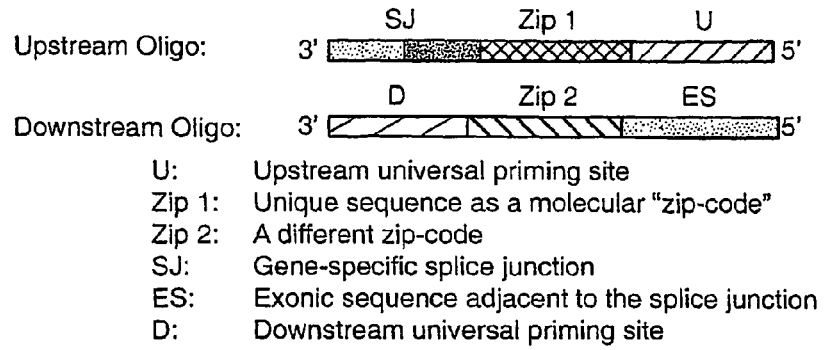
U: Upstream universal priming site
Zip 1: Unique sequence as a molecular "zip-code"
Zip 2: A different zip-code
SJ: Gene-specific splice junction
ES: Exonic sequence adjacent to the splice junction
D: Downstream universal priming site
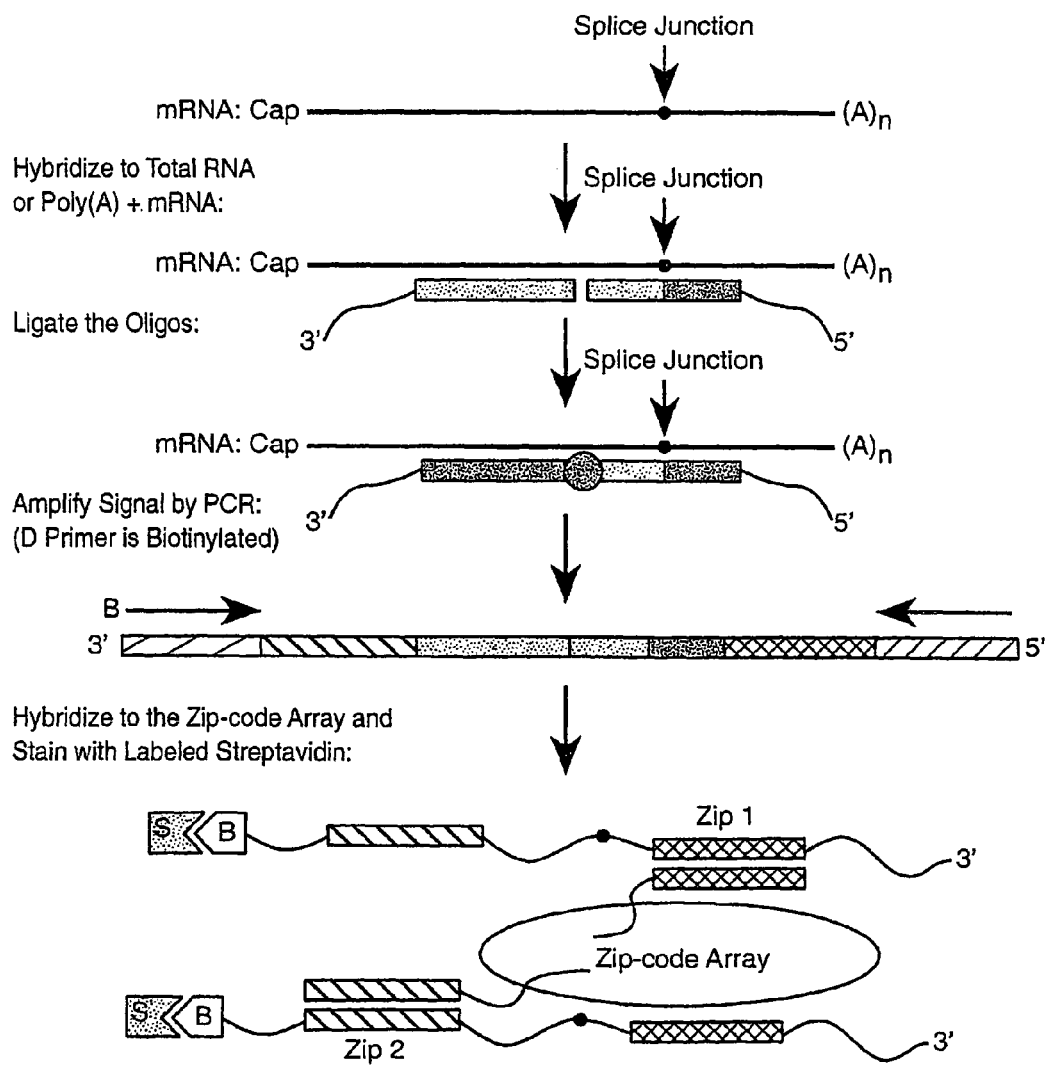
FIG._4

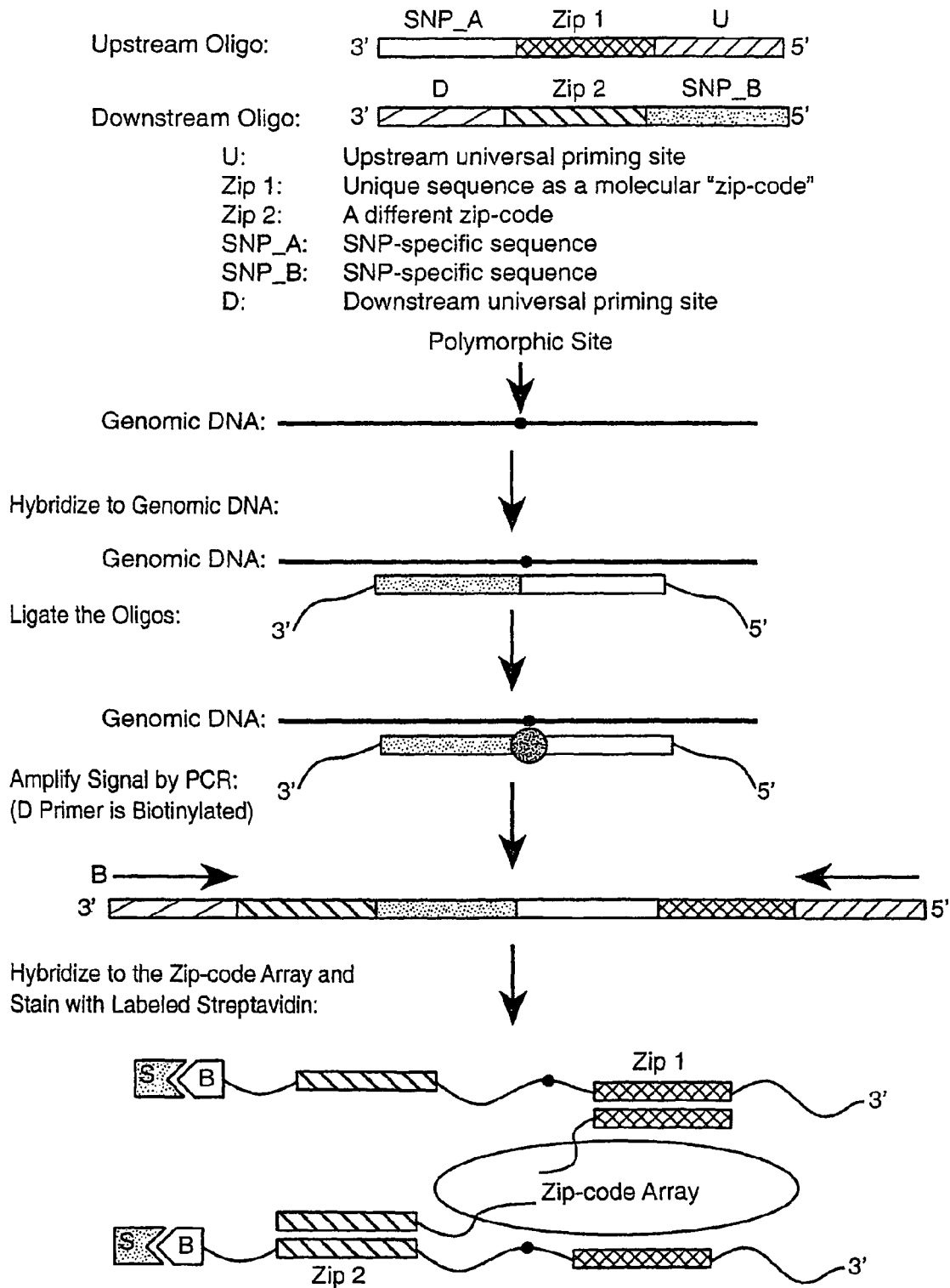
FIG._5

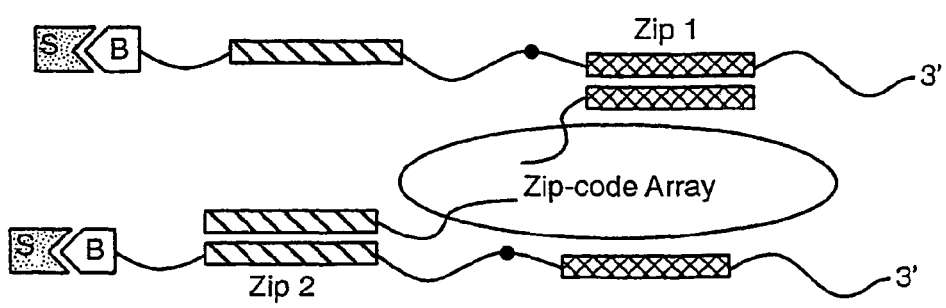
FIG._6

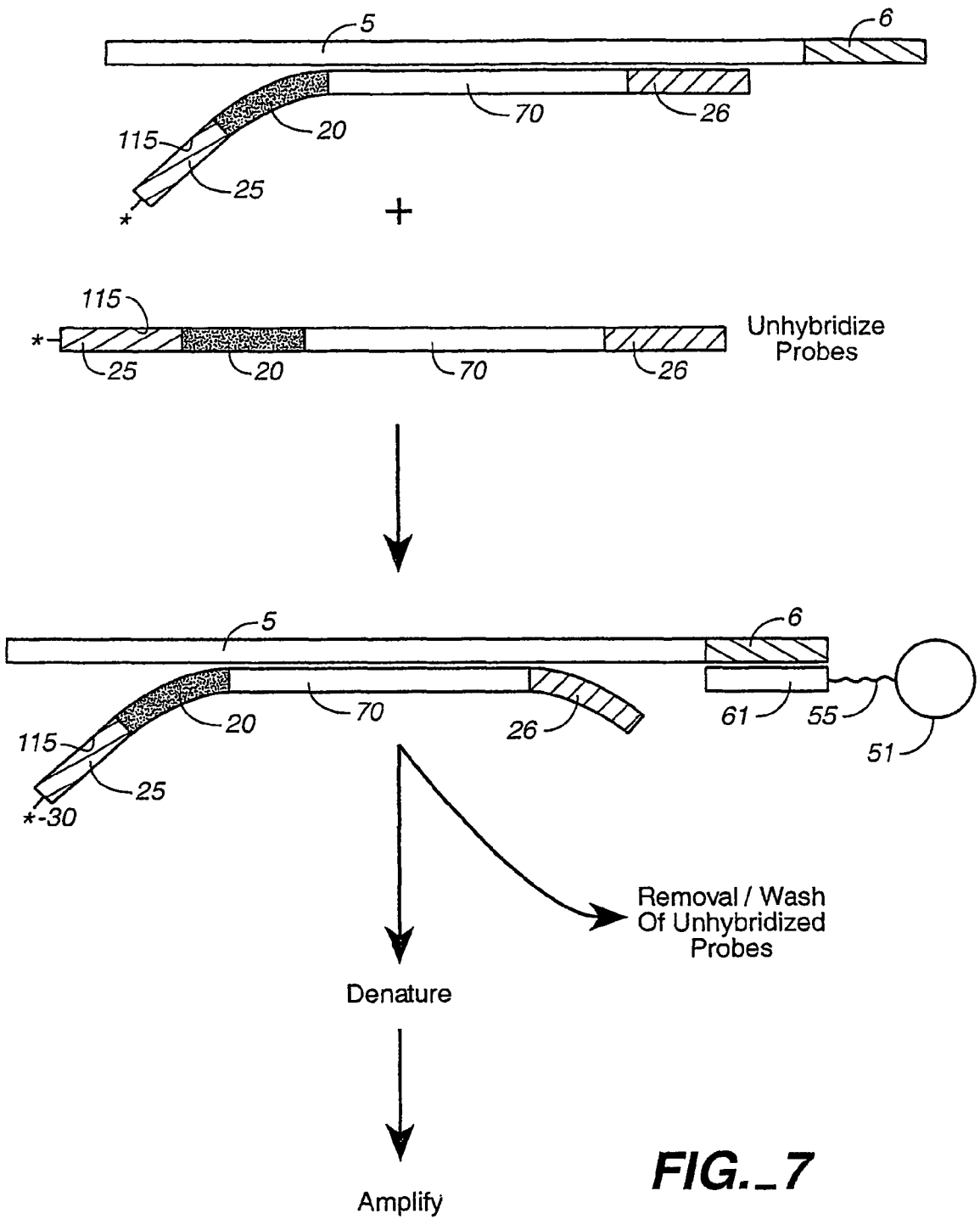
FIG._7

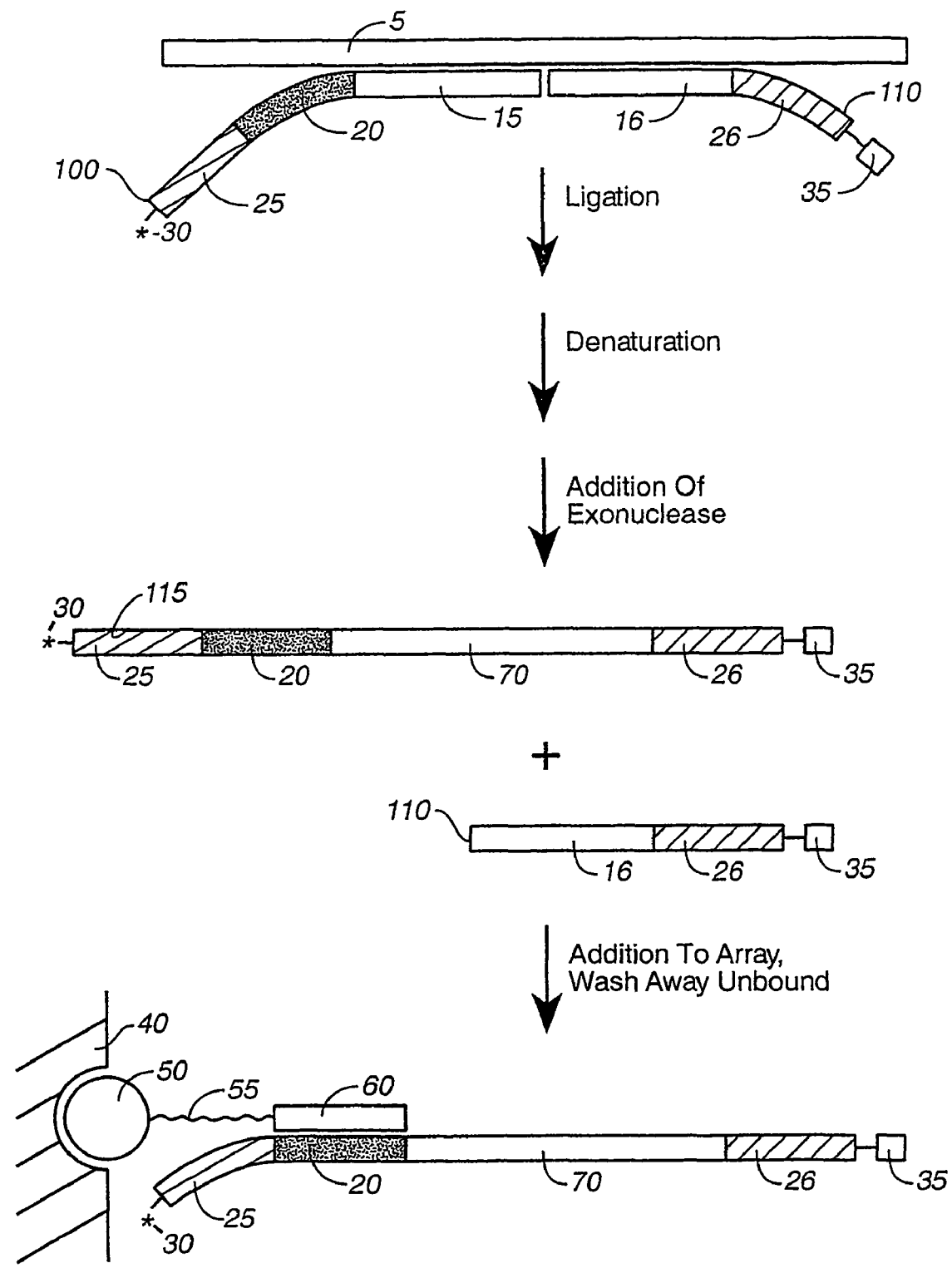
FIG._8

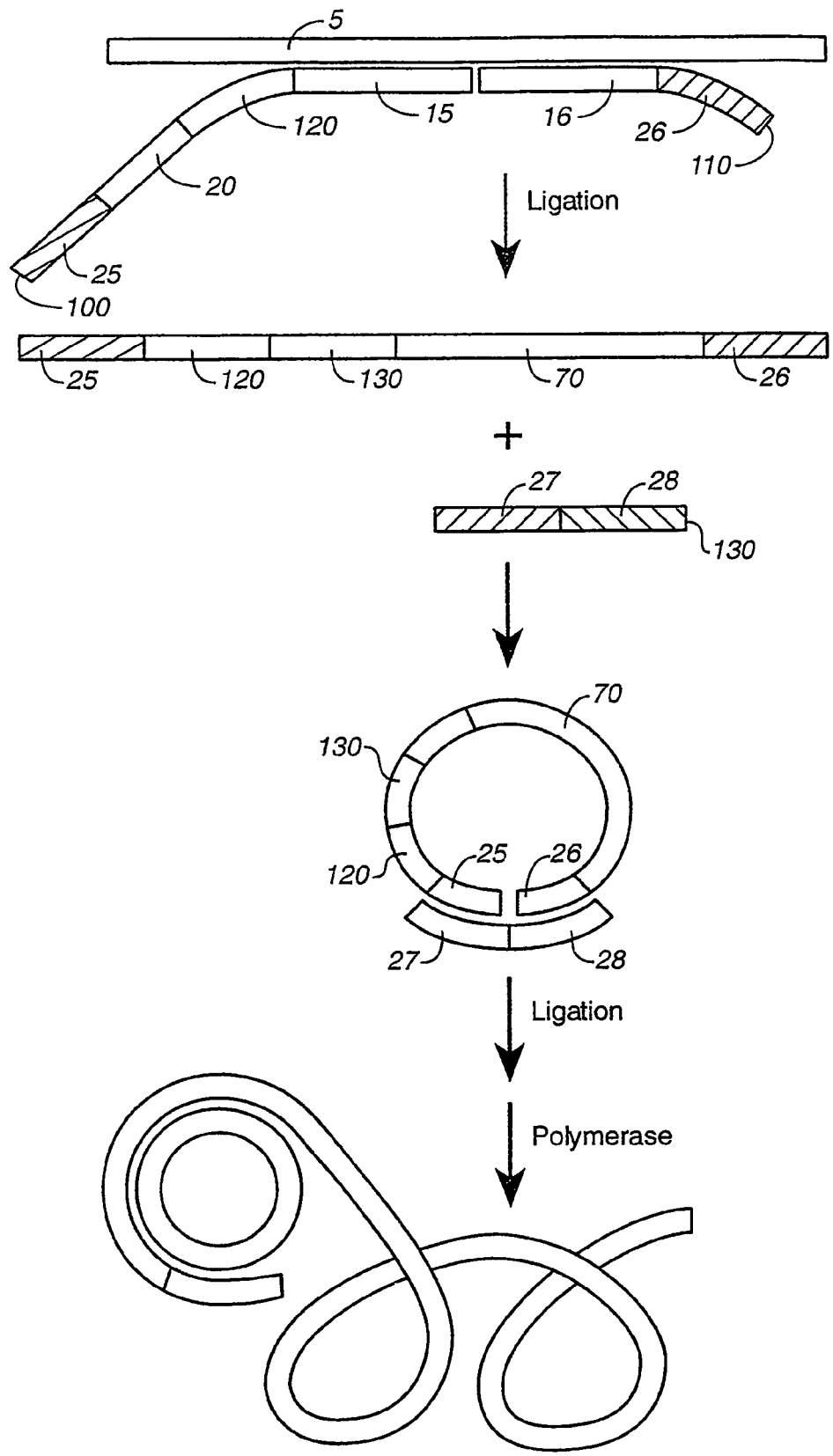
FIG._9

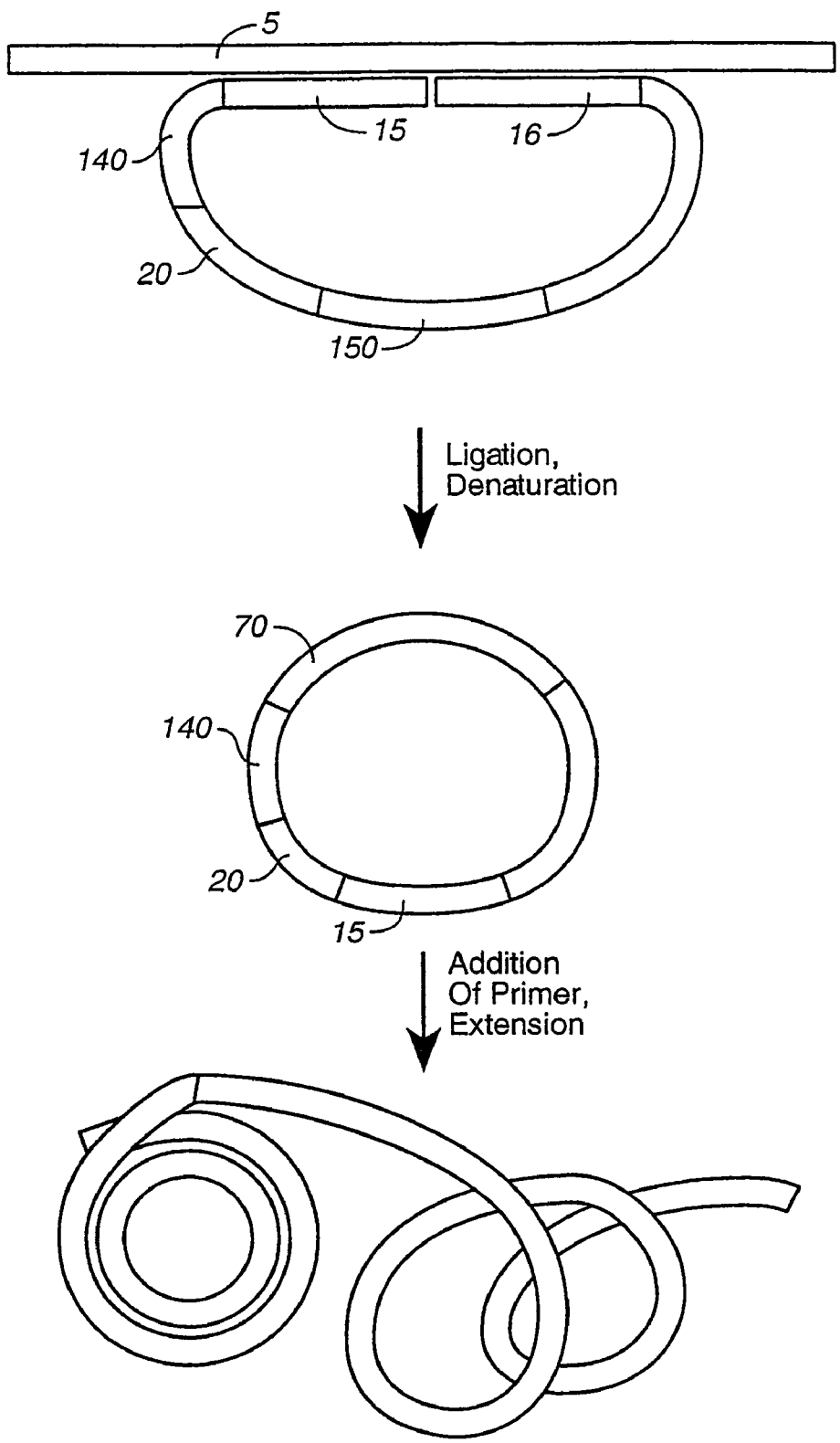
FIG._10

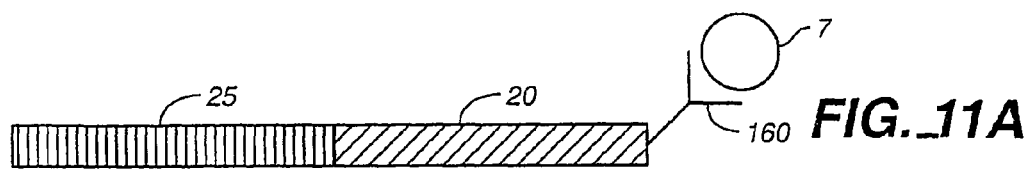
FIG._11A
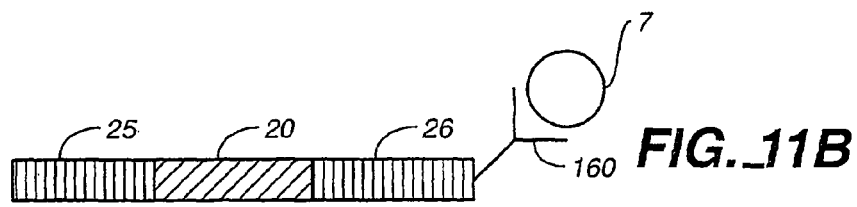
FIG._11B
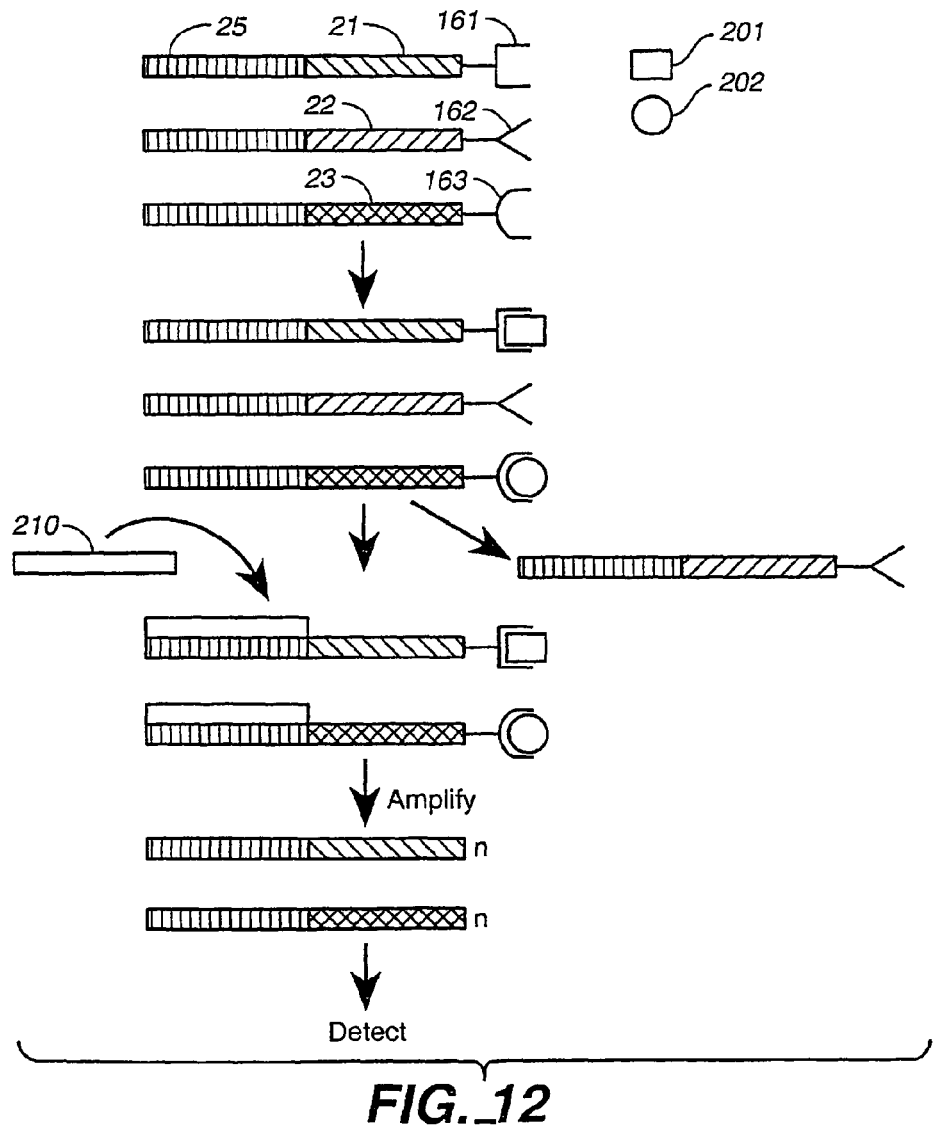
FIG._12

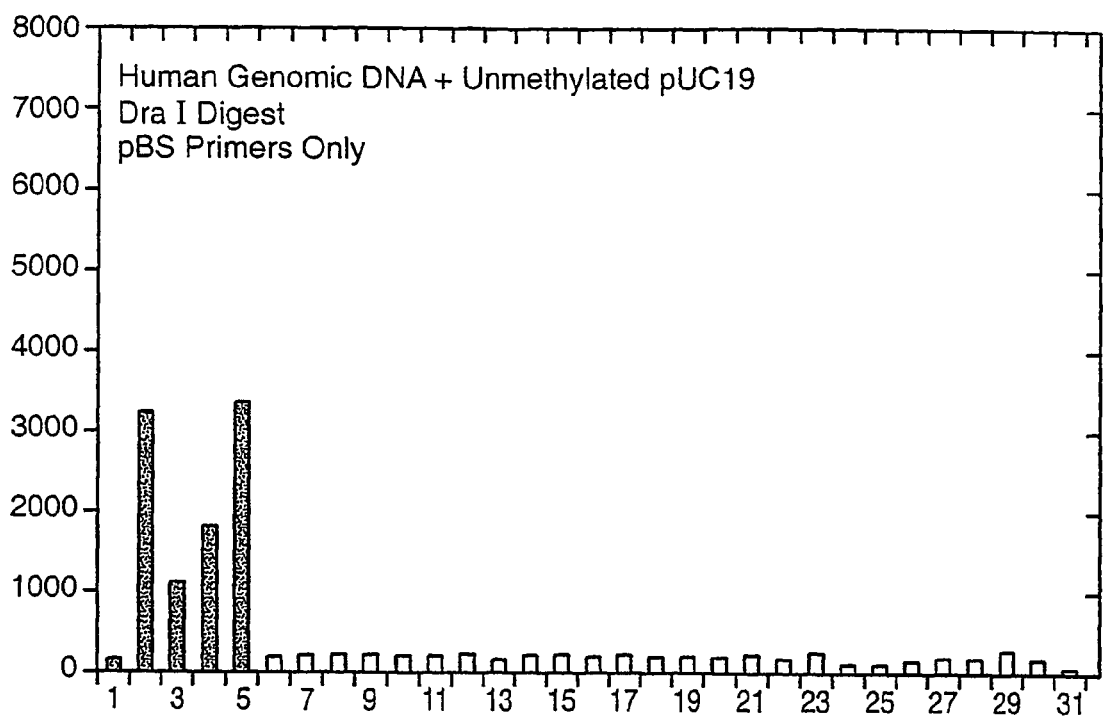
FIG._13A
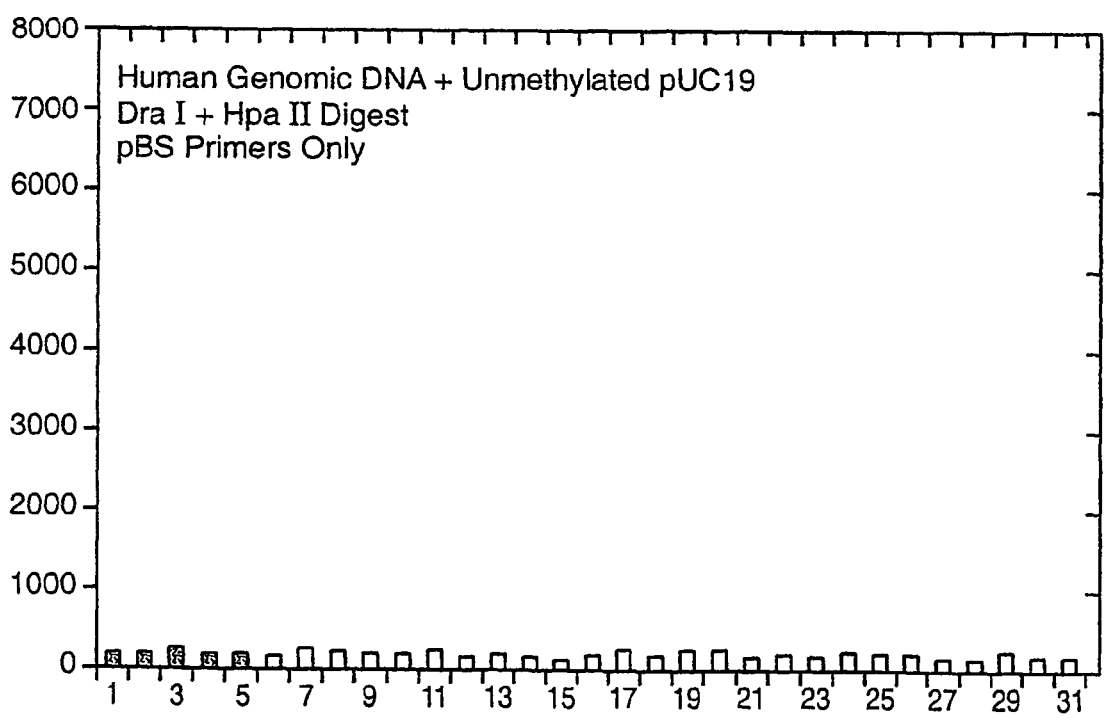
FIG._13B

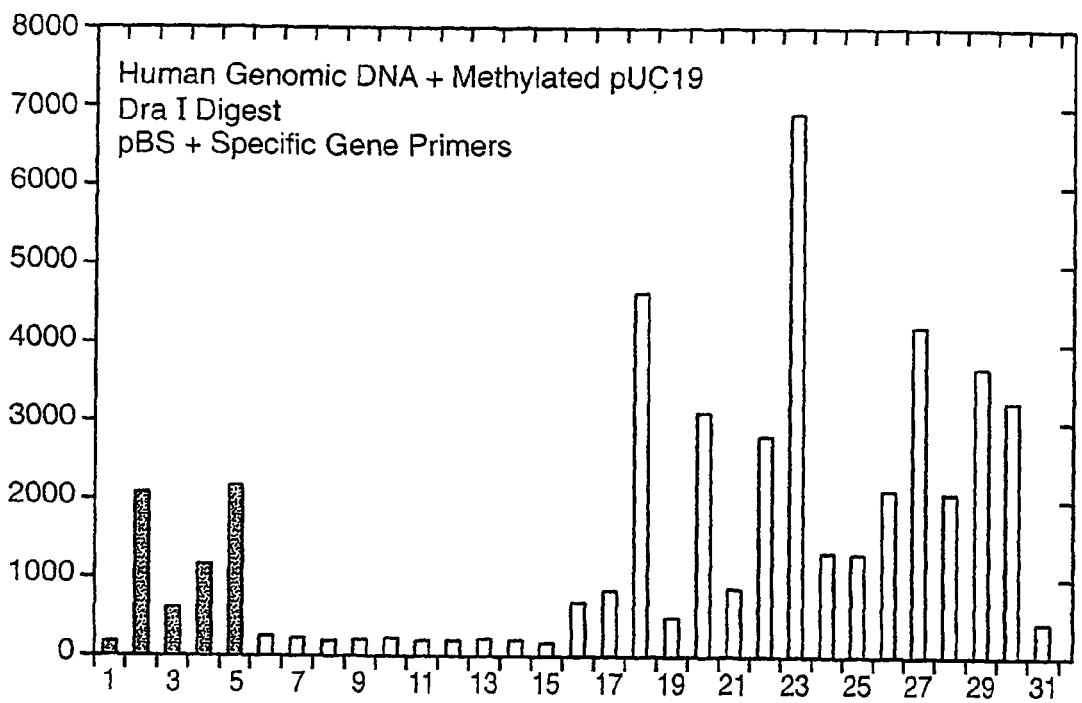
FIG._13C
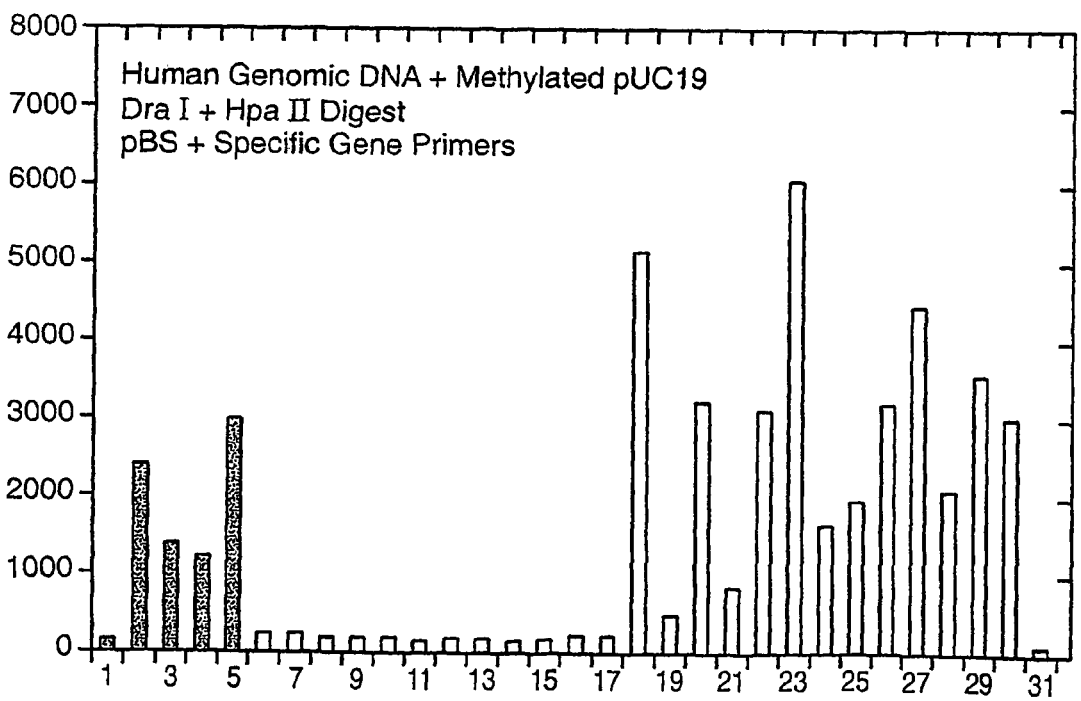
FIG._13D

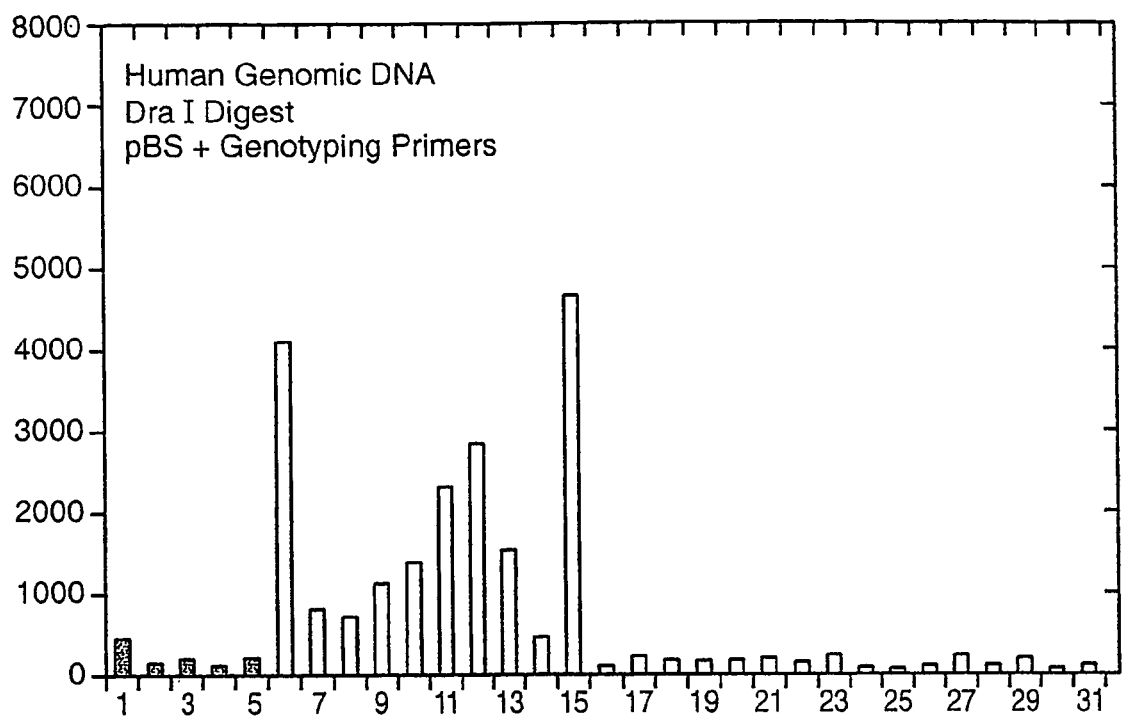
FIG._13E
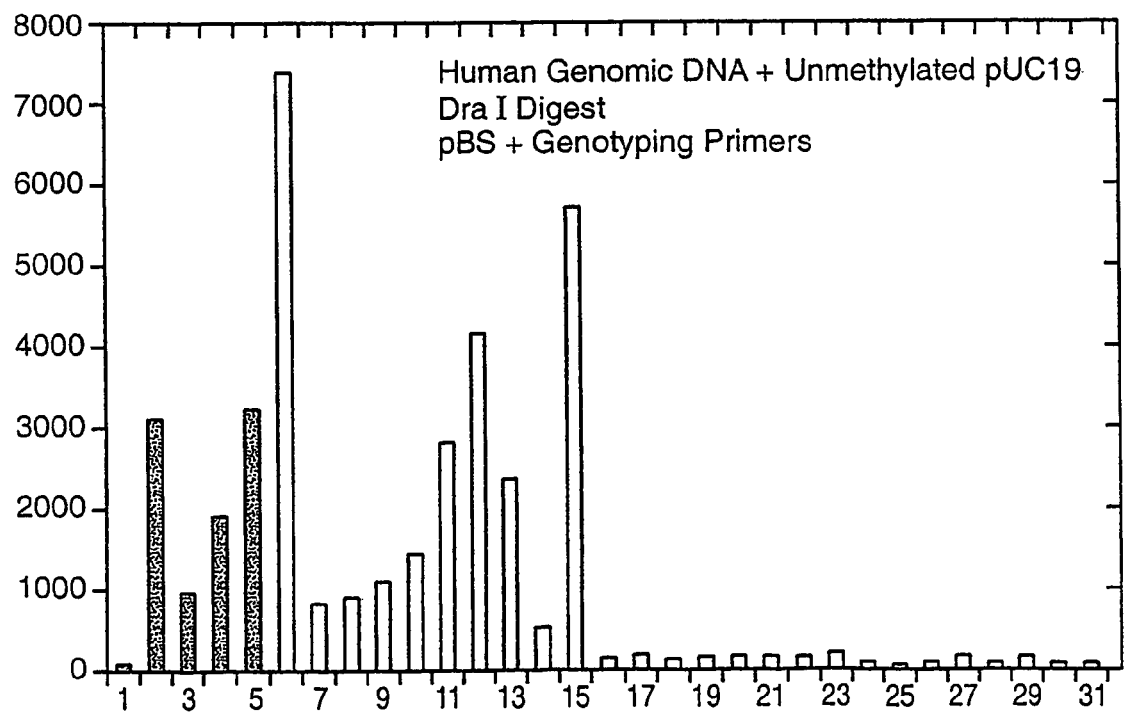
FIG._13F

US 8,076,063 B2

MULTIPLEXED METHYLATION DETECTION METHODS

This application is a national phase under 35 U.S.C. §371 of PCT/US2003/038582, filed Dec. 3, 2003, which is a continuation-in-part of U.S. application Ser. No. 10/309,803, filed Dec. 3, 2002, now U.S. Pat. No. 7,611,869, issued Nov. 3, 2009, both of which are incorporated by reference in their entirety.

This invention was made in part with U.S. Government support under Grant No. CA97851 awarded by the National Institutes of Health. The U.S. Government has certain rights in this invention.

FIELD OF THE INVENTION

The present invention is directed to sensitive and accurate multiplexed assays for target analyte detection.

BACKGROUND OF THE INVENTION

The detection of various target analytes or molecules is an important tool for a variety of application including diagnostic medicine, molecular biology research and detection of contaminants, to name a few. While method of detecting different analytes has evolved, the ability to detect numerous target analytes simultaneously has proven difficult. Detection of multiple proteins, for example has been limited to conventional electrophoresis assays or immunoassays. There has not been a significant multiplexed protein detection assay or method.

The detection of specific nucleic acids is an important tool for diagnostic medicine and molecular biology research. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48-51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41-47 (1993)).

Specificity, in contrast, remains a problem in many currently available gene probe assays. The extent of molecular complementarity between probe, and target defines the specificity of the interaction. Variations in the concentrations of probes, of targets and of salts in the hybridization medium, in the reaction temperature, and in the length of the probe may alter or influence the specificity of the probe/target interaction.

It may be possible under some circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. There are a number of well known polymorphisms that cause clinically important phenotypes; for example, the apoE2/3/4 variants are associated with different relative risk of Alzheimer's and other diseases (see Corder et al., Science 261:921-923 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). However, in Wang et al. only 50% of 558 SNPs were amplified successfully in a single multiplexed amplification reaction. As such, there exists a need for methods that increase the fidelity and robustness of multiplexing assays.

Accordingly, highly multiplexed detection or genotyping of nucleic acid sequences is desirable to permit a new scale of genetic analysis. Simultaneously detecting many hundreds, to multiple thousands of nucleic acid sequences, will require methods which are sensitive and specific despite high background complexity. In order for such reactions to be conducted at low cost to permit widespread use of such techniques, uniform sample preparation and reaction conditions must be applied, preferably in an automatable fashion. A variety of various nucleic acid reaction schemes, amplification techniques, and detection platforms have been used in the past toward this end goal, but none have been able to robustly achieve sensitive, accurate levels of multiplexing beyond a few hundred loci.

In addition, DNA methylation is widespread and plays a critical role in the regulation of gene expression in development, differentiation and disease. Methylation in particular regions of genes, for example their promoter regions, can inhibit the expression of these genes (Baylin, S. B. and Herman, J. G. (2000) DNA hypermethylation in tumorigenesis: epigenetics joins genetics. Trends Genet, 16, 168-174.; Jones, P. A. and Laird, P. W. (1999) Cancer epigenetics comes of age. Nat Genet, 21, 163-167.). Recent work has shown that the gene silencing effect of methylated regions is accomplished through the interaction of methylcytosine binding proteins with other structural compounds of the chromatin (Razin, A. (1998) CpG methylation, chromatin structure and gene silencing-a three-way connection. Embo J, 17, 4905-4908.; Yan, L., Yang, X. and Davidson, N. E. (2001) Role of DNA methylation and histone acetylation in steroid receptor expression in breast cancer. J Mammary Gland Biol Neoplasia, 6, 183-192.), which, in turn, makes the DNA inaccessible to transcription factors through histone deacetylation and chromatin structure changes (Bestor, T. H. (1998) Gene silencing. Methylation meets acetylation. Nature, 393, 311-312.). Genomic imprinting in which imprinted genes are preferentially expressed from either the maternal or paternal allele also involves DNA methylation. Deregulation of imprinting has been implicated in several developmental disorders (Kumar, A. (2000) Rett and ICF syndromes: methylation moves into medicine. J Biosci, 25, 213-214.; Sasaki, H., Allen, N. D. and Surani, M. A. (1993) DNA methylation and genomic imprinting in mammals. Exs, 64, 469-486.; Zhong, N., Ju, W., Curley, D., Wang, D., Pietrofesa, J., Wu, G., Shen, Y., Pang, C., Poon, P., Liu, X., Gou, S., Kajanoja, E., Ryynanen, M., Dobkin, C. and Brown, W. T. (1996) A survey of FRAXE allele sizes in three populations. Am J Med Genet, 64, 415-419.).

In vertebrates, the DNA methylation pattern is established early in embryonic development and in general the distribution of 5-methylcytosine (5 mC) along the chromosome is maintained during the life span of the organism (Razin, A. and Cedar, H. (1993) DNA methylation and embryogenesis. Exs, 64, 343-357.; Reik, W., Dean, W. and Walter, J. (2001) Epigenetic reprogramming in mammalian development. Science, 293, 1089-1093.). Stable transcriptional silencing is critical for normal development, and is associated with several epigenetic modifications. If methylation patterns are not properly established or maintained, various disorders like mental retardation, immune deficiency and sporadic or inherited cancers may follow. The study of methylation is particularly pertinent to cancer research as molecular alterations during malignancy may result from a local hypermethylation of tumor suppressor genes, along with a genome wide demethylation (Schulz, W. A. (1998) DNA methylation in urological malignancies (review). Int J Oncol, 13, 151-167.).

The initiation and the maintenance of the inactive X-chromosome in female eutherians were found to depend on methylation (Goto, T. and Monk, M. (1998) Regulation of X-chromosome inactivation in development in mice and humans. Microbiol Mol Biol Rev, 62, 362-378.). Rett syndrome (RTT) is an X-linked dominant disease caused by mutation of MeCP2 gene, which is further complicated by X-chromosome inactivation (XCI) pattern. The current model predicts that MeCP2 represses transcription by binding methylated CpG residues and mediating chromatin remodeling (Dragich, J., Houwink-Manville, I. and Schanen, C. (2000) Rett syndrome: a surprising result of mutation in MECP2. Hum Mol Genet, 9, 2365-2375.).

Finally, it has become a major challenge in epidemiological genetics to relate a biological function (e.g. a disease) not only to the genotypes of specific genes but also to the potential differential expression levels of each allele of the genes. DNA methylation data can provide valuable information, in addition to the genotype. While it is difficult to obtain the allele-specific methylation information, one object of the invention is to provide methods to determine this information, e.g. if 0, or 1 or 2 chromosomes are methylated at particular genomic locations.

In addition, the identification, classification and prognostic evaluation of tumors has until now depended on histopathological criteria. The purpose of a classification scheme is to identify subgroups of tumors with related properties, which can be further studied and compared with each other. Such classification has been an essential first step in identifying the causes of various types of cancer and in predicting their clinical behavior. However, molecular and biochemical characteristics are not revealed by these approaches. Therefore, the current classification of tumors, although useful, is insufficiently sensitive for prognostic assessment of individual patients (especially for early diagnosis) and for probing the underlying mechanisms involved. An integration of a broad range of information from genetic, biochemical and morphological approaches is needed.

The feasibility of molecular classification and prediction of cancers has been demonstrated using the method of monitoring overall gene expression (Golub, T. R., Slonim, D. K., Tamayo, P., Huard, C., Gaasenbeek, M., Mesirov, J. P., Coller, H., Loh, M. L., Downing, J. R., Caligiuri, M. A., Bloomfield, C. D. and Lander, E. S. (1999) Molecular classification of cancer: class discovery and class prediction by gene expression monitoring. Science, 286, 531-537.). A mathematical model can be developed to predict the disease type without prior pathological diagnosis. However, it is rather difficult to produce reproducible and accurate RNA-based gene expression profiling data under different experimental settings (Lockhart, D. J. and Winzeler, E. A. (2000) Genomics, gene expression and DNA arrays. Nature, 405, 827-836.). Furthermore, it is hard to compare the gene expression data generated from different laboratories using different technology platforms and assay conditions (Roth, F. P. (2001) Bringing out the best features of expression data. Genome Res, 11, 1801-1802.). In addition, there, is scarce availability of reliable patient RNA samples.

DNA methylation pattern changes at certain genes often alter their expression, which could lead to cancer metastasis, for example. Thus, in one object of the invention a detailed study of methylation pattern in selected, staged tumor samples compared to matched normal tissues from the same patient offers a novel approach to identify unique molecular markers for cancer classification. Monitoring global changes in methylation pattern has been applied to molecular classification in breast cancer (Huang, T. H., Perry, M. R. and Laux, D. E. (1999) Methylation profiling of CpG islands in human breast cancer cells. Hum Mol Genet, 8, 459-470.). In addition, many studies have identified a few specific methylation patterns in tumor suppressor genes (for example, p16, a cyclin-dependent kinase inhibitor) in certain human cancer types (Herman, J. G., Merlo, A., Mao, L., Lapidus, R. G., Issa, J. P., Davidson, N. E., Sidransky, D. and Baylin, S. B. (1995) Inactivation of the CDKN2/p16/MTS1 gene is frequently associated with aberrant DNA methylation in all common human cancers. Cancer Res, 55, 4525-4530.; Otterson, G. A., Khleif, S. N., Chen, W., Coxon, A. B. and Kaye, F. J. (1995) CDKN2 gene silencing in lung cancer by DNA hypermethylation and kinetics of p16INK4 protein induction by 5-aza 2'deoxycytidine. Oncogene, 11, 1211-1216.).

RLGS profiling of methylation pattern of 1184 CpG islands in 98 primary human tumors revealed that the total number of methylated sites is variable between and in some cases within different tumor types, suggesting there may be methylation subtypes within tumors having similar histology (Costello, J. F., Fruhwald, M. C., Smiraglia, D. J., Rush, L. J., Robertson, G. P., Gao, X., Wright, F. A., Feramisco, J. D., Peltomali, P., Lang, J. C., Schuller, D. E., Yu, L., Bloomfield, C. D., Caligiuri, M. A., Yates, A., Nishikawa, R., Su Huang, H., Petrelli, N. J., Zhang, X., O'Dorisio, M. S., Held, W. A., Cavenee, W. K. and Plass, C. (2000) Aberrant CpG-island methylation has non-random and tumour-type-specific patterns. Nat Genet, 24, 132-138.). Aberrant methylation of a proportion of these genes correlates with loss of gene expression. Based on these observations, in one object of the invention the methylation pattern of a sizable group of tumor suppressor genes or other cancer-related genes will be used to classify and predict different kinds of cancer, or the same type of cancer in different stages.

Since methylation detection uses genomic DNA, but not the RNA, it offers advantages in both the availability of the source materials and ease of performing the assays. Thus, the methylation assay will be complementary to those based on RNA-based gene expression profiling. It is also possible that the use of different assays in combination may be more accurate and robust for disease classification and prediction.

Thus, methylation is involved in gene regulation. Altered methylation patterns have been associated with various types of diseases including cancers.

Accordingly, it is an object of the invention to provide methods for high-throughput genome-wide detection of genomic amplifications, deletions or methylation. For methylation, previously methods were limited to detection of whether either one of the two chromosomes at a locus were methylated. However, it was not possible to determine if the methylation occurs on one or both chromosomes. Accordingly, the present invention provides a method for determining if zero, one or both chromosomes are methylated at a locus.

Accordingly, it is an object of the invention to provide a very sensitive and accurate multiplexed approach for nucleic acid detection and detection of methylation with uniform sample preparation and reaction conditions.

BRIEF DESCRIPTION OF THE DRAWINGS

FIG. 1 depicts a flow chart for array based detection of gene expression.

FIG. 2 depicts a flow chart for array-based detection of RNA Alternative Splicing.

FIG. 3 depicts a flow chart for genome-wide expression profiling using oligonucleotide-ligation strategy.

FIG. 4 depicts a flow chart for genome-wide RNA alternative splicing monitoring using oligonucleotide-ligation strategy.

FIG. 5 depicts a flow chart for direct genotyping using a whole-genome oligonucleotide-ligation strategy.

FIG. 6 depicts a flow chart for whole-genome oligonucleotide-ligation strategy.

FIG. 7 depicts a preferred embodiment of the invention utilizing a poly(A)-poly(T) capture to remove unhybridized probes and targets. Target sequence 5 comprising a poly(A) sequence 6 is hybridized to target probe 115 comprising a target specific sequence 70, an adapter sequence 20, an upstream universal priming site 25, and a downstream universal priming site 26. The resulting hybridization complex is contacted with a bead 51 comprising a linker 55 and a poly(T) capture probe 61.

FIG. 8 depicts a preferred embodiment of removing non-hybridized target probes, utilizing an OLA format. Target 5 is hybridized to a first ligation probe 100 comprising a first target specific sequence 15, detection position 10, an adapter sequence 20, an upstream universal priming site 25, and an optional label 30, and a second ligation probe 110 comprising a second target specific sequence 16, a downstream universal priming site 26, and a nuclease inhibitor 35. After ligation, denaturation of the hybridization complex and addition of an exonuclease, the ligated target probe 115 and the second ligation probe 110 is all that is left. The addition of this to an array (in this embodiment, a bead array comprising substrate 40, bead 50 with linker 55 and capture probe 60 that is substantially complementary to the adapter sequence 20), followed by washing away of the second ligation probe 110 results in a detectable complex.

FIG. 9 depicts a preferred rolling circle embodiment utilizing two ligation probes. Target 5 is hybridized to a first ligation probe 100 comprising a first target specific sequence 15, detection position 10, an adapter sequence 20, an upstream universal priming site 25, an adapter sequence 20 and a RCA primer sequence 120, and a second ligation probe 110 comprising a second target specific sequence 16 and a downstream universal priming site 26. Following ligation, an RCA sequence 130 is added, comprising a first universal primer 27 and a second universal primer 28. The priming sites hybridize to the primers and ligation occurs, forming a circular probe. The RCA sequence 130 serves as the RCA primer for subsequent amplification. An optional restriction endonuclease site is not shown.

FIG. 10 depicts preferred a rolling circle embodiment utilizing a single target probe. Target 5 is hybridized to a target probe 115 comprising a first target specific sequence 15, detection position 10, an adapter sequence 20, an upstream universal priming site 25, a RCA priming site 140, optional label sequence 150 and a second target specific sequence 16. Following ligation, denaturation, and the addition of the RCA primer and extension by a polymerase, amplicons are generated. An optional restriction endonuclease site is not shown.

FIG. 11 depicts two configurations of probes for multiplex detection of analytes. A depicts a probe containing an adapter 20, an upstream priming site 25 and a target-specific portion, i.e. bioactive agent 160 bound to a target analyte 7. B depicts a probe containing an adapter 20, an upstream universal priming site 25, a downstream universal priming site 26 and a target-specific portion, i.e. bioactive agent 160 bound to a target analyte 7.

FIG. 12 depicts a preferred method for multiplex detection of analytes. Probes containing universal priming sequence 25 and adapters that identify the target analyte to be detected 21, 22 and 23, and target specific portions, i.e. bioactive agents 161, 162 and 163 are contacted with target analytes 201 and 202. Probes to which target analytes bind are contacted with universal primers 210 and amplification reaction mixture. Amplicons are detected and serve as an indication of the presence of the target analyte.

FIG. 13 In vitro controls for methylation profiling in the presence of complex genome with a readout on fiber optic arrays. a). Panels A and B show that the signal detected by bead arrays from the plasmid-specific primers (red bars, 1-5 in panel A) completely disappears after Hpa II digest of unmethylated DNA (1-5 in panel B). Plasmid primers do not cross-react with genomic DNA. Primer 1 used as a negative control has no homology site on the pUC19 plasmid and shows no signal. b). Panels C and D demonstrate that in vitro methylated plasmid DNA is completely resistant to Hpa II digest. Signals from plasmid primers (red bars, 1-5) and genomic DNA primers (yellow bars, 16-31) are specific. Genes represented in columns 16, 17, 20, 24 and 28 have a Hpa II site at or near the primer annealing site. Note that signals in the columns 16 and 17 on the panel C disappear completely on the panel D, which may indicate unmethylated status of the targeted loci. The signals from the plasmid primers remained unchanged and confirm that pUC19 was completely methylated. c). Panels E and F show that addition of genotyping probes (blue bars, 6-15) in combination with plasmid primers (red bars, 1-5) designed for non-methylated DNA can be used to monitor the quality of hybridization process and DNA treatment.

SUMMARY OF THE INVENTION

In accordance with the embodiments outlined above, the present invention permits highly multiplexed detection of target analytes. The method includes contacting target analytes with a composition comprising an amplification enzyme and first and second target probes. The first and second target probes comprising a first and second bioactive agent, respectively, that specifically bind to the first and second target molecules. The probes also comprise a first and second adapter sequence, respectively, such that the first adapter sequence identifies the first target molecule and the second adapter sequence identifies the second target molecule, and at least a first and second upstream universal priming sequence, respectively. The first and second adapter sequences, wherein no ligation is performed, to form first and second amplicons, respectively, and detecting the first and second amplicons, whereby the first and second target molecules, respectively, are detected.

In addition, the invention provides a method for multiplex detection of a plurality of target molecules comprising contacting a plurality of target molecules with a composition comprising an amplification enzyme and a plurality of target probes, each comprising a bioactive agent, wherein the bioactive agent binds to discrete target molecules an adapter sequence that identifies the discrete target molecule that binds the bioactive agent and at least a first upstream universal primer, amplifying the adapter sequences, wherein no ligation is performed, to form a plurality of amplicons, and detecting the plurality of amplicons, whereby the plurality of target molecules, are detected.

In addition, present invention permits highly multiplexed nucleic acid detection reactions under uniform sample preparation and reaction conditions. That is, preferably the method includes multiplexing from hundreds to thousands of assays simultaneously, more preferably up to tens of thousands of assays simultaneously, most preferably up to millions of assays. The inventive method preferably includes 1) immobilizing the sample nucleic acids to be interrogated (in a preferred embodiment, genomic DNA) on a capture surface, such as a solid phase (in a preferred embodiment, immobilizing the genomic DNA on beads); 2) simultaneously conducting at least a first step of a nucleic acid detection reaction with the captured nucleic acids (in the preferred embodiment, the nucleic acid detection reaction comprises two phases: the first phase involves the exposure of the sample nucleic acids to a set of sequence-specific probe(s), the second phase involves an enzymatic step to assure specificity of the nucleic acid detection reaction. The probes used include at least one appropriate universal amplification priming site); 3) a stringent wash step to reduce the complexity of the multiplexed probe mixture by washing away unhybridized probes; 4) optionally conducting the second phase of the nucleic acid detection reaction step of 2) above (in the case of for example competitive hybridization as the nucleic acid detection reaction, no second phase is required); 5) releasing the probes from the sample nucleic acid; 6) amplification of the released probes (exponential or linear amplification schemes such as PCR, or Invader™, ESPIA (see WO 01/20035, which is expressly incorporated herein by reference), T7 amplification or the novel amplification method disclosed in Application patent application filed Jul. 12, 2001, entitled METHODS OF MULTIPLEXING AMPLIFICATION AND GENOTYPING REACTIONS (no serial number received)) using the universal amplification priming site(s) on the probes; and 6) detection and readout of the amplified signals on any detection platform (in a preferred embodiment, the randomly assembled BeadArray™ technology platform).

In addition the invention provides a method for multiplex detection of methylation of target nucleic acids comprising providing a first population of target nucleic acids labeled with a purification tag, cleaving the first population of target nucleic acids with an enzyme, whereby the enzyme discriminately cleaves at methylation target sequences forming a second population of cleaved target sequences, immobilizing the first and second populations by the purification tag and detecting the presence of the first population comprising non-cleaved target nucleic acid whereby the presence of the first population comprising non-cleaved target nucleic acid indicates the presence of methylated target nucleic acids.

The invention also provides a method of detecting methylation contacting a sample of target nucleic acids with bisulfite, whereby non-methylated cytosine is converted to uracil, and methylated cytosine is not converted to uracil; contacting said treated target nucleic acids with a first probe that hybridizes with a methylated target in said first population of target nucleic acid and a second probe that hybridizes with a non-methylated target in said second population of target nucleic acid, forming first and second hybridization complexes, respectively; contacting said first and second hybridization complexes with an enzyme that modifies said first and second probes forming first and second modified probes; and detecting said first and second modified probes to determine the presence of methylation in said target nucleic acid.

In addition the invention provides a method of detecting methylation comprising contacting a sample of target nucleic acids with bisulfite, whereby non-methylated cytosine is converted to uracil forming a first population of treated target nucleic acids, and methylated cytosine is not converted to uracil forming a second population of treated target nucleic acids, contacting the first and second populations of treated target nucleic acids with a first probe that hybridizes with a first target in the first population of target nucleic acid and a second probe that hybridizes with a target in the second population of target nucleic acid, forming first and second hybridization complexes, respectively, contacting the first and second hybridization complexes with an enzyme that modifies the first and second probes forming first and second modified probes, and detecting the first and second modified probes to determine the presence of methylation in the target nucleic acid.

The invention also provides methods for detecting methylation that allow for whole genome amplification after bisulfite conversion in a manner that takes advantage of the unique sequence feature introduced into genomic DNA sequences by sodium bisulfite treatment, which is the deamination of cytosine, but not 5-methylcytosine, to uracil. In one embodiment, the invention provides a method of detecting methylation following bisulfite conversion of target nucleic acids, said method comprising providing target nucleic acids that have undergone bisulfite conversion, contacting said target nucleic acids with two sets of primers, wherein a first set of said two sets of primers has a higher affinity for an original bisulfite converted strand of said target nucleic acid compared to a corresponding complementary strand that has not undergone bisulfite conversion and wherein a second set of said two sets of primers has a higher affinity for said corresponding complementary strand compared to said original bisulfite converted strand of said target nucleic acid, wherein said contacting is done under conditions that allow the primers to hybridize to a complimentary nucleic acid sequence, and amplifying said bisulfite converted strand of said target nucleic acid and said corresponding complementary strand. In a related embodiment, an initial contacting step is performed that further comprises addition of a set of poly-A primers.

The invention also provides a method for detecting methylation following bisulfite conversion of target nucleic acids, the method comprising providing target nucleic acids that have undergone bisulfite conversion, contacting the target nucleic acids with primer sequences comprising poly-Adenines to synthesize a population of first strand products, modifying said population of first strand products to add poly-Thymine sequences; contacting said modified first strand products with poly-Adenine primers under conditions that allow the primers to hybridize to a complimentary nucleic acid sequence; and amplifying said modified first strand products. In particular embodiments, modifying the population of first strand products can be carried out by contacting the population of first strand products with Thymine in the presence of an enzyme that allows for adding poly-Thymine sequences to the first strand products. The addition of poly-Thymine sequences to a population of first strand products can be accomplished using any of a variety of methods known in the art including, for example, use of a terminal deoxyribonucleotide transferase enzyme in the presence of thymine triphosphate. Other methods include, without limitation, chemical synthesis or nucleotide extension methods in which the first strand products are extended in the presence of an annealed template having a poly adenine sequence.

Also provided is a method for generating a calibration curve for the quantitative methylation measurement of an unknown sample, said method comprising providing and amplifying a first reference genomic DNA, for example, at least one hundred fold, one thousand fold, ten thousand fold or more, wherein the ratio of methylated to unmethylated sequences is decreased sufficiently to prepare a virtually unmethylated template population; obtaining a methylated template population comprising nucleotide sequences corresponding to the nucleotide sequences of said reference genomic DNA; and separately mixing fixed amounts of said virtually unmethylated template population with fixed amounts of said methylated template population at various distinct ratios to create a series of mixtures that represents a methylation gradient, wherein a calibration curve is generated for quantitative methylation measurements. In this embodiment, the invention also provides a method for producing a calibration reagent for quantitative methylation measurement of an unknown sample of the reference organism.

The invention also provides a calibration curve and a calibration reagent prepared by the method described above that allows for quantitative calibration of any genomic DNA methylation measurement, regardless of the methylation detection system utilized. The invention also provides a calibration curve comprising a first axis indicating the amount of unmethylated template population compared to methylated template population and a second axis indicating a detected methylation signal.

DETAILED DESCRIPTION OF THE INVENTION

The present invention is directed to the multiplex preparation and detection of methylated target nucleic acids. In general, the invention involves the use of methylation selective modification of target nucleic acids and detection of the modified target nucleic acids. In one embodiment the methylation selective modification involves cleaving target nucleic acids with methylation selective enzymes and detection of the cleaved or uncleaved nucleic acids with probes. That is, in a preferred embodiment the method involves providing a first population of target nucleic acids as described herein and cleaving or shearing the first population so as to reduce the size of each target. The target nucleic acids can be any region including but not limited to non-polymorphic regions. The sized target nucleic acids are then labeled with a purification tag as described herein. The labeled target nucleic acids are cleaved with an enzyme that discriminately cleaves at methylated sites, that is the enzyme either selectively cleaves or does not cleave at a site that is methylated. Therefore, the term "methylated target sequence" as used in reference to an enzyme that discriminately cleaves at the site of the target sequence refers to target sequences for methylation, regardless of methylation status, and are interchangeably referred to as "methylation target sequences." Typically, the discrimination is based on methylation blocking restriction such that methylation target sequences in non-methylated state are discriminately cleaved by the enzyme. Generally and preferably the enzyme has sequence specificity in addition to methylation sensitivity, such as Hpa II. This cleaved and labeled mixture is then immobilized to a solid support. Generally this is accomplished by the purification tag. Detection of the methylated target sequence is then performed, using any variety of assays. Generally, these assays rely on primers or probes that span the junction site.

In addition, the results obtained from different gDNAs treated with or without methylation selective enzymes can be compared to deduce the genomic methylation pattern.

In another embodiment the method involves the use of bisulfite. That is, in an alternative method for detecting methylation, the fact that non-methylated cytosines are converted to uracils when treated with bisulfite is exploited. The hybridization properties of uracil are similar to that of thymine. Thus, when the sample DNA is treated with bisulfite, non-methylated cytosine hybridizes like thymine, while methylated cytosine will hybridize like cytosine. This difference in hybridization properties can be detected by using appropriate target probes. That is, the methylated or non-methylated cytosine site can be treated as a C/T polymorphic site and detected by any of the assays as described herein. The resulting modified target probes are detected by any of the detection methods as described herein.

In addition the invention provides a method for detecting methylation following bisulfite conversion of target nucleic acids, the method comprising providing target nucleic acids that have undergone bisulfite conversion, contacting the target nucleic acids with two sets of primers, wherein a first set of the two sets of primers has a higher affinity for an original bisulfite converted strand of the target nucleic acid compared to a corresponding complementary strand that has not undergone bisulfite conversion and wherein a second set first set of the two sets of primers has a higher affinity for the corresponding complementary strand compared to the original bisulfite converted strand of the target nucleic acid, wherein the contacting is done under conditions that allow the primers to hybridize to a complimentary nucleic acid sequence, and amplifying the bisulfite converted strand of the target nucleic acid and the corresponding complementary strand. In a related embodiment, an initial contacting step is performed that further comprises addition of a set of poly-A primers. An exemplary set of primers having higher affinity for an original bisulfite converted strand of a target nucleic acid compared to a corresponding complementary strand that has not undergone bisulfite conversion include a set of primers that contains combinations of A, T and C nucleotides but not G as described in Example 3.

The invention also provides a method for detecting methylation following bisulfite conversion of target nucleic acids, the method comprising providing target nucleic acids that have undergone bisulfite conversion, contacting the target nucleic acids with primer sequences comprising poly-Adenines to synthesize a population of first strand products, modifying said population of first strand products to add poly-Thymine sequences; contacting said modified first strand products with poly-Adenine primers under conditions that allow the primers to hybridize to a complimentary nucleic acid sequence; and amplifying said modified first strand products. In particular embodiments, modifying the population of first strand products can be carried out by contacting the population of first strand products with Thymine in the presence of an enzyme that allows for adding poly-Thymine sequences to the first strand products.

Poly-Thymine tracts can be added to a population of first strand products using any of a variety of methods known in the art including, for example, use of a terminal deoxyribonucleotide transferase enzyme in the presence of thymine triphosphate. Other methods include, without limitation, chemical synthesis or nucleotide extension methods in which the first strand products are extended in the presence of an annealed template having a poly adenine sequence.

The invention methods for detecting methylation allow for whole genome amplification after bisulfite conversion in a manner that takes advantage of the unique sequence feature introduced into genomic DNA sequences by sodium bisulfite treatment, which is the deamination of cytosine, but not 5-methylcytosine, to uracil.

Thus, the invention also involves the use of probes that comprise a number of components. First of all, the probes comprise a bioactive agent (e.g. one of a binding partner pair) that will bind to all or a portion of the target nucleic acid. This bioactive agent preferably comprises nucleic acid, because the target analyte is a target nucleic acid sequence. The probes further comprise at least one adapter nucleic acid sequence that uniquely identifies the target nucleic acid. That is, there is a unique adapter sequence/target nucleic acid pair for each unique target nucleic acid, although in some cases, adapter sequences may be reused.

In addition, the probes also comprise at least one universal nucleic acid priming sequence that will allow the amplification of the adapter sequence. In some cases, one universal priming sequence can be used, for example when the priming sequence comprises an RNA polymerase priming sequence such as a T7 site. Alternatively, two universal priming sequences can be used, such as standard PCR priming sequences, as long as they flank the adapter sequence, e.g. one priming sequence is 5' to the adapter sequence and one is 3'. Once the probes have been added to the target nucleic acids to form assay complexes (sometimes referred to herein as hybridization complexes) generally the unhybridized probes are washed away, using a variety of techniques as outlined herein.

Amplification proceeds in a number of ways. In general, when an RNA polymerase priming sequence is used such as a T7 site, the RNA polymerase is added and copies of the adapter sequence are generated. Alternatively, when the amplification reaction is PCR, two primers are added, each of which is substantially complementary (and preferably perfectly complementary) to one of the universal priming sequences or its complement. Again, as outlined more fully below, there may be more than one set of universal priming sequences/primers used in a given reaction. In addition, as will be appreciated by those in the art, a number of other amplification reactions can be done, as outlined below.

In an alternative embodiment, the "Universal" primer sequences are designed not to solely serve as PCR primers, but also as a promoter sequence for RNA Polymerase. Thus, the annealed (and/or ligated) target probes can be amplified not only by general PCR, but can also be amplified by in vitro transcription (IVT). The linear amplification produced by IVT should be better at maintaining the relative amounts of the different sequences in the initial template population than the exponential amplification of PCR.

The resulting amplicons can be detected in a wide variety of ways, including the use of biochips (e.g. solid support arrays, including both ordered and random arrays, as outlined herein) liquid arrays, capillary electrophoresis, mass spectroscopy analysis, etc., in a variety of formats, including sandwich assays, as is further described herein.

In some cases, one or more of the target analytes or probes may be attached to a solid support. For example, the target analytes (for example, genomic DNA sequences) can be attached to beads in a variety of ways. The probe pool is added to form assay complexes (sometimes referred to herein as hybridization complexes when the target analytes are nucleic acids) and unhybridized probes are washed away. The probes are denatured off the target analytes, and then amplified as outlined herein.

Alternatively, solution phase assays may be done, followed by either liquid or solid array detection.

Accordingly, the present invention relates to the multiplex amplification and detection of methylated target nucleic acids in a sample. As used herein, the phrase "multiplex" or grammatical equivalents refers to the detection, analysis or amplification of more than one target nucleic acid of interest. In a one embodiment, multiplex refers to at least 100 different target nucleic acids while at least 500 different target nucleic acids is preferred. More preferred is at least 1000, with more than 5000 particularly preferred and more than 10,000 most preferred. Detection is performed on a variety of platforms. In a preferred embodiment the invention is utilized with adapter sequences that identify the target molecule.

In addition, the present invention provides compositions and methods for detecting methylated target nucleic acids including detecting and quantitating specific, methylated target nucleic acid sequences in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred). The sample may comprise individual cells, including primary cells (including bacteria), and cell lines, including, but not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, 923, HeLa, WI-38, Weri-1, MG-63, etc. See the ATCC cell line catalog, hereby expressly incorporated by reference.

If required, the target analyte is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In addition, when nucleic acids are to be detected preferred methods utilize cutting or shearing techniques to cut the nucleic acid sample containing the target sequence into a size that will facilitate handling and hybridization to the target, particularly for genomic DNA samples. This may be accomplished by shearing the nucleic acid through mechanical forces (e.g. sonication) or by cleaving the nucleic acid using restriction endonucleases.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques may also be used.

In one preferred embodiment the target nucleic acids have been prepared as described below to detect the presence or absence of methylation at various loci.

In a preferred embodiment, the compositions and methods of the invention are directed to the detection of target sequences. By "nucleic acid" or "oligonucleotide" or grammatical equivalents herein means at least two nucleotides covalently linked together. A nucleic acid of the present invention will generally contain phosphodiester bonds, although in some cases, as outlined below, particularly for use with probes or primers, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 13:805-808 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of labels, or to increase the stability and half-life of such molecules in physiological environments.

In a preferred embodiment, the nucleic acid preferably includes at least one universal base. Universal bases are those that can substitute for any of the five natural bases, that is, universal bases will basepair with all natural bases, preferably equally well. Suitable universal bases include, but are not limited to, inosine, hypoxanthine, 5'nitroindole, acylic 5"nitroindole, 4'nitropyrazole, 4'nitroimidazole and 3'nitropyrrole. See Loakes et al., Nucleic Acid Res. 22:4039 (1994); Van Aerschot et al., Nucleic Acid Res. 23:4363 (1995); Nichols et al., Nature 369:492 (1994); Berstrom et al., Nucleic Acid Res. 25:1935 (1997); Loakes et al., Nucleic Acid Res. 23:2361 (1995); Loakes et al., J. Mol. Biol. 270: 426 (1997); and Fotin et al., Nucleic Acid Res. 26:1515 (1998); and references cited therein, all of which are expressly incorporated by reference.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. Thus, for example, when the target sequence is a polyadenylated mRNA, the hybridization complex comprising the target probe has a double stranded portion, where the target probe is hybridized, and one or more single stranded portions, including the poly (A) portion. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide, nucleic acid, each containing a base, are referred to herein as a nucleoside.

Preferably the target sequence is potentially a methylated target sequence. Generally "methylated" includes any nucleotide that is methylated. Frequently methylated refers to nucleic acids that include 5-methylcytosine, but the term also can be used in the context of an enzyme that discriminately cleaves at the site of sequences that are targets for methylation, referred to interchangeably as "methylated target sequences" or "methylation target sequences." The term "target sequence" or "target nucleic acid" or grammatical equivalents herein means a nucleic acid sequence on a single strand of nucleic acid. The target sequence may be a portion of a gene, a regulatory sequence, genomic DNA (gDNA), cDNA, RNA including mRNA and rRNA, or others, with potentially methylated genomic DNA being particular preferred in some embodiments. As described above, the term "methylated target sequence" when used in reference to an enzyme that discriminately cleaves at the site of the target sequence refers to target sequences for methylation, regardless of methylation status, and are interchangeably referred to as "methylation target sequences." Typically, the discrimination is based on methylation blocking restriction such that methylation target sequences in non-methylated state are discriminately cleaved by the enzyme.

As is outlined herein, the target sequence may be a target sequence from a sample, or a secondary target such as an amplicon, which is the product of an amplification reaction such as PCR or an RNA polymerase reaction, although generally the target sequence will be from a sample.

The target sequence may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. Particularly preferred target sequences in the present invention include genomic DNA, polyadenylated mRNA, and alternatively spliced RNAs. As is outlined more fully below, probes are made to hybridize to target sequences to determine the presence, absence, quantity or sequence of a target sequence in a sample. Generally speaking, this term will be understood by those skilled in the art.

The target sequence may also be comprised of different target domains, that may be adjacent (i.e. contiguous) or separated. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. In addition, as will be appreciated by those in the art, the probes on the surface of the array (e.g. attached to the microspheres) may be attached in either orientation, either such that they have a free 3' end or a free 5' end; in some embodiments, the probes can be attached at one or more internal positions, or at both ends.

In a preferred embodiment the invention is directed to target sequences that comprise one or more positions for which sequence information is desired, generally referred to herein as the "detection position" or "detection locus". In a preferred embodiment, the detection position is a single nucleotide, generally a cytosine that may, at times, be methylated, although in some embodiments, it may comprise either other single nucleotides or a plurality of nucleotides, either contiguous with each other or separated by one or more nucleotides. By "plurality" as used herein is meant at least two. As used herein, the base of a probe (e.g. the target probe) which basepairs with a detection position base, in a hybrid is termed a "readout position" or an "interrogation position". Thus, the target sequence comprises a detection position and the target probe comprises a readout position.

In a preferred embodiment, the use of competitive hybridization target probes is done to elucidate either the identity of the nucleotide(s) at the detection position or the presence of a mismatch.

It should be noted in this context that "mismatch" is a relative term and meant to indicate a difference in the identity of a base at a particular position, termed the "detection position" herein, between two sequences. In general, sequences that differ from wild type sequences are referred to as mismatches. In the case of SNPs, what constitutes "wild type" may be difficult to determine as multiple alleles can be relatively frequently observed in the population, and thus "mismatch" in this context requires the artificial adoption of one sequence as a standard. When determining methylation patterns, the sequence of the target prior to any modification as set forth herein constitutes "wild type" while the sequence subsequent to any methylation selective modification constitutes a "mismatch". Thus, for the purposes of this invention, sequences are referred to herein as "match" and "mismatch". Thus, while the present invention may be used to detect substitutions, insertions or deletions as compared to a wild-type sequence, preferably the invention is used to detect methylation of target nucleic acids. That is, all other parameters being equal, a perfectly complementary readout target probe (a "match probe") will in general be more stable and have a slower off rate than a target probe comprising a mismatch (a "mismatch probe") at any particular temperature.

In a preferred embodiment the target nucleic acids are modified in a methylation selective manner either prior to or after immobilization of the target nucleic acids as described below. That is, DNA methylation analysis methods generally rely on a methylation-dependent modification of the original genomic DNA before any amplification step. The methods are outlined generally below.

Methylation-Specific Enzymes

In one embodiment a method of methylation detection assays includes digesting genomic DNA with a methylation-sensitive restriction enzyme followed by detection of the differentially cleaved DNA, e.g. by Southern blot analysis (Issa, J. P., Ottaviano, Y. L., Celano, P., Hamilton, S. R., Davidson, N. E. and Daylin, S. B. (1994) Methylation of the oestrogen receptor CpG island links ageing and neoplasia in human colon. Nat Genet, 7, 536-540.; Taylor, J. M., Kay, P. H. and Spagnolo, D. V. (2001) The diagnositc significance of Myf-3 hypermethylation in malignant lymphoproliferative disorders. Leukemia, 15, 583-589) or PCR (Singer-Sam, J., LeBon, J. M., Tanguay, R. L. and Riggs, A. D. (1990) A quantitative HpaII-PCR assay to measure methylation of DNA from a small number of cells. Nucleic Acids Res, 18, 687), or methods as described below. In a preferred embodiment the methylation specific enzyme is HpaII which recognizes 5'-CCGG-3'. The digestion is blocked by methylation at either C. Also, the methylation specific enzyme Msp I finds use in the invention.

Bisulfite DNA Sequencing

In a preferred embodiment, the method is based on the selective deamination of cytosine to uracil by treatment with bisulfite and the sequencing of subsequently generated PCR products. The method utilizes bisulfite-induced modification of genomic DNA, under conditions whereby cytosine is converted to uracil, but 5-methylcytosine remains non-reactive. The sequence under investigation is then analyzed by any of the methods as described below including without limitation, being amplified by PCR with two sets of strand-specific primers to yield a pair of fragments, one from each strand, in which all uracil and thymine residues have been amplified as thymine and only 5-methylcytosine residues have been amplified as cytosine. The PCR products can be detected as described below or sequenced directly to provide a strand-specific average sequence for the population of molecules or can be cloned and sequenced to provide methylation maps of single DNA molecules (Feil, R., Charlton, J., Bird, A. P., Walter, J. and Reik, W. (1994) Methylation analysis on individual chromosomes: improved protocol for bisulphite genomic sequencing. Nucleic Acids Res, 22, 695-696; Frommer, M., McDonald, L. E., Millar, D. S., Collis, C. M., Watt, F., Grigg, G. W., Molloy, P. L. and Paul, C. L. (1992) A genomic sequencing protocol that yields a positive display of 5-methylcytosine residues in individual DNA strands. Proc Natl Acad Sci USA, 89, 1827-1831). Exact methylation maps of single DNA strands from individual genomic DNA molecules can be established, where the position of each 5-methylcytosine is given by a clear positive band on a sequencing gel.

Methylation-Specific PCR (MSP)

In an alternative embodiment the method includes an initial modification of DNA by sodium bisulfite, and subsequent detection and amplification with primers specific for methylated versus unmethylated DNA (Herman, J. G., Graff, J. R., Myohanen, S., Nelkin, B. D. and Baylin, S. B. (1996) Methylation-specific PCR: a novel PCR assay for methylation status of CpG islands. Proc Natl Acad Sci USA, 93, 9821-9826.) and as described in more detail below. The method can rapidly assess the methylation status of virtually any group of CpG sites within a CpG island, and does not require the use of methylation-sensitive restriction enzymes. MSP requires only small quantities of DNA, is sensitive to 0.1% methylated alleles of a given CpG island locus, and can be performed on DNA extracted from paraffin-embedded samples. Unmodified DNA or DNA incompletely reacted with bisulfite can be distinguished, since marked sequence differences exist between these DNAs. Simultaneous detection of unmethylated and methylated products in a single sample allows a semi-quantitative assessment of allele types that approximates the quantitation determined by Southern analysis. The ability to validate the amplified product by differential restriction patterns is an additional advantage.

Methylation-Sensitive Single Nucleotide Primer Extension (MS-SnuPE)

In an alternative embodiment the method includes treating genomic DNAs with bisulfite and the target sequences are amplified with PCR primers specific for the converted DNA. The resulting PCR products are then used as a template for the MS-SnuPE reaction, in the presence of specific extension primers and dye-labeled or radioactive dCTP or dTTP. The extension primers are designed in such that their 3'-landing sites are just one base before the incorporation site designated for methylation analysis. If the target site is methylated, a C will be incorporated during the primer extension, or a T will be incorporated if the target site is unmethylated. Quantitation of the relative C and T incorporation will allow the determination of the methylation status of the target site. A complete bisulfite-mediated DNA conversion is important for an accurate measurement (of methylation) with this approach. This method finds use in quantitation of methylation difference at specific CpG sites (Gonzalgo, M. L. and Jones, P. A. (1997) Rapid quantitation of methylation differences at specific sites using methylation-sensitive single nucleotide primer extension (Ms-SNuPE). Nucleic Acids Res, 25, 2529-2531; Kuppuswamy, M. N., Hoffmann, J. W., Kasper, C. K., Spitzer, S. G., Groce, S. L. and Bajaj, S. P. (1991) Single nucleotide primer extension to detect genetic diseases: experimental application to hemophilia B (factor IX) and cystic fibrosis genes. Proc Natl Acad Sci USA, 88, 1143-1147).

Other methods such as Restriction landmark genomic scanning (RLGS) (Akama, T. O., Okazaki, Y., Ito, M., Okuizumi, H., Konno, H., Muramatsu, M., Plass, C., Held, W. A. and Hayashizaki, Y. (1997) Restriction landmark genomic scanning (RLGS-M)-based genome-wide scanning of mouse liver tumors for alterations in DNA methylation status. Cancer Res, 57, 3294-3299.; Kawai, J., Hirose, K., Fushiki, S., Hirotsune, S., Ozawa, N., Hara, A., Hayashizaki, Y. and Watanabe, S. (1994) Comparison of DNA methylation patterns among mouse cell lines by restriction landmark genomic scanning. Mol Cell Biol, 14, 7421-7427) and differential methylation hybridization (DMH) (Huang, T. H., Perry, M. R. and Laux, D. E. (1999) Methylation profiling of CpG islands in human breast cancer cells. Hum Mol Genet, 8, 459-470) also find use in the invention. All references are expressly incorporated herein by reference.

In addition to the methods described above as useful to assess or measure the methylation status at a given site in a genomic DNA, for example, bisulfite sequencing and methylation-specific PCR, the invention provides a calibration curve for the quantitative methylation measurement of an unknown sample derived from a reference organism. The calibration curve of the invention can be prepared by providing and amplifying a first reference genomic DNA, for example, at least one hundred fold, one thousand fold, ten thousand fold, or more, wherein the ratio of methylated to unmethylated sequences is decreased sufficiently to prepare a virtually unmethylated template population, obtaining a methylated template population having nucleotide sequences corresponding to the nucleotide sequences of the reference genomic DNA, separately mixing fixed amounts of the virtually unmethylated template population with fixed amounts of the methylated template population at various distinct ratios to create a series of mixtures that represents a methylation gradient, thereby generating a calibration reagent for quantitative methylation measurement of an unknown sample of the reference organism. The methylated template population can be obtained by methylating the reference genomic DNA. If desired the methylated template population can be obtained by methylating a portion removed from the virtually unmethylated sample. Nucleic acid samples can be methylated using an enzyme biological sample, or fraction thereof having DNA methylation activity such as those described herein or known in the art.

The invention thus provides a calibration curve that allows quantitatively calibrate any genomic DNA methylation measurement, regardless of the methylation detection system that is utilized A calibration curve of the invention can be prepared by the method described above. The invention also provides a calibration curve comprising a first axis indicating the amount of unmethylated template population compared to methylated template population and a second axis indicating a detected methylation signal. A detected methylation signal can be any signal that corresponds to presence of a methylated target nucleic acid including, for example, signals obtained in methods described herein. A calibration curve of the invention can be presented in a variety of known formats including, without limitation, a hardcopy, graphical user interface of a computer, computer readable memory such as a magnetic disk, compact disc, random access memory or the like.

A calibration curve of the invention can be used to determine the extent of methylation for a sample under investigation. For example, a methylation signal can be measured for a sample using methods described herein. The intensity of the signal can be compared to a calibration curve of the invention such that the extent of methylation corresponding to the signal intensity is determined.

As used herein, the term "reference genomic DNA" refers to a DNA derived from the same individual organism as a sample to which it is compared.

The term "virtually unmethylated" used in reference to a first reference genomic DNA refers to the absence of methyl containing bases or presence of an amount of methyl containing bases that is negligible in routine detection methods. The term can refer to a dilution of methylated sequences by multiple rounds of amplification to create a sufficiently small ratio of methylated to unmethylated sequences that the methylated sequences are rendered undetectable by routine detection methods. A sample having, for example, less than 1%, 0.05%, or 0.01% methyl containing bases can be considered to be virtually unmethylated.

In particular embodiments a virtually unmethylated template population can be used to determine the limit of detection for a sample. In this regard, signal detected from a virtually unmethylated template population provides a negative control, such that signals derived therefrom can be considered to constitute the lower limit of detection and signals having higher intensity than those measured for the virtually unmethylated template population are detectable and significant.

In some embodiments, as outlined below, the target sequences (or target probes, in some instances) may be attached to a solid support prior to contact with the target probes (or to remove unhybridized target probes, etc.). In this embodiment, the target sequence may comprise a purification tag. By "purification tag" herein is meant a moiety which can be used to purify a strand of nucleic acid, usually via attachment to a solid support as outlined herein. Suitable purification tags include members of binding partner pairs. For example, the tag may be a hapten or antigen, which will bind its binding partner. In a preferred embodiment, the binding partner can be attached to a solid support as depicted herein and in the figures. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid— nucleic acid binding proteins pairs are also useful. In general, the smaller of the pair is attached to the NTP for incorporation into the primer. Preferred binding partner pairs include, but are not limited to, biotin (or imino-biotin) and streptavidin, digoxygenin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

The present invention provides methods and compositions directed to the multiplex amplification and detection of methylated target sequences utilizing target probes.

Accordingly, the invention provides a number of different primers and probes. The probes and primers are nucleic acid as defined above.

Many of the probes and primers of the present invention are designed to have at least a portion that binds substantially specifically to a target nucleic acid (sometimes referred to herein as a bioactive agent (particularly in the case wherein the target analyte is not a nucleic acid) or a target specific portion). That is the probes are constructed so as to contain a target specific portion: a portion that binds to the target nucleic acid specifically, i.e. with high affinity. This target specific portion can be any type of molecule so long as it specifically binds the target and can be attached to the rest of a target probe, namely a nucleic acid sequence that preferably includes an adapter sequence and at least one priming sequence.

In a preferred embodiment, the binding of the bioactive agent and the target nucleic acid is specific; that is, the bioactive agent specifically binds to the target nucleic acid. By "specifically bind" herein is meant that the agent binds the target nucleic acid, with specificity sufficient to differentiate between the target and other components or contaminants of the test sample.

When nucleic acids are the target, the probes are designed to be complementary to all or a portion (domain) of a target sequence (either the target sequence of the sample or to other probe sequences, such as portions of amplicons, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the bioactive agent portion of the probes are sufficiently complementary to all or part of the target sequences to hybridize under normal reaction conditions, and preferably give the required specificity. In a preferred embodiment the probes have a portion that is exactly complementary to the target nucleic acids.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

In a preferred embodiment, the target probes further comprise one or more "adapter sequences" (sometimes referred to in the art as "zip codes") to allow the use of "universal arrays". That is, arrays are generated that contain capture probes that are not target specific, but rather specific to individual artificial adapter sequences. The adapter sequences are added to the target probes, nested between the priming sequences (when two priming sequences are used) or "downstream" of a single universal priming sequence, and thus are included in the amplicons. What is important is that the orientation of the priming sequence and the adapter sequence allows the amplification of the adapter sequence.

An "adapter sequence" is a sequence, generally exogeneous to the target sequences, e.g. artificial, that is designed to be substantially complementary (and preferably perfectly complementary) to a capture probe of a detection array. Generally the capture probe is immobilized to a solid support that can include microspheres or planar substrates such as plastic or glass slides as described herein for array supports. In one embodiment the use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The adapter sequences can then be incorporated in the target probes.

As will be appreciated by those in the art, the length of the adapter sequences will vary, depending on the desired "strength" of binding and the number of different adapters desired. In a preferred embodiment, adapter sequences range from about 6 to about 500 basepairs in length, with from about 8 to about 100 being preferred, and from about 10 to about 25 being particularly preferred.

In a preferred embodiment, the adapter sequence uniquely identifies the target analyte to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target analyte.

In one embodiment the adapter includes both an identifier region and a region that is complementary to capture probes on a universal array as described above. In this embodiment, the amplicon hybridizes to capture probes on a universal array. Detection of the adapter is accomplished following hybridization with a probe that is complementary to the adapter sequence. Preferably the probe is labeled as described herein.

In general, unique adapter sequences are used for each unique target analyte. That is, the elucidation or detection of a particular adapter sequence allows the identification of the target analyte to which the target probe containing that adapter sequence bound. However, in some cases, it is possible to "reuse" adapter sequences and have more than one target analyte share an adapter sequence.

In a preferred embodiment the adapters contain different sequences or properties that are indicative of a particular target molecule. That is, each adapter uniquely identifies a target analyte. As described above, the adapters are amplified to form amplicons. The adapter is detected as an indication of the presence of the target analyte.

The use of adapters in combination with amplification following a specific binding event allows for highly multiplexed reactions to be performed.

Also, the probes are constructed so as to contain the necessary priming site or sites for the subsequent amplification scheme. In a preferred embodiment the priming sites are universal priming sites. By "universal priming site" or "universal priming sequences" herein is meant a sequence of the probe that will bind a primer for amplification.

In a preferred embodiment, one universal priming sequence or site is used. In this embodiment, a preferred universal priming sequence is the RNA polymerase T7 sequence, that allows the T7 RNA polymerase make RNA copies of the adapter sequence as outlined below.

In a preferred embodiment, for example when amplification methods requiring two primers such as PCR are used, each probe preferably comprises an upstream universal priming site (UUP) and a downstream universal priming site (DUP). Again, "upstream" and "downstream" are not meant to convey a particular 5'-3' orientation, and will depend on the orientation of the system. Preferably, only a single UUP sequence and a single DUP sequence is used in a probe set, although as will be appreciated by those in the art, different assays or different multiplexing analysis may utilize a plurality of universal priming sequences. In addition, the universal priming sites are preferably located at the 5' and 3' termini of the target probe (or the ligated probe), as only sequences flanked by priming sequences will be amplified.

In addition, universal priming sequences are generally chosen to be as unique as possible given the particular assays and host genomes to ensure specificity of the assay. However, as will be appreciated by those in the art, sets of priming sequences/primers may be used; that is, one reaction may utilize 500 target probes with a first priming sequence or set of sequences, and an additional 500 probes with a second sequence or set of sequences.

As will be appreciated by those in the art, when two priming sequences are used, the orientation of the two priming sites is different. That is, one PCR primer will directly hybridize to the first priming site, while the other PCR primer will hybridize to the complement of the second priming site. Stated differently, the first priming site is in sense orientation, and the second priming site is in antisense orientation.

The size of the primer and probe nucleic acid may vary, as will be appreciated by those in the art with each portion of the probe and the total length of the probe in general varying from 5 to 500 nucleotides in length. Each portion is preferably between 10 and 100 being preferred, between 15 and 50 being particularly preferred, and from 10 to 35 being especially preferred, depending on the use and amplification technique. Thus, for example, the universal priming site(s) of the probes are each preferably about 15-20 nucleotides in length, with 18 being especially preferred. The adapter sequences of the probes are preferably from 15-25 nucleotides in length, with 20 being especially preferred. The target specific portion of the probe is preferably from 15-50 nucleotides in length. In addition, the primer may include an additional amplification priming site. In a preferred embodiment the additional amplification priming site is a T7 RNA polymerase priming site.

Accordingly, the present invention provides first target probe sets. By "probe set" herein is meant a plurality of target probes that are used in a particular multiplexed assay. In this context, plurality means at least two, with more than 10 being preferred, depending on the assay, sample and purpose of the test. In one embodiment the probe set includes more than 100, with more than 500 probes being preferred and more than 1000 being particularly preferred. In a particularly preferred embodiment each probe contains at least 5000, with more than 10,000 probes being most preferred.

Accordingly, the present invention provides first target probe sets that comprise at least a first universal priming site.

In a preferred embodiment, the target probe may also comprise a label sequence, i.e. a sequence that can be used to bind label probes and is substantially complementary to a label probe. This is sometimes referred to in the art as "sandwich-type" assays. That is, by incorporating a label sequence into the target probe, which is then amplified and present in the amplicons, a label probe comprising primary (or secondary) labels can be added to the mixture, either before addition to the array or after. This allows the use of high concentrations of label probes for efficient hybridization. In one embodiment, it is possible to use the same label sequence and label probe for all target probes on an array; alternatively, different target probes can have a different label sequence. Similarly, the use of different label sequences can facilitate quality control; for example, one label sequence (and one color) can be used for one strand of the target, and a different label sequence (with a different color) for the other; only if both colors are present at the same basic level is a positive called.

Thus, the present invention provides target probes that comprise universal priming sequences, bioactive agents (e.g. target specific portion(s)), adapter sequence(s), optionally an additional amplification priming sequence such as T7 RNA priming sequence and optionally label sequences. These target probes are then added to the target sequences to form hybridization complexes. As will be appreciated by those in the art, when nucleic acids are the target, the hybridization complexes contain portions that are double stranded (the target-specific sequences of the target probes hybridized to a portion of the target sequence) and portions that are single stranded (the ends of the target probes comprising the universal priming sequences and the adapter sequences, and any unhybridized portion of the target sequence, such as poly(A) tails, as outlined herein).

As will be appreciated by those in the art, the systems of the invention can take on a wide variety of configurations, including systems that rely on the initial immobilization of the target analyte (solid phase assays) and solution based assays.

Solid Phase Assays

In a preferred embodiment, the target analyte is immobilized on the surface. That is, the target nucleic acids or target sequences are immobilized on a substrate or capture surface. Attachment may be performed in a variety of ways, as will be appreciated by those in the art, including, but not limited to, chemical or affinity capture (for example, including the incorporation attachment moieties such as derivatized nucleotides such as AminoLink™ or biotinylated nucleotides that can then be used to attach the nucleic acid to a surface, as well as affinity capture by hybridization), cross-linking, and electrostatic attachment, etc. When the target analyte is polyadenylated mRNA, supports comprising poly(T) sequences can be used. That is, an attachment moiety is attached to the target analyte that allows for attachment to the substrate. By "attachment moiety" is meant a molecule or substance that mediates attachment of the target analyte to the substrate. In a preferred embodiment, affinity capture is used to attach the nucleic acids to the support. For example, nucleic acids can be derivatized, for example with one member of a binding pair, and the support derivatized with the other member, i.e. a complementary member, of a binding pair. For example, the nucleic acids may be biotinylated (for example using enzymatic incorporation of biotinylated nucleotides, or by photoactivated cross-linking of biotin). In a preferred embodiment the target nucleic acids are photobiotinylated In one preferred embodiment the target nucleic acids are photobiotinylated with PHOTOPROBE™ Biotin Reagents (Vector Laboratories). Biotinylated nucleic acids can then be captured on streptavidin-coated surfaces, as is known in the art. In one embodiment the surfaces or supports are beads to which the nucleic acids are attached, although other solid supports as defined herein may also be used, e.g. microtiter plates. In a particularly preferred embodiment the beads are magnetic beads. Similarly, other hapten-receptor combinations can be used, such as digoxigenin and anti-digoxigenin antibodies. Alternatively, chemical groups can be added in the form of derivatized nucleotides, that can then be used to add the nucleic acid to the surface.

Similarly, affinity capture utilizing hybridization can be used to attach nucleic acids to surface or bead. For example, a poly-A tract can be attached by polymerization with terminal transferase, or via ligation of an oligo-A linker, as is known in the art. This then allows for hybridization with an immobilized poly-T tract. Alternatively, chemical crosslinking may be done, for example by photoactivated crosslinking of thymidine to reactive groups, as is known in the art.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

A preferred embodiment utilizes covalent attachment of the target sequences to a support. As is known in the art, there are a wide variety of methods used to covalently attach nucleic acids to surfaces. A preferred embodiment utilizes the incorporation of a chemical functional group into the nucleic acid, followed by reaction with a derivatized or activated surface. Examples include, but are not limited to Amino-Link™.

By "capture surface", "target substrate" or "target support" or other grammatical equivalents herein is meant any material to which a target analyte can be attached. The targets can be attached either directly or indirectly as described herein. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, and a variety of other polymers. Preferably the substrates include microfuge tubes, i.e. Eppendorf tubes. In one embodiment the substrates include beads or microspheres. In one embodiment the beads or microspheres are magnetic, particularly for the capture of gDNA. In one embodiment the substrates are derivatized to accommodate attachment of the target nucleic acids to the substrate.

The configuration of the target support is not crucial. What is important is that the target analytes are immobilized to the target support and can be manipulated. That is, the support should be amenable to a variety of reactions as described herein. While the target substrate can be flat (planar), other configurations of substrates may be used as well; for example, target analytes can be attached to beads or microspheres that can be deposited in reaction tubes or vessels or wells. That is, the target substrate may be microspheres to which the target analytes are attached. The microspheres can then be distributed on a surface. In some embodiments the surface contains reaction wells into which the beads are distributed, for example microtiter plates as are known in the art and as described herein.

Once the target analytes, i.e. genomic DNA or proteins, are applied to or immobilized on the surface, the target analytes are contacted with probes for analyses, including detection or genotyping. That is, the appropriate probes necessary for detection of the target analyte or for the methylation detection reactions are next introduced to the immobilized sample.

For the assays described herein, the assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

Following binding or hybridization of the bioactive agent portion of the target probe to the target analyte, unhybridized probes are removed by a washing step. In a preferred embodiment the wash step is a stringent wash step. That is, in the preferred embodiment of an enzymatic based mutation detection reaction, once the probes have been introduced under conditions to favor hybridization with the appropriate nucleic acid sequences, a stringent wash step is conducted. This wash removes unhybridized probes and reduces the overall complexity of the mixture. It is this step that ensures the success of the overall multiplexed reaction.

As will be appreciated by those in the art, there are a wide variety of detection reactions that can be performed at this stage depending on the goal of the assay. In a preferred embodiment, different target probes are made that span the region of the potentially methylated nucleotide. That is, target probes are designed to hybridize with a region spanning the methylation position. If the target is cleaved, the methylation position will be absent and the probe will not hybridize as efficiently as it will with the uncleaved target. The wash step is done under conditions to wash away probes that hybridize to the cleaved target Thus, hybridization is indicative of uncleaved targets. Target probes can be applied to the target as one probe spanning the region of the methylated nucleotide or they may be the product of a modification of the probe, e.g. as a result of ligation or polymerase extension as described herein.

In a preferred embodiment, when bisulfite is used as described above to detect methylation of the target nucleic acid, probes are designed to hybridize with either the "C" at the detection position or "U" at the detection position. The presence of C indicates that the target was methylated and thus not converted to U upon incubation with bisulfite.

In a preferred embodiment when nucleic acids are the target, a plurality of target probes (sometimes referred to herein as "readout target probes") are used to identify the base at the detection position. In this embodiment, each different readout probe comprises a different base at the position that will hybridize to the detection position of the target sequence (herein referred to as the readout or interrogation position) and a different adapter sequence for each different readout position. In this way, differential hybridization of the readout target probes, depending on the sequence of the target, results in identification of the base at the detection position. In this embodiment, the readout probes are contacted with the array again under conditions that allow discrimination between match and mismatch, and the unhybridized probes are removed, etc.

Accordingly, by using different readout target probes, each with a different base at the readout position and each with a different adapter, the identification of the base at the detection position is elucidated. Thus, in a preferred embodiment, a set of readout probes are used, each comprising a different base at the readout position.

In a preferred embodiment, each readout target probe has a different adapter sequence. That is, readout target probes comprising adenine at the readout position will have a first adapter, probes with guanine at the readout position will have a second adapter, etc., such that each target probe that hybridizes to the target sequence will bind to a different address on the array. This can allow the use of the same label for each reaction.

The number of readout target probes used will vary depending on the end use of the assay.

In this embodiment, sensitivity to variations in stringency parameters are used to determine either the identity of the nucleotide(s) at the detection position or the presence of a mismatch. As a preliminary matter, the use of different stringency conditions such as variations in temperature and buffer composition to determine the presence or absence of mismatches in double stranded hybrids comprising a single stranded target sequence and a probe is well known.

With particular regard to temperature, as is known in the art, differences in the number of hydrogen bonds as a function of basepairing between perfect matches and mismatches can be exploited as a result of their different Tms (the temperature at which 50% of the hybrid is denatured). Accordingly, a hybrid comprising perfect complementarity will melt at a higher temperature than one comprising at least one mismatch, all other parameters being equal. (It should be noted that for the purposes of the discussion herein, all other parameters (i.e. length of the hybrid, nature of the backbone (i.e. naturally occurring or nucleic acid analog), the assay solution composition and the composition of the bases, including G-C content are kept constant). However, as will be appreciated by those in the art, these factors may be varied as well, and then taken into account.)

In general, as outlined herein, high stringency conditions are those that result in perfect matches remaining in hybridization complexes, while imperfect matches melt off. Similarly, low stringency conditions are those that allow the formation of hybridization complexes with both perfect and imperfect matches. High stringency conditions are known in the art as outlined above.

As will be appreciated by those in the art, mismatch detection using temperature may proceed in a variety of ways.

Similarly, variations in buffer composition may be used to elucidate the presence or absence of a mismatch at the detection position. Suitable conditions include, but are not limited to, formamide concentration. Thus, for example, "low" or "permissive" stringency conditions include formamide concentrations of 0 to 10%, while "high" or "stringent" conditions utilize formamide concentrations of $\geqq 40\%$. Low stringency conditions include NaCl concentrations of $\geqq 1$ M, and high stringency conditions include concentrations of $\leqq 0.3$ M. Furthermore, low stringency conditions include $MgCl_2$ concentrations of $\geqq 10$ mM, moderate stringency as 1-10 mM, and high stringency conditions include concentrations of $\leqq 1$ mM.

In this embodiment, as for temperature, a plurality of readout probes may be used, with different bases in the readout position and different adapters. Running the assays under the permissive conditions and repeating under stringent conditions will allow the elucidation of the base at the detection position.

Thus, the washing is performed under stringency conditions which allows formation of the first hybridization complex only between probes and complementary target sequences. As outlined above, stringency can be controlled by altering a step parameter that is a thermodynamic variable, including, but not limited to, temperature, formamide concentration, salt concentration, chaotropic salt concentration, pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

In a preferred embodiment, the target sequence may be immobilized after the formation of the hybridization complexes, ligation complexes and/or ligated complexes. That is, the probes can be added to the targets in solution, enzymes added as needed, etc. After the hybridization complexes are formed and/or ligated, the hybridization complexes can be added to supports comprising the binding partners and the unhybridized probes removed.

In this embodiment, particularly preferred binding ligand/binding partner pairs are biotin and streptavidin or avidin, antigens and antibodies.

As described above, once the hybridization complexes are formed, unhybridized probes are removed. This is important to increase the level of multiplexing in the assay. In addition, as all target probes may form some unpredictable structures that will complicate the amplification using the universal priming sequences. Thus to ensure specificity (e.g. that target probes directed to target sequences that are not present in the sample are not amplified and detected), it is important to remove all the nonhybridized probes. As will be appreciated by those in the art, this may be done in a variety of ways, including methods based on the target sequence, methods utilizing double stranded specific moieties, and methods based on probe design and content. Preferably the method includes a stringent wash step.

Once the non-hybridized probes (and additionally, if preferred, other sequences from the sample that are not of interest) are removed, the hybridization complexes are denatured and the target probes are amplified to form amplicons, which are then detected. This can be done in one of several ways as outlined below. In addition, as outlined below, labels can be incorporated into the amplicons in a variety of ways.

Accordingly, this embodiment can be run in several modes. In a preferred embodiment, only a single probe is used, comprising (as outlined herein), at least a first UUP, an adapter sequence, and a target-specific portion, i.e. a target specific moiety or bioactive agent. When nucleotides are the target molecule the target-specific portion includes nucleic acids comprising a first base at the readout position, and in some embodiments a DUP. This probe is contacted with the target analyte under conditions (whether thermal or otherwise) such that specific binding occurs. In a preferred embodiment, when nucleic acids are the target, a hybridization complex is formed only when a perfect match between the detection position of the target and the readout position of the probe is present. The non-hybridized or non-bound probes are then removed as outlined herein. That is, after the wash step, only the properly hybridized probes should remain. In one embodiment when nucleic acids are the target, the hybridized probes must then be separated from the captured sample nucleic acid. This is done via a stringent wash step or denaturation step. The sample nucleic acid is left behind on the capture surface, and can be used again. In an alternative embodiment, although not preferred, the hybridized probe is not removed. it is not necessary to remove the probes when the priming sites and adapter sequences do not hybridize with the target. The probe is then amplified as outlined herein, and detected. In a preferred embodiment the amplified product(s), i.e. amplicons, are detected as an indication of the presence of the target analyte.

As noted above, the target sequence may be immobilized either before or after the formation of the hybridization complex, but preferably it is immobilized on a surface or support comprising the binding partner of the binding ligand prior to the formation of the hybridization complex with the probe(s) of the invention. For example, a preferred embodiment utilizes binding partner coated reaction vessels such as eppendorf tubes or microtiter wells. Alternatively, the support may be in the form of beads, including magnetic beads. In this embodiment, the primary target sequences are immobilized, the target probes are added to form hybridization complexes. Unhybridized probes are then removed through washing steps, and the bound probes (e.g. either target probes, ligated probes, or ligated RCA probes) are then eluted off the support, usually through the use of elevated temperature or buffer conditions (pH, salt, etc.).

Once the non-hybridized probes (and additionally, if preferred, other sequences from the sample that are not of interest) are removed, the hybridization complexes are denatured and the target probes are amplified to form amplicons, which are then detected. This can be done in one of several ways, including PCR amplification and rolling circle amplification. Also, the probes can be amplified by known methods (exponential or linear amplification techniques such as PCR, Invader, ESPIA (also known as SPIA), T7), using the one or more priming sites provided on the probes. As noted herein, the probes are constructed so as to contain the necessary primer sites to permit this amplification. In a preferred embodiment, universal primers are used. Amplification provides the signal strength and dynamic range necessary for detection of the mutation-detection probes. In addition, as outlined below, labels can be incorporated into the amplicons in a variety of ways.

In a preferred embodiment, no ligation assay for genotyping is done, that is, no ligase is added. However, as will be appreciated by those in the art, ligation reactions for other purposes may be done.

In a preferred embodiment, a linear amplification scheme known as ESPIA, or SPIA is applied. This amplification technique is disclosed in WO 01/20035 A2 and U.S. Pat. No. 6,251,639, which are incorporated by reference herein. Generally, the method includes hybridizing chimeric RNA/DNA amplification primers to the probes. Preferably the DNA portion of the probe is 3' to the RNA. Optionally the method includes hybridizing a polynucleotide comprising a termination polynucleotide sequence to a region of the template that is 5' with respect to hybridization of the composite primer to the template. Following hybridization of the primer to the template, the primer is extended with DNA polymerase. Subsequently, the RNA is cleaved from the composite primer with an enzyme that cleaves RNA from an RNA/DNA hybrid. Subsequently, an additional RNA/DNA chimeric primer is hybridized to the template such that the first extended primer is displaced from the target probe. The extension reaction is repeated, whereby multiple copies of the probe sequence are generated.

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference.

In general, PCR may be briefly described as follows. The double stranded hybridization complex is denatured, generally by raising the temperature, and then cooled in the presence of an excess of a PCR primer, which then hybridizes to the first universal priming site. A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand that hybridizes to the second universal priming site, rapid and exponential amplification occurs. Thus PCR steps are denaturation, annealing and extension. The particulars of PCR are well known, and include the use of a thermostable polymerase such as Taq I polymerase and thermal cycling. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase.

The reaction is initiated by introducing the target probe comprising the target sequence to a solution comprising the universal primers, a polymerase and a set of nucleotides. By "nucleotide" in this context herein is meant a deoxynucleoside-triphosphate (also called deoxynucleotides or dNTPs, e.g. dATP, dTTP, dCTP and dGTP). In some embodiments, as outlined below, one or more of the nucleotides may comprise a detectable label, which may be either a primary or a secondary label. In addition, the nucleotides may be nucleotide analogs, depending on the configuration of the system. Similarly, the primers may comprise a primary or secondary label.

Accordingly, the PCR reaction requires at least one PCR primer, a polymerase, and a set of dNTPs. As outlined herein, the primers may comprise the label, or one or more of the dNTPs may comprise a label.

In a preferred embodiment, instead of using two primers (e.g. unlabeled T3 and biotin-labeled T7), a third primer (overlapping with T7, but is shorter than T7; labeled with another dye, for example, Fam) is added to the PCR reaction. The PCR is first carried out at a lower stringent condition for a certain cycles, i.e. 25-30 cycles, in which both the longer and shorter PCR primers are annealed to the targets and generate PCR products; The PCR is then carried out at a higher stringent condition for additional cycles, say additional 5-10 cycles. Under this higher stringent condition, only the longer PCR primer can anneal to the targets and further generate PCR products, while the shorter PCR primer will not hybridize under this condition. Accordingly, for each of the target, two PCR products are generated with different PCR cycles and labeled with different dyes. Since the two products are presented at different concentrations in the final hybridization solution, the "shorter prime" signal can be used to measure the genes expressed at high level without running into saturation problem, while the "longer primer" signal is used to measure the genes expressed at low level without losing the sensitivity. While the invention is described using two primer variants, i.e. long and short prove, more than two variants can be used. That is, preferably more than two primer variants are used with more than five being particularly preferred.

In addition, identical primers can be used, but the primers bear different labels. In this embodiment the ratio of the two labels in the product can be adjusted by varying the initial primer concentrations, so there is no need to vary the PCR conditions.

In an alternative embodiment amplification can be performed using two or more dye labeled dNTP (for the PCR) or NTP (for the IVT), pre-mixed at different ratios. Accordingly, there is no need to vary the PCR conditions and PCR primer labeling. This method can also be used in the IVT step in gene expression monitoring using a direct hybridization with total RNA or mRNA, as a way to control the signal saturation problem. As such, detection of labels of different intensity serves to increase the range of detection of targets. That is, using less intense labels allows for detection of abundant targets without saturation while the use of stronger labels serves to increase sensitivity allowing for detection of less abundant targets.

In addition, the methods described above can be used in the final PCR step in OLA-PCR genotyping as well, as long as the dyes are chosen correctly such that they can be well-resolved by the hardware and/or software of the systems. That is following the OLA reaction, the ligation products can be amplified using primers as described above, i.e. either primer variants or differently labeled primers.

In a preferred embodiment, the methods of the invention include a rolling circle amplification (RCA) step. This may be done in several ways. In one embodiment, either single target probes or ligated probes can be used in the genotyping part of the assay, followed by RCA instead of PCR. Alternatively, and more preferably, the RCA reaction forms part of the genotyping reaction and can be used for both genotyping and amplification in the methods of the reaction.

In a preferred embodiment, the methods rely on rolling circle amplification. "Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) *Nuc. Acids Res.* 26:5073-5078; Barany, F. (1991) *Proc. Natl. Acad. Sci. USA* 88:189-193; and Lizardi et al. (1998) *Nat. Genet.* 19:225-232, all of which are incorporated by reference in their entirety.

In general, RCA may be described in two ways, as generally depicted in FIGS. 9 and 10. First, as is outlined in more detail below, a single target probe is hybridized with a target nucleic acid. Each terminus of the probe hybridizes adjacently on the target nucleic acid and the OLA assay as described above occurs. When ligated, the probe is circularized while hybridized to the target nucleic acid. Addition of a polyrnerase results in extension of the circular probe. However, since the probe has no terminus, the polymerase continues to extend the probe repeatedly. Thus results in amplification of the circular probe.

A second alternative approach involves a two step process. In this embodiment, two ligation probes are initially ligated together, each containing a universal priming sequence. A rolling circle primer is then added, which has portions that will hybridize to the universal priming sequences. The presence of the ligase then causes the original probe to circularize, using the rolling circle primer as the polymerase primer, which is then amplified as above.

These embodiments also have the advantage that unligated probes need not necessarily be removed, as in the absence of the target, no significant amplification will occur. These benefits may be maximized by the design of the probes; for example, in the first embodiment, when there is a single target probe, placing the universal priming site close to the 5' end of the probe since this will only serve to generate short, truncated pieces, without adapters, in the absence of the ligation reaction.

Accordingly, in an preferred embodiment, a single oligonucleotide is used both for OLA and as the circular template for RCA (referred to herein as a "padlock probe" or a "RCA probe"). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent to the first domain. Hybridization of the oligonucleotide to the target nucleic acid results in the formation of a hybridization complex. Ligation of the "primers" (which are the discrete ends of a single oligonucleotide) results in the formation of a modified hybridization complex containing a circular probe i.e. an RCA template complex. That is, the oligonucleotide is circularized while still hybridized with the target nucleic acid. This serves as a circular template for RCA. Addition of a primer and a polymerase to the RCA template complex results in the formation of an amplicon.

Labeling of the amplicon can be accomplished in a variety of ways; for example, the polymerase may incorporate labeled nucleotides, or alternatively, a label probe is used that is substantially complementary to a portion of the RCA probe and comprises at least one label is used, as is generally outlined herein.

The polymerase can be any polymerase, but is preferably one lacking 3' exonuclease activity (3' exo$^-$). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used. In addition, while some embodiments utilize ligase, such as in the OLA or RCA, in some embodiments amplification alone is preferred. That is amplification is performed without a ligase step and without including a ligase enzyme.

In a preferred embodiment, the RCA probe contains an adapter sequence as outlined herein, with adapter capture probes on the array, for example on a microsphere when microsphere arrays are being used. Alternatively, unique portions of the RCA probes, for example all or part of the sequence corresponding to the target sequence, can be used to bind to a capture probe.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA, the product nucleic acid is contacted with the appropriate restriction endonuclease. This results in cleavage of the product nucleic acid into smaller fragments. The fragments are then hybridized with the capture probe that is immobilized resulting in a concentration of product fragments onto the microsphere. Again, as outlined herein, these fragments can be detected in one of two ways: either labeled nucleotides are incorporated during the replication step, or an additional label probe is added.

Thus, in a preferred embodiment, the padlock probe comprises a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

The padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, e.g. is a universal priming site, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

Thus, the padlock probe of the invention contains at each terminus, sequences corresponding to OLA primers. The intervening sequence of the padlock probe contain in no particular order, an adapter sequence and a restriction endonuclease site. In addition, the padlock probe contains a RCA priming site.

Thus, in a preferred embodiment the OLA/RCA is performed in solution followed by restriction endonuclease cleavage of the RCA product. The cleaved product is then applied to an array comprising beads, each bead comprising a probe complementary to the adapter sequence located in the padlock probe. The amplified adapter sequence correlates with a particular target nucleic acid. Thus the incorporation of an endonuclease site allows the generation of short, easily hybridizable sequences. Furthermore, the unique adapter sequence in each rolling circle padlock probe sequence allows diverse sets of nucleic acid sequences to be analyzed in parallel on an array, since each sequence is resolved on the basis of hybridization specificity.

Thus, the present invention provides for the generation of amplicons (sometimes referred to herein as secondary targets).

In a preferred embodiment, the amplicons are labeled with a detection label. By "detection label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair such as biotin/streptavidin; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to the NTP and therefore to the amplicon) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

As outlined herein, labeling can occur in a variety of ways, as will be appreciated by those in the art. In general, labeling can occur in one of three ways: labels are incorporated into primers such that the amplification reaction results in amplicons that comprise the labels; labels are attached to dNTs and incorporated by the polymerase into the amplicons; or the amplicons comprise a label sequence that is used to hybridize a label probe, and the label probe comprises the labels. It should be noted that in the latter case, the label probe can be added either before the amplicons are contacted with an array or afterwards.

A preferred embodiment utilizes one primer comprising a biotin, that is used to bind a fluorescently labeled streptavidin.

In a preferred embodiment following amplification, the amplicons are subjected to an additional amplification step. Preferably the additional amplification step is a T7 RNA polymerase reaction, although T7 amplification also can be the primary amplification step. The advantage of following the amplification step with an additional amplification step such as the T7 RNA Polymerase reaction is that up to one hundred fold or more nucleic acid is generated therefore increasing the level of multiplexing.

As described above, the probes include T7 RNA polymerase priming sites for this additional step. In some embodiments this priming site comprises the universal priming site. Following amplification with T7 RNA polymerase, the resulting RNA contains a zip code and a universal primer that is allele specific. The resulting material is then detected.

In addition, in one embodiment of allele discrimination, the primers can include either T7 or T3 priming sites that are specific for a particular allele. That is, in addition to allele specific primers and universal priming sites for universal amplification, the primers may also include selective amplification priming site, such as either T7 or T3. By "selective" is meant a priming site that allows for allele selective amplification and discrimination. In the case of T7 or T3, the priming sites serve as promoters for RNA polymerases. For example, T3 promoter sequence is selective for a first allele and T7 is selective for a second allele. Thus, following the SNP specific OLA assay, including primary amplification, in vitro transcription (IVT) is performed in two separate reactions. Each reaction is carried out with one particular RNA Polymerase (T3 or T7). Preferably the reactions are carried out in the presence of a label. The products of the reactions are then detected.

In a preferred embodiment, following treatment of target nucleic acids with bisulfite, the modified target is contacted with target probes designed to be complementary to locus sequence and either the C or U at the potentially methylated position. Preferably one of the primers includes a first priming site and the other primer includes a second priming site. Such priming sites are exemplified, without limitation, by T3 and T7. Then the primers are replicated, either by amplification or an in vitro transcription reaction is preformed with T3 or T7 RNA Polymerase respectively, in the presence of different labels. Labeled amplification products are analyzed for the presence of either of the labels or both of the labels. In this way, the invention provides for a method of determining if zero, one or both chromosomes are methylated. That is, the results will demonstrate either the first label (corresponding to the first probe complementary to the C at the detection position), the second label (corresponding to the second probe complementary to the U at the detection position), or both.

In an additional embodiment the reactions are carried out with separate labels. That is, one label that corresponds to each reaction, i.e. Cy3 and Cy5 for T3 and T7, reactions, respectively, is included in the reactions. When two labels are used, the products of the reactions can be pooled and then detected by any of the detection methods described herein.

In one embodiment the amplicons are detected by hybridization to an array. The array can be an ordered array or a random array as described herein. In addition, the array can be a liquid array. That is, the array can be a solution-phase array and detection is accomplished in a FACS, for example. In a preferred embodiment the detection array is a random BeadArray™.

In addition the following methods that are typically used for genotyping, find use in methylation detection. That is, the present invention also provides methods for accomplishing genotyping of nucleic acids, including cDNA and genomic DNA. In general, this method can be described as follows, as is generally described in WO 00/63437, hereby expressly incorporated by reference. Genomic DNA is prepared from sample cells (and generally cut into smaller segments, for example through shearing or enzymatic treatment with enzymes such as DNAse I, as is well known in the art). In some embodiments a restriction enzyme is used. In this embodiment the restriction cleavage site and the target selections can be designed based on genomic sequences, i.e. using computer aided analysis, such that the un-methylated genomic regions will be digested by a methylation selective or discriminatory enzyme as described herein and will not be immobilized to the solid support or only part of the target will be immobilized.

Using any number of techniques, as are outlined below, the genomic fragments are attached, either covalently or securely, to a support such as beads or reaction wells (eppendorf tubes, microtiter wells, etc.). Any number of different reactions can then be done as outlined below to detect methylated target nucleic acids, and the reaction products from these reactions are released from the support, amplified as necessary and added to an array of capture probes as outlined herein. In general, the methods described herein relate to the detection of methylated target nucleotides Universal primers can also be included as necessary.

These techniques fall into five general categories: (1) techniques that rely on traditional hybridization methods that utilize the variation of stringency conditions (temperature, buffer conditions, etc.) to distinguish nucleotides at the detection position; (2) extension techniques that add a base ("the base") to basepair with the nucleotide at the detection position; (3) ligation techniques, that rely on the specificity of ligase enzymes (or, in some cases, on the specificity of chemical techniques), such that ligation reactions occur preferentially if perfect complementarity exists at the detection position; (4) cleavage techniques, that also rely on enzymatic or chemical specificity such that cleavage occurs preferentially if perfect complementarity exists; and (5) techniques that combine these methods. See generally WO 00/63437, incorporated by reference in its entirety.

As above, if required, the target genomic sequence is prepared using known techniques, and then attached to a solid support as defined herein. These techniques include, but are not limited to, enzymatic attachment, chemical attachment, photochemistry or thermal attachment and absorption.

In a preferred embodiment, as outlined herein, enzymatic techniques are used to attach the genomic DNA to the support. For example, terminal transferase end-labeling techniques can be used as outlined above; see Hermanson, Bioconjugate Techniques, San Diego, Academic Press, pp 640-643). In this embodiment, a nucleotide labeled with a secondary label (e.g. a binding ligand) is added to a terminus of the genomic DNA; supports coated or containing the binding partner can thus be used to immobilize the genomic DNA. Alternatively, the terminal transferase can be used to add nucleotides with special chemical functionalities that can be specifically coupled to a support. Similarly, random-primed labeling or nick-translation labeling (supra, pp. 640-643) can also be used.

In a preferred embodiment, chemical labeling (supra, pp. 6444-671) can be used. In this embodiment, bisulfite-catalyzed transamination, sulfonation of cytosine residues, bromine activation of T, C and G bases, periodate oxidation of RNA or carbodiimide activation of 5' phosphates can be done.

In a preferred embodiment, photochemistry or heat-activated labeling is done (supra, p162-166). Thus for example, aryl azides and nitrenes preferably label adenosines, and to a less extent C and T (Aslam et al., Bioconjugation: Protein Coupling Techniques for Biomedical Sciences; New York, Grove's Dictionaries, 833 pp.). Psoralen or angelicin compounds can also be used (Aslam, p492, supra). The preferential modification of guanine can be accomplished via intercalation of platinum complexes (Aslam, supra).

In a preferred embodiment, the genomic DNA can be absorbed on positively charged surfaces, such as an amine coated solid phase. The genomic DNA can be cross-linked to the surface after physical absorption for increased retention (e.g. PEI coating and glutaraldehyde cross-linking; Aslam, supra, p. 485).

In a preferred embodiment, direct chemical attached or photocrosslinking can be done to attach the genomic DNA to the solid phase, by using direct chemical groups on the solid phase substrate. For example, carbodiimide activation of 5' phosphates, attachment to exocyclic amines on DNA bases, and psoralen can be attached to the solid phase for crosslinking to the DNA.

Once added to the support, the target genomic sequence can be used in a variety of reactions for a variety of reasons. For example, in a preferred embodiment, genotyping reactions are done. Similarly, these reactions can also be used to detect the presence or absence of a target genomic sequence. In addition, in any reaction, quantitation of the amount of a target genomic sequence may be done. While the discussion below focuses on genotyping reactions, the discussion applies equally to detecting the presence of target sequences and/or their quantification.

As will be appreciated by those in the art, the reactions described below can take on a wide variety of formats. In one embodiment, genomic DNA is attached to a solid support, and probes comprising universal primers are added to form hybridization complexes, in a variety of formats as outlined herein. The non-hybridized probes are then removed, and the hybridization complexes are denatured This releases the probes (which frequently have been altered in some way). They are then amplified and added to an array of capture probes. In a preferred embodiment, non-hybridized primers are removed prior to the enzymatic step. Several embodiments of this have been described above. Alternatively, genomic DNA is attached to a solid support, and methylation reactions are done in formats that can allow amplification as well, either during the reaction (e.g. through the use of heat cycling) or after, without the use of universal primers. Thus, for example, when labeled probes are used, they can be hybridized to the immobilized genomic DNA, unbound materials removed, and then eluted and collected to be added to arrays. This may be repeated for amplification purposes, with the elution fractions pooled and added to the array. In addition, alternative amplification schemes such as extending a product of the invasive cleavage reaction (described below) to include universal primers or universal primers and adapters can be performed. In one embodiment this allows the reuse of immobilized target sequences with a different set or sets of target probes.

In some embodiments, amplification of the product of the genotyping reactions is not necessary. For example, in genomes of less complexity, e.g. bacterial, yeast and *Drosophila*, detectable signal is achieved without the need for amplification. This is particularly true when primer extension is performed and more than one base is added to the probe, as is more fully outlined below.

In a preferred embodiment, straight hybridization methods are used to elucidate the identity of the base at the detection position. Generally speaking, these techniques break down into two basic types of reactions: those that rely on competitive hybridization techniques, and those that discriminate using stringency parameters and combinations thereof.

In a preferred embodiment, the use of competitive hybridization probes is done to elucidate either the identity of the nucleotide(s) at the detection position or the presence of a mismatch. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

As outlined above, in a preferred embodiment, a plurality of readout probes are used to identify the base at the detection position. In this embodiment, each different readout probe comprises either a different detection label (which, as outlined below, can be either a primary label or a secondary label) or a different adapter, and a different base at the position that will hybridize to the detection position of the target sequence (herein referred to as the readout position) such that differential hybridization will occur.

Accordingly, in some embodiments, a detectable label is incorporated into the readout probe. In a preferred embodiment, a set of readout probes are used, each comprising a different base at the readout position. In some embodiments, each readout probe comprises a different label, that is distinguishable from the others. For example, a first label may be used for probes comprising adenosine at the readout position, a second label may be used for probes comprising guanine at the readout position, etc. In a preferred embodiment, the length and sequence of each readout probe is identical except for the readout position, although this need not be true in all embodiments.

In one embodiment, the probes used as readout probes are "Molecular Beacon" probes as are generally described in Whitcombe et al., Nature Biotechnology 17:804 (1999), hereby incorporated by reference. As is known in the art, Molecular Beacon probes form "hairpin" type structures, with a fluorescent label on one end and a quencher on the other. In the absence of the target sequence, the ends of the hairpin hybridize, causing quenching of the label. In the presence of a target sequence, the hairpin structure is lost in favor of target sequence binding, resulting in a loss of quenching and thus an increase in signal.

In a preferred embodiment, extension genotyping is done. In this embodiment, any number of techniques are used to add a nucleotide to the readout position of a probe hybridized to the target sequence adjacent to the detection position. By relying on enzymatic specificity, preferentially a perfectly complementary base is added. All of these methods rely on the enzymatic incorporation of nucleotides at the detection position. This may be done using chain terminating dNTPs, such that only a single base is incorporated (e.g. single base extension methods), or under conditions that only a single type of nucleotide is added followed by identification of the added nucleotide (extension and pyrosequencing techniques).

In a preferred embodiment, single base extension (SBE; sometimes referred to as "misequencing") is used to determine the identity of the base at the detection position. SBE utilizes an extension primer with at least one adapter sequence that hybridizes to the target nucleic acid immediately adjacent to the detection position, to form a hybridization complex. A polymerase (generally a DNA polymerase) is used to extend the 3' end of the primer with a nucleotide analog labeled with a detection label as described herein. Based on the fidelity of the enzyme, a nucleotide is only incorporated into the readout position of the growing nucleic acid strand if it is perfectly complementary to the base in the target strand at the detection position. The nucleotide may be derivatized such that no further extensions can occur, so only a single nucleotide is added. Once the labeled nucleotide is added, detection of the label proceeds as outlined herein. Again, amplification in this case is accomplished through cycling or repeated rounds of reaction/elution, although in some embodiments amplification is not necessary.

The reaction is initiated by introducing the hybridization complex comprising the target genomic sequence on the support to a solution comprising a first nucleotide. In general, the nucleotides comprise a detectable label, which may be either a primary or a secondary label. In addition, the nucleotides may be nucleotide analogs, depending on the configuration of the system. For example, if the dNTPs are added in sequential reactions, such that only a single type of dNTP can be added, the nucleotides need not be chain terminating. In addition, in this embodiment, the dNTPs may all comprise the same type of label.

Alternatively, if the reaction comprises more than one dNTP, the dNTPs should be chain terminating, that is, they have a blocking or protecting group at the 3' position such that no further dNTPs may be added by the enzyme. As will be appreciated by those in the art, any number of nucleotide analogs may be used, as long as a polymerase enzyme will still incorporate the nucleotide at the readout position. Preferred embodiments utilize dideoxy-triphosphate nucleotides (ddNTPs) and halogenated dNTPs. Generally, a set of nucleotides comprising ddATP, ddCTP, ddGTP and ddTTP is used, each with a different detectable label, although as outlined herein, this may not be required. Alternative preferred embodiments use acyclo nucleotides (NEN). These chain terminating nucleotide analogs are particularly good substrates for Deep vent (exo$^-$) and thermosequenase.

In addition, as will be appreciated by those in the art, the single base extension reactions of the present invention allow the precise incorporation of modified bases into a growing nucleic acid strand. Thus, any number of modified nucleotides may be incorporated for any number of reasons, including probing structure-function relationships (e.g. DNA:DNA or DNA:protein interactions), cleaving the nucleic acid, crosslinking the nucleic acid, incorporate mismatches, etc.

As will be appreciated by those in the art, the configuration of the methylation SBE system can take on several forms.

In addition, since unextended primers do not comprise labels, the unextended primers need not be removed. However, they may be, if desired, as outlined below; for example, if a large excess of primers are used, there may not be sufficient signal from the extended primers competing for binding to the surface.

Alternatively, one of skill in the art could use a single label and temperature to determine the identity of the base; that is, the readout position of the extension primer hybridizes to a position on the capture probe. However, since the three mismatches will have lower Tms than the perfect match, the use of temperature could elucidate the identity of the detection position base.

In a preferred embodiment, the determination of the identity of the base at the detection position of the target sequence proceeds using invasive cleavage technology. As outlined above for amplification, invasive cleavage techniques rely on the use of structure-specific nucleases, where the structure can be formed as a result of the presence or absence of a mismatch. Generally, invasive cleavage technology may be described as follows. A target nucleic acid is recognized by two distinct probes. A first probe, generally referred to herein as an "invader" probe, is substantially complementary to a first portion of the target nucleic acid. A second probe, generally referred to herein as a "signal probe", is partially complementary to the target nucleic acid; the 3' end of the signal oligonucleotide is substantially complementary to the target sequence while the 5' end is non-complementary and preferably forms a single-stranded "tail" or "arm". The non-complementary end of the second probe preferably comprises a "generic" or "unique" sequence, frequently referred to herein as a "detection sequence", that is used to indicate the presence or absence of the target nucleic acid, as described below. The detection sequence of the second probe may comprise at least one detectable label (for cycling purposes), or preferably comprises one or more universal priming sites and/or an adapter sequence. Alternative methods have the detection sequence functioning as a target sequence for a capture probe, and thus rely on sandwich configurations using label probes.

Hybridization of the first and second oligonucleotides near or adjacent to one another on the target genomic nucleic acid forms a number of structures.

Accordingly, the present invention provides methods of determining the identity of a base at the detection position of a target sequence. In this embodiment, the target sequence comprises, 5' to 3', a first target domain comprising an overlap domain comprising at least a nucleotide in the detection position, and a second target domain contiguous with the detection position. A first probe (the "invader probe") is hybridized to the first target domain of the target sequence. A second probe (the "signal probe"), comprising a first portion that hybridizes to the second target domain of the target sequence and a second portion that does not hybridize to the target sequence, is hybridized to the second target domain. If the second probe comprises a base that is perfectly complementary to the detection position a cleavage structure is formed. The addition of a cleavage enzyme, such as is described in U.S. Pat. Nos. 5,846,717; 5,614,402; 5,719,029; 5,541,311 and 5,843,669, all of which are expressly incorporated by reference, results in the cleavage of the detection sequence from the signaling probe. This then can be used as a target sequence in an assay complex.

In addition, as for a variety of the techniques outlined herein, unreacted probes (i.e. signaling probes, in the case of invasive cleavage), may be removed using any number of techniques. For example, the use of a binding partner coupled to a solid support comprising the other member of the binding pair can be done. Similarly, after cleavage of the primary signal probe, the newly created cleavage products can be selectively labeled at the 3' or 5' ends using enzymatic or chemical methods.

Again, as outlined above, the detection of the invasive cleavage reaction can occur directly, in the case where the detection sequence comprises at least one label, or indirectly, using sandwich assays, through the use of additional probes; that is, the detection sequences can serve as target sequences, and detection may utilize amplification probes, capture probes, capture extender probes, label probes, and label extender probes, etc. In one embodiment, a second invasive cleavage reaction is performed on solid-phase thereby making it easier perform multiple reactions.

In addition, as for most of the techniques outlined herein, these techniques may be done for the two strands of a double-stranded target sequence. The target sequence is denatured, and two sets of probes are added: one set as outlined above for one strand of the target, and a separate set for the other strand of the target.

Thus, the invasive cleavage reaction requires, in no particular order, an invader probe, a signaling probe, and a cleavage enzyme.

It is also possible to combine two or more of these techniques to do genotyping, quantification, detection of sequences, etc., again as outlined in WO 00/63437, expressly incorporated by reference, including combinations of competitive hybridization and extension, particularly SBE; a combination of competitive hybridization and invasive cleavage; invasive cleavage and ligation; a combination of invasive cleavage and extension reactions; a combination of OLA and SBE; a combination of OLA and PCR; a combination of competitive hybridization and ligation; and a combination of competitive hybridization and invasive cleavage.

Solution Phase Assays

Alternatively, the assays of the invention can be run in solution, followed by detection of the amplicons, either by the addition of the amplicons to an array or utilizing other methods as outlined herein (mass spectroscopy, electrophoresis, etc.) as outlined herein. In this embodiment, a variety of methods can be used to remove unhybridized target probes, as outlined in WO 00/63437, expressly incorporated by reference herein.

For example, if the target analyte is not immobilized, separation methods based on the differences between single-stranded and double-stranded nucleic acids may be done. For example, there are a variety of double-stranded specific moieties known, that preferentially interact with double-stranded nucleic acids over single stranded nucleic acids. For example, there are a wide variety of intercalators known, that insert into the stacked basepairs of double stranded nucleic acid. Two of the best known examples are ethidium bromide and actinomycin D. Similarly, there are a number of major groove and minor groove binding proteins which can be used to distinguish between single stranded and double stranded nucleic acids. Similar to the poly(T) embodiment, these moieties can be attached to a support such as magnetic beads and used to preferentially bind the hybridization complexes, to remove the non-hybridized target probes and target sequences during washing steps. The hybridization complexes are then released from the beads using a denaturation step such as a thermal step.

In the case where the OLA reaction is done, an additional embodiment, depicted in FIG. 8, may be done to remove unhybridized primers. In this embodiment, a nuclease inhibitor is added to the 3' end of the downstream ligation probe, which does not comprise the adapter sequence. Thus, any nucleic acids that do not contain the inhibitors (including both the 5' unligated probe and the target sequences themselves) will be digested upon addition of a 3'-exonuclease. The ligation products are protected from exo I digestion by including, for example, 4-phosphorothioate residues at their 3' terminus, thereby, rendering them resistant to exonuclease digestion. The unligated detection oligonucleotides are not protected and are digested. Since the 5' upstream ligation probe carries the adapter sequence, the unligated downstream probe, which does carry the nuclease inhibitor and is thus also not digested, does not bind to the array and can be washed away. The nuclease inhibitors may also be used in non-OLA utilities as well.

Suitable nuclease inhibitors are known in the art and comprise thiol nucleotides. In this embodiment, suitable 3'-exonucleases include, but are not limited to, exo I, exo III, exo VII, and 3'-5' exophosphodiesterases.

Following the amplification procedure, there is present sufficient nucleic acid material to detect the results of the genotyping assays through conventional means. In the preferred embodiment, the probes used in the mutation detection reaction also contain address sequences. During the amplification process, the address sequences used to read out the results are simultaneously amplified with the mutation-detection probes. When the amplified material is applied to a detection substrate, such as an array where complementary address sequences are provided, the amplified nucleic acid probes are then detected by known methods.

Combination Techniques

Other preferred configurations of the system are set forth in U.S. Ser. No. 10/177,727, filed Jun. 20, 2002 now published U.S. application 2003/0200489 and Ser. No. 10/194,958, filed Jul. 12, 2002, now U.S. Pat. No. 7,582,240 both of which are expressly incorporated herein by reference.

The following methods are generally directed to methods of allele detection and find use in detecting methylated target nucleic acids when the target nucleic acids are subjected to the methylation selective methods described herein. Accordingly, following a methylation selective step as described herein, and immobilization of the modified target, in one embodiment the target nucleic acids are contacted with allele specific probes under stringent annealing conditions. Non-hybridized probes are removed by a stringent wash. Subsequently the hybridized probes or primers are contacted with an enzyme such as a polymerase in the presence of labeled ddNTP forming a modified primer. Preferably the label is a purification tag as described herein. The ddNTP is only incorporated into the primer that is perfectly complementary to the target nucleic acid. The modified primer is then eluted from the immobilized target nucleic acid, and contacted with amplification primers to form amplicons. In one embodiment the eluted primer is purified by binding to a binding partner for the affinity tag. Then the purified and modified primer is contacted with amplification primers for amplification, forming amplicons. The amplicons are then detected as an indication of the presence of the particular target nucleic acid, e.g. determining whether the target is methylated or not.

In a preferred embodiment, the allele specific primer also includes an adapter sequence and priming sequences as described herein.

Alternatively, allele detection proceeds as a result of allele specific amplification. That is, at least one of the priming sequences on the primers for each allele is specific for a particular allele, or methylation state of the target. Thus, following hybridization of the primers and removal of the unhybridized primers, one of the alleles will be identified. Following addition of the respective amplification primers, only one set of the primers will hybridize with the priming sequences. Thus, only one of the sets of primers will generate an amplicon. In a preferred embodiment, each of the sets of primers is labeled with distinct label. Because only one of the sets will be amplified, detection of a label provides an indication of the primer that was amplified. This, in turn identifies the nucleotide at the detection position.

In an alternative embodiment the target nucleic acid is first contacted with a first target specific probe under stringent annealing conditions and a first extension reaction is performed with either dNTPs or ddNTPS forming a first extension product. The first target specific probe in this embodiment is either a locus specific probe or an allele specific probe. This step reduces the complexity of the sample. Subsequently the first extension product is contacted with a second probe that has the same sequence as a portion of the target sequence, i.e. the second probe is complementary to the extension product, and again can be either an allele specific probe or a locus specific probe. Following hybridization of the second probe, a second extension reaction is performed.

In a preferred embodiment the primers for the first and second extension reaction also include amplification priming sites. Preferably the amplification priming sites are universal priming sites as described herein. Accordingly, the resulting extension product is amplified (the amplification component of the multiplexing scheme). The resulting double stranded product is then denatured and either of the strands is used as a template for a single base extension (SBE) reaction as described in more detail below (the specificity component). In the SBE reaction, chain terminating nucleotides such as ddTNPs are used as substrates for the polymerase and are incorporated into a target probe that is hybridized to the single stranded amplicon template adjacent to the interrogation position. Preferably the ddNTPs are labeled as described below. Preferably, the ddNTPs are discretely labeled such that they can be discriminated in the detection step.

In an alternative embodiment a first biotinylated or otherwise tagged probe is hybridized with a target nucleic acid and a first extension reaction is performed. The primer or probe is either an allele specific or locus specific probe. The extended product is then purified from the mixture by the tag. Again, this serves as the complexity reduction step. Subsequently, a second primer is hybridized to the first extension product and a second extension reaction is performed, preferably in an allele specific manner, i.e. with discriminatory probes that are specific for, each allele. This represents the specificity step. Preferably, both of the primers used in the extension reactions contain universal priming sites. Thus, universal primers can be added for universal amplification of the extension products (the amplification component. In a preferred embodiment, each allele specific primer includes a distinct amplification priming site. Thus, following allele discrimination, only one of the primers can be used for amplification, resulting in allele specific amplification. Preferably the amplification primers contain discrete labels, which again allows for detection of which particular primers served as amplification templates. This, again, identifies the particular allele to be detected. In an additional preferred embodiment, at least one of the primers includes an adapter sequence as outlined below.

In an alternative embodiment tagged, i.e. biotinylated, primers are hybridized with a target nucleic acid. Preferably the hybridization complex is immobilized. Either the target or the primer can be the immobilized component. After annealing, the immobilized complexes are washed to remove unbound nucleic acids. This is followed by an extension reaction. This is the complexity reduction component of the assay. Subsequently, the extended probe is removed via the purification tag. The purified probe is then hybridized with allele specific probes (the specificity component). The hybridized probes are then amplified (the amplification component).

In a preferred embodiment the allele specific probe contains universal priming sites and an adapter sequence. Preferably the universal priming sites are specific for a particular allele. That is, one of the universal priming sites may be common to all alleles, but the second universal priming site is specific for a particular allele. Following hybridization the allele specific primer, the complexes are washed to remove unbound or mismatched primers. Thus, this configuration allows for allele specific amplification. Amplicons are detected as an indication of the presence of a particular allele.

In an alternative embodiment, the specificity component occurs first, In this embodiment allele specific probes are hybridized with the target nucleic acid; an extension assay is performed whereby only the perfectly complementary probe is extended. That is, only the probe that is perfectly complementary to the probe at the interrogation position serves as a substrate for extension reaction. Preferably the extension reaction includes tagged, i.e. biotinylated, dNTPs such that the extension product is tagged. The extension product is then purified from the reaction mixture. Subsequently, a second allele specific primer is hybridized to the extension product. This step also serves as a second specificity step. In this embodiment the specificity steps also serve as complexity reduction components in that they enrich for target nucleic acids. Following the addition of the second allele specific primer and extension, the extension product is amplified, preferably with universal primers.

As discussed previously, it is preferably for the at least one allele specific primer to contain an allele specific priming site, preferably an allele specific universal priming site. Again, this configuration allows for multiplexed allele specific amplification using universal primers.

In an alternative embodiment, the target nucleic acid is first immobilized and hybridized with allele specific primers. Preferably the allele specific primers also include an adapter sequence that is indicative of the particular allele. Allele specific extension is then performed whereby only the primer that is perfectly complementary to the detection position of the target nucleic acid will serve as a template for primer extension. That is, mismatched primers will not be extended. Of note, the allele specific position of the primer need not be the 3' terminal nucleotide of the primer. That is, the primer may extend beyond the detection position of the target nucleic acid. In this embodiment it is preferable to include labeled dNTPs or ddNTPs or both such that the extension product is labeled and can be detected. In some preferred embodiments the interrogator is not the terminal position of the primer, but rather resides at a position 1, 2, 3, 4, 5 or 6 nucleotides from the 3' terminus of the primer.

In a preferred embodiment both dNTPs and ddNTPs are included in the extension reaction mixture. In this embodiment only one label is needed, and the amount of label can be determined and altered by varying the relative concentration of labeled and unlabeled dTNPs and ddNTPs. That is, in one embodiment labeled ddNTPs are included in the extension mix at a dilution such that each termination will result in placement of single label on each strand. Thus, this method allows for quantification of targets. Alternatively, if a higher signal is needed, a mixture of labeled dNTPs can be used along with chain terminating nucleotides at a lower concentration. The result is the incorporation of multiple labels per extension product. Preferably the primers also include adapters which facilitate immobilization of the extension products for detection.

In an additional preferred configuration, target nucleic acids are hybridized with tagged locus specific primers. Preferably the primer includes a locus specific portion and a universal priming site. Of note, as is generally true for locus specific primers, they need not be immediately adjacent to the detection position. Upon hybridization, the hybridization complexes are immobilized, preferably by binding moiety that specifically binds the tag on the locus specific primer. The immobilized complexes are then washed to remove unlabeled nucleic acids; the remaining hybridization complexes are then subject to an extension reaction. Following extension of the locus specific primer, a nucleotide complementary to the nucleotide at the detection position will be incorporated into the extension product. In some embodiments it is desirable to limit the size of the extension because this reduces the complexity of subsequent annealing steps. This may be accomplished by including both dNTPs and ddNTPs in the reaction mixture.

Following the first extension, a second locus or allele specific primer is hybridized to the immobilized extension product and a second extension reaction occurs. Preferably the second extension primer includes a target specific portion and a universal priming site. After extension, universal amplification primers can be added to the reaction and the extension products amplified. The amplicons can then be used for detection of the particular allele. This can be accomplished by competitive hybridization, as described herein. Alternatively, it can be accomplished by an additional extension reaction. When the extension reaction is performed, preferably a primer that contains an adapter sequence and a target specific portion is hybridized with the amplicons. Preferably the target specific portion hybridizes up to a position that is adjacent to the detection position, i.e. the particular allele to be detected. Polymerase and labeled ddNTPs are then added and the extension reaction proceeds, whereby incorporation of a particular label is indicative of the nucleotide that is incorporated into the extension primer. This nucleotide is complementary to the nucleotide at the detection position. Thus, analyzing or detecting which nucleotide is incorporated into the primer provides an indication of the nucleotide at the allele position. The extended primer is detected by methods that include but are not limited to the methods described herein.

In another embodiment, the genotyping specificity is conferred by the extension reaction. In this embodiment, two probes (sometimes referred to herein as "primers") are hybridized non-contiguously to a target sequence comprising, from 3' to 5', a first second and third target domain. Preferably the target is immobilized. That is, in a preferred embodiment, the target sequence is genomic DNA and is attached to a solid support as is generally described in U.S. Ser. No. 09/931,285, hereby expressly incorporated by reference in its entirety. In this embodiment, magnetic beads, tubes or microtiter plates are particularly preferred solid supports, although other solid supports as described below can also be used.

The first probe hybridized to the first domain, contains a first universal priming sequence and contains, at the 3' end (within the terminal six bases), an interrogation position. In some preferred embodiments the interrogator is not the terminal position of the primer, but rather resides at a position 1, 2, 3, 4, 5 or 6 nucleotides from the 3' terminus of the primer. Subsequently, the unhybridized primers are removed. This is followed by providing an extension enzyme such as a polymerase, and NTPs (which includes both dNTPs, NTPs and analogs, as outlined below). If the interrogation position is perfectly complementary to the detection position of the target sequence, the extension enzyme will extend through the second target domain to form an extended first probe, ending at the beginning of the third domain, to which the second probe is hybridized. A second probe is complementary to the third target domain, and upon addition of a ligase, the extended first probe will ligate to the second probe. The addition of a primer allows amplification to form amplicons. If the second probe comprises an antisense second primer, exponential amplification may occur, such as in PCR. Similarly, one or other of the probes may comprise an adapter or address sequence, which facilitates detection. For example, the adapter may serve to allow hybridization to a "universal array". Alternatively, the adapter may serve as a mobility modifier for electrophoresis or mass spectrometry analysis, or as a label sequence for the attachment of labels or beads for flow cytometry analysis.

In another embodiment, the reaction is similar except that it is the ligation reaction that provides the detection position/interrogation specificity. In this embodiment, it is the second probe that comprises a 5' interrogation position. The extended first probe will not be ligated to the second probe if there is a mismatch between the interrogation position and the target sequence. As above, the addition of a primer allows amplification to form amplicons. If the second probe comprises an antisense second primer, exponential amplification may occur, such as in PCR. Similarly, one or other of the probes may comprise an adapter or address sequence, which facilitates detection. For example, the adapter may serve to allow hybridization to a "universal array". Alternatively, the adapter may serve as a mobility modifier for electrophoresis or mass spectrometry analysis, or as a label sequence for the attachment of labels or beads for flow cytometry analysis.

Once prepared, and attached to a solid support as required, the target sequence is used in genotyping or methylation detection reactions. It should be noted that while the discussion below focuses on certain assays, in general, for each reaction, each of these techniques may be used in a solution based assay, wherein the reaction is done in solution and a reaction product is bound to the array for subsequent detection, or in solid phase assays, where the reaction occurs on the surface and is detected, either on the same surface or a different one.

The assay continues with the addition of a first probe. The first probe comprises, a 5' first domain comprising a first universal priming sequence. The universal priming sites are used to amplify the modified probes to form a plurality of amplicons that are then detected in a variety of ways, as outlined herein. In preferred embodiments, one of the universal priming sites is a T7 site, such that RNA is ultimately made to form the amplicon. Alternatively, as more fully outlined below, two universal priming sequences are used, one on the second probe generally in antisense orientation, such that PCR reactions or other exponential amplification reactions can be done. Alternatively, a single universal primer can be used for amplification. Linear amplification can be performed using the SPIA assay, T7 amplification, linear TMA and the like, as described herein.

The first probe further comprises, 3' to the priming sequence, a second domain comprising a sequence substantially complementary to the first target domain of the target sequence. Again, the second target domain comprises n nucleotides, wherein n is an integer of at least 1, and preferably from 1 to 100 s, with from 1 to 10 being preferred and from 1, 2, 3, 4 and 5 being particularly preferred. What is important is that the first and third target domains are non-contiguous, e.g. not adjacent.

In a preferred embodiment, the first probe, further comprises, 3' to the second domain, an interrogation position within the 3' six terminal bases. As used herein, the base which basepairs with a detection position base in a hybrid is termed a "readout position" or an "interrogation position"; thus one or the other of the first or second probes of the invention comprise an interrogation position, as outlined herein. In some cases, when two SNP positions or detection positions are being elucidated, both the first and the second probes may comprise interrogation positions.

When the first probe comprises the interrogation position, it falls within the six 3' terminal nucleotides, with in three, and preferably two, and most preferably it is the 3' terminal nucleotide. In some preferred embodiments the interrogator is not the terminal position of the primer, but rather resides at a position 1, 2, 3, 4, 5 or 6 nucleotides from the 3' terminus of the primer. Alternatively, the first probe does not contain the interrogation position; rather the second probe does. This depends on whether the extension enzyme or the ligation enzyme is to confer the specificity required for the genotyping reaction.

In addition to the first probes of the invention, the compositions of the invention further comprise a second probe for each target sequence. The second probes each comprise a first domain comprising a sequence substantially complementary to the third target domain of a target sequence as outlined herein.

In some embodiments, the second probes comprise a second universal priming site. As outlined herein, the first and second probes can comprise two universal primers, one in each orientation, for use in PCR reactions or other amplification reactions utilizing two primers. That is, as is known in the art, the orientation of primers is such to allow exponential amplification, such that the first universal priming sequence is in the "sense" orientation and the second universal priming sequence is in the "antisense" orientation.

In a preferred embodiment, it is the second probe that comprises the interrogation position. In this embodiment, the second probe comprises a 5' interrogation nucleotide, although in some instances, depending on the ligase, the interrogation nucleotide may be within 1-3 bases of the 5' terminus. However, it is preferred that the interrogation base be the 5' base.

In a preferred embodiment, either the first or second probe further comprises an adapter sequence, (sometimes referred to in the art as "zip codes") to allow the use of "universal arrays". That is, arrays are generated that contain capture probes that are not target specific, but rather specific to individual artificial adapter sequences.

It should be noted that when two universal priming sequences and an adapter is used, the orientation of the construct should be such that the adapter gets amplified; that is, the two universal priming sequences are generally at the termini of the amplification template, described below.

The first and second probes are added to the target sequences to form a first hybridization complexes. The first hybridization complexes are contacted with a first universal primer that hybridizes to the first universal priming sequence, an extension enzyme and dNTPs.

If it is the first probe that comprises the interrogation nucleotide, of the base at the interrogation position is perfectly complementary with the base at the detection position, extension of the first primer occurs through the second target domain, stopping at the 5' of the second probe, to form extended first probes that are hybridized to the target sequence, forming second hybridization complexes. If, however, the base at the interrogation position is not perfectly complementary with the base at the detection position, extension of the first probe will not occur, and no subsequent amplification or detection will occur.

Extension of the enzyme will also occur if it is the second probe that comprises the interrogation position. Once extended, the extended first probe is adjacent to the 5' end of the second probe. In the case where the interrogation position was in the first probe, the two ends of the probes (the 3' end of the first probe and the 5' end of the second probe) are respectively perfectly complementary to the target sequence at these positions, and the two probes can be ligated together with a suitable ligase to form amplification templates.

The conditions for carrying out the ligation will depend on the particular ligase used and will generally follow the manufacturer's recommendations.

If, however, it is the second probe that carries the interrogation position at its 5' end, the base at the interrogation position must be perfectly complementary to the detection position in the target sequence to allow ligation. In the absence of perfect complementarity, no significant ligation will occur between the extended first probe and the second probe.

It should be noted that the enzymes may be added sequentially or simultaneously. If the target sequences are attached to a solid support, washing steps may also be incorporated if required.

The ligation of the extended first probe and the second probe results in an amplification template comprising at least one, and preferably two, universal primers and an optional adapter. Amplification can then be done, in a wide variety of ways. As will be appreciated by those in the art, there are a wide variety of suitable amplification techniques requiring either one or two primers, as is generally outlined in U.S. Ser. No. 09/517,945, now U.S. Pat. No. 6,355,431, hereby expressly incorporated by reference.

Accordingly, the invention provides a method of identifying candidate disease genes by identifying genes with altered methylation. That is, methylation patterns as detected by the methods described herein are compared between healthy patients and sick or diseased patients. Alternatively, samples from healthy tissues are compared with samples from sick or diseased tissues.

In addition the invention provides methods of diagnosing diseases. That is, as noted herein, certain aberrations in methylation patterns of certain genes results in diseases. According to the methods as described herein these diseases can be diagnosed in a highly multiplex fashion. In addition, because the method also provides for identifying additional methylated genes or patterns, additional diseases related to aberrant methylation of genes are diagnosed by the methods of the invention.

In the preferred method, the detection substrate used for any of the above assays is a random array substrate, as described in U.S. Pat. No. 6,023,540 which is incorporated by reference herein, where the hybridization of complementary nucleic acid sequences, or address sequences, are used as the particular detection means. The arrays can be manufactured with a standard set of nucleic acid address sequences, one address sequence for each different nucleic acid to be detected. The complementary nucleic acid sequences are provided as part of the linear nucleic acid sequences of the mutation-detection probes, inside of the working portion of the amplification primers. During amplification, the address sequences are amplified along with each respective mutation-detection probe. In order to detect the results of the multiplexed genotyping reaction, the resulting amplified mutation-detection probe mixture is applied to the array, whereby the complementary address sequences on the mutation-detection probes and on the array hybridize, and the results are analyzed by known methods, such as fluorescence.

Other detection schemes such as flow cytometry, mass spectroscopy, capillary electrophoresis, spotted arrays, or spatially-directed arrays can also be used to simultaneously read the results of the multiplexed nucleic acid detection reactions.

Accordingly, the present invention provides methods and compositions useful in the detection of nucleic acids, particularly the labeled amplicons outlined herein. As is more fully outlined below, preferred systems of the invention work as follows. Amplicons are attached (via hybridization) to an array site. This attachment can be either directly to a capture probe on the surface, through the use of adapters, or indirectly, using capture extender probes as outlined herein. In some embodiments, the target sequence itself comprises the labels. Alternatively, a label probe is then added, forming an assay complex. The attachment of the label probe may be direct (i.e. hybridization to a portion of the target sequence), or indirect (i.e. hybridization to an amplifier probe that hybridizes to the target sequence), with all the required nucleic acids forming an assay complex.

Accordingly, the present invention provides array compositions comprising at least a first substrate with a surface comprising individual sites. By "array" or "biochip" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc. A preferred embodiment utilizes microspheres on a variety of substrates including fiber optic bundles, as are outlined in PCTs US98/21193, now published international application WO99/18434, PCT US99/14387, now published international application WO99/67641 and PCT US 98/05025, now published international application WO99/67641; WO98/50782; and U.S. Ser. No. 09/287,573, now U.S. Pat. Nos. 7,348,181, 09/151,877, now U.S. Pat. Nos.6,327,410, 09/256,943, now U.S. Pat. Nos. 6,429,027, 09/316,154, now U.S. Pat. Nos. 6,364,790, 60/119,323, 09/315,584, now U.S. Pat. No. 6,544,732; all of which are expressly incorporated by reference.

Arrays containing from about 2 different bioactive agents (e.g. different beads, when beads are used) to many millions can be made, with very large arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred (all numbers being in square cm). High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 μm or less (with beads of 200 nm possible) can be used, and very small fibers are known, it is possible to have as many as 40,000 or more (in some instances, 1 million) different elements (e.g. fibers and beads) in a 1 mm$^2$ fiber optic bundle, with densities of greater than 25,000,000 individual beads and fibers (again, in some instances as many as 50-100 million) per 0.5 cm$^2$ obtainable (4 million per square cm for 5μ center-to-center and 100 million per square cm for 1μ center-to-center).

By "substrate", "array substrate" or "solid support" or other grammatical equivalents herein is meant any material that can be modified to contain discrete individual sites appropriate for the attachment or association of beads and is amenable to at least one detection method. It should be noted that the array substrate is distinct from the "capture surface" described above. The capture surface is for the immobilization of target nucleic acids while the array substrate is for detection of amplicons, i.e. the results of the detection or genotyping assay. As will be appreciated by those in the art, the number of possible array substrates is very large. Possible array substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the array substrates allow optical detection and do not themselves appreciably fluoresce.

Generally the array substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as paper, glass, polystyrene and other plastics and acrylics.

In a preferred embodiment, the substrate is an optical fiber bundle or array, as is generally described in U.S. Ser. No. 08/944,850, now U.S. Pat. No. 7,115,884, and Ser. No. 08/519,062, now U.S. Pat. No. 6,200,737, PCT US98/05025, now published international application WO98/40726and PCT US98/09163, now published international application WO98/50782, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the array of array compositions of the invention can be configured in several ways; see for example U.S. Ser. No. 09/473,904, now U.S. Pat. No. 6,858,394,hereby expressly incorporated by reference. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below. Arrays are described in U.S. Pat. No. 6,023,540 and U.S. Ser. No. 09/151,877, filed Sep. 11, 1998, now U.S. Pat. No. 6,327,410, Ser. No. 09/450,829, filed Nov. 29, 1999, now U.S. Pat. No. 6,266,459, Ser. No. 09/816,651, filed Mar. 23, 2001, now abandoned, and Ser. No. 09/840,012, filed Apr. 20, 2001, now abandoned, all of which are expressly incorporated herein by reference. In addition, other arrays are described in 60/181, 631, filed Feb. 10, 2000, Ser. No. 09/782,588, filed Feb. 12, 2001, now abandoned, Ser. No. 60/113,968, filed Dec. 28, 1998, Ser. No. 09/256,943, filed Feb. 24, 1999, now U.S. Pat. No. 6,429,027 Ser. No. 09/473,904, filed Dec. 28, 1999, now U.S. Pat. No. 6,858,394 and Ser. No. 09/606,369, filed Jun. 28, 2000, now Abandoned, all of which are expressly incorporated herein by reference.

Alternatively, a "two component" system can be used. In this embodiment, the individual arrays are formed on a second substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/ quality control. As will be appreciated by those in the art, there are a variety of ways to configure the system. In addition, the random nature of the arrays may mean that the same population of beads may be added to two different surfaces, resulting in substantially similar but perhaps not identical arrays.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites. That is, while beads need not occupy each site on the array, no more than one bead occupies each site.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. No. 08/818,199 and Ser. No. 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In some embodiments, the beads are not associated with a substrate. That is, the beads are in solution or are not distributed on a patterned substrate.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each capture probe; preferred embodiments utilize a plurality of beads of each type.

By "microspheres" or "beads" or "particles" or grammatical equivalents herein is meant small discrete particles. The composition of the beads will vary, depending on the class of capture probe and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either capture probe attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

Each microsphere comprises a capture probe, although as will be appreciated by those in the art, there may be some microspheres which do not contain a capture probe, depending on the synthetic methods.

Attachment of the nucleic acids may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc. In a preferred embodiment, affinity capture is used to attach the nucleic acids to the beads. For example, nucleic acids can be derivatized, for example with one member of a binding pair, and the beads derivatized with the other member of a binding pair. Suitable binding pairs are as described herein for IBL/DBL pairs. For example, the nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Similarly, affinity capture utilizing hybridization can be used to attach nucleic acids to beads. Alternatively, chemical crosslinking may be done, for example by photoactivated crosslinking of thymidine to reactive groups, as is known in the art.

In a preferred embodiment, each bead comprises a single type of capture probe, although a plurality of individual capture probes are preferably attached to each bead. Similarly, preferred embodiments utilize more than one microsphere containing a unique capture probe; that is, there is redundancy built into the system by the use of subpopulations of microspheres, each microsphere in the subpopulation containing the same capture probe.

As will be appreciated by those in the art, the capture probes may either be synthesized directly on the beads, or they may be made and then attached after synthesis. In a preferred embodiment, linkers are used to attach the capture probes to the beads, to allow both good attachment, sufficient flexibility to allow good interaction with the target molecule, and to avoid undesirable binding reactions.

In a preferred embodiment, the capture probes are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the capture probes are synthesized first, and then covalently attached to the beads. As will be appreciated by those in the art, this will be done depending on the composition of the capture probes and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

When random arrays or liquid arrays are used, an encoding/decoding system must be used. For example, when microsphere arrays are used, the beads are generally put onto the substrate randomly; as such there are several ways to correlate the functionality on the bead with its location, including the incorporation of unique optical signatures, generally fluorescent dyes, that could be used to identify the nucleic acid on any particular bead. This allows the synthesis of the capture probes to be divorced from their placement on an array, i.e. the capture probes may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or probe at that particular site can be made. This means that the beads may be randomly distributed on the array, a fast and inexpensive process as compared to either the in situ synthesis or spotting techniques of the prior art.

When liquid arrays are used, beads to which the amplicons are immobilized can be analyzed by FACS. Again, beads can be decoded to determine which amplicon is immobilized on the bead. This is an indication of the presence of the target analyte.

However, the drawback to these methods is that for a large array, the system requires a large number of different optical signatures, which may be difficult or time-consuming to utilize. Accordingly, methods for analysis and decoding of arrays are described in Ser. No. 08/944,850, filed Oct. 6, 1997, now U.S. Pat. No. 7,115,884, PCT/US98/21193, filed Oct. 6, 1998, now published international application WO99/18434, Ser. No. 09/287,573, filed Apr. 6, 1999, now U.S. Pat. No. 7,348,181, PCT/US00/09183, filed May 6, 2000, now published international application WO00/60332, Ser. No. 60/238,866, filed Oct. 6, 2000, Ser. No. 60/119,323, filed Feb. 9, 1999, Ser. No. 09/500,555, filed Feb. 9, 2000, now abandoned, Ser. No. 09/636,387, filed Aug. 9, 2000, now Abandoned, Ser. No. 60/151,483, filed Aug. 30, 1999, Ser. No. 60/151,668, filed Aug. 31, 1999, Ser. No. 09/651,181, filed Aug. 30, 2000, now U.S. Pat. No. 6,942,948, Ser. No. 60/272,803, filed Mar. 1, 2001, all of which are expressly incorporated herein by reference. In addition, methods of decoding arrays are described in 60/090,473, filed Jun. 24, 1998, Ser. No. 09/189,543, filed Nov. 10, 1998, now abandoned, Ser. No. 09/344,526, filed Jun. 24, 1999, now U.S. Pat. No. 7,060,431PCT/US99/14387, filed Jun. 24, 1999, now published international application WO99/67641, Ser. No. 60/172,106, filed Dec. 23, 1999, Ser. No. 60/235,531, filed Sep. 26, 2000, Ser. No. 09/748,706, filed Dec. 22, 2000, now U.S. Pat. No. 7,033,754, and provisional application entitled Decoding of Array Sensors with Microspheres, filed Jun. 28, 2001 (no serial number received), all of which are expressly incorporated herein by reference.

As outlined herein, the present invention finds use in a wide variety of applications. All references cited herein are incorporated by reference.

EXAMPLES

Example 1

Attachment of Genomic DNA to a Solid Support

1. Fragmentation of Genomic DNA

| Human Genomic DNA | 10 _g (100 µl) |
|---|---|
| 10× DNase I Buffer | 12.5 µl |
| DNase I (1 U/_µl, BRL) | 0.5 µl |
| ddH2O | 12 µl |

Incubate 37° C. for 10 min. Add 1.25 µl 0.5 M EDTA, Heat at 99° C. for 15 min.

2. Precipitation of Fragmented Genomic DNA

| DNase I fragmented genomic DNA | 125 µl |
|---|---|
| Quick-Precip Plus Solution (Edge Biosystems) | 20 µl |
| Cold 100% EtOH | 300 µl |

Store at −20° C. for 20 min. Spin at 12,500 rpm for 5 min. Wash pellet 2× with 70% EtOH, and air dry.

3. Terminal Transferase End-Labeling with Biotin

| DNase I fragmented and precipitated genomic DNA (in H2O) | 77.3 μl |
|---|---|
| 5× Terminal transferase buffer | 20 μl |
| Biotin-N6-ddATP (1 mM, NEN) | 1 μl |
| Terminal transferase (15 U/μl) | 1.7 μl |

37° C. for 60 min. Add 1 μl 0.5 M EDTA, then heat at 99° C. for 15 min

4. Precipitation of Biotin-Labeled Genomic DNA

| Biotin-labeled genomic DNA | 100 μl |
|---|---|
| Quick-Precip Solution | 20 μl |
| EtOH | 250 μl |

−20° C. for 20 min and spin at 12,500 rpm for 5 min, wash 2× with 70% EtOH and air dry.

5. Immobilization of Biotin-Labeled Genomic DNA to Streptavidin-Coated PCR Tubes Heat-Denature Genomic DNA for 10 min on 95° C. Heat Block.

| Biotin-labeled genomic DNA (0.3 g/μl) | 3 μl |
|---|---|
| _× binding buffer | 25 μl |
| SNP Primers (50 nM) | 10 μl |
| ddH2O | 12 μl |

Incubate at 60° C. for 60 min.
Wash 1× with 1× binding buffer,
1× with 1× washing buffer,
1× with 1× ligation buffer.
1× binding buffer: 20 mM Tris-HCl, pH7.5, 0.5M NaCl, 1 mM EDTA, 0.1% SDS.
1× washing buffer: 20 mM Tris-HCl pH7.5, 0.1 M NaCl, 1 mM EDTA, 0.1% Triton X-100.
1× ligation buffer: 20 mM Tris-HCl pH7.6, 25 mM Potassium acetate, 10 mM magnesium acetate, 10 mM DTT, 1 mM NAD, 0.1% Triton X-100.

6. Ligation in Streptavidin-Coated PCR Tubes
make a master solution and each tube contains 49 μl 1× ligation buffer
μl Taq DNA Ligase (40 U/_μl)
incubate at 60° C. for 60 min.
wash each tube 1× with 1× washing buffer
1× with ddH2O 7. Elution of Ligated Products
add 50 μl ddH2O to each tube and incubated at 95° C. for 5 min, chilled on ice, transfer the supernatant to a clean tube.

8. PCR Set Up

| 25 mM dNTPs | 0.5 μl |
|---|---|
| 10× buffer II (PEB) | 2.5 μl |
| 25 mM MgCl2 | 1.5 μl |
| AmpliTaq Gold DNA Polymerase (5 Units/μl, PEB) | 0.3 μl |
| Eluted (ligated) product (see above) | 3 μl |
| Primer set (T3/T7/T7v, 10 _M each) | 2 μl |
| ddH2O | 1 μl |
| Total volume | 25 μl |

PCR condition:
94° C. 10 min
35 cycles of 94° C. 30 sec
60° C. 30 sec
and then
72° C. 30 sec Example 2

Methylation Detection Assays

Plasmid DNA was used as an independent control DNA. The quality of methylation was tested by restriction digest of umnethylated and methylated DNA by methylation sensitive enzyme Hpa II and its isoschisomer Msp I, which is not sensitive to methylation. Bands were not detected on an agarose gel after digestion with methylated pUC19 with Hpa II for two hours at 37° C., while the unmethylated DNA was completely digested (data not shown).

A set of OLA primers targeted to 5 different Hpa II sites on the pBluescript KS+ plasmid were designed. Four out of these 5 sites are also present on pUC19. The specificity of these primers was tested in a model experiment using a standard genotyping protocol on the bead array. Methylated or unmethylated plasmid DNA was spiked into a human genomic DNA sample at approximately 1:1 molar ratio (1 pg of plasmid DNA to 1 ug of human genomic DNA). Samples were digested by restriction enzymes Dra I or Dra I in combination with methylation sensitive Hpa II. (FIG. 13a). This experiment confirmed that we could distinguish unmethylated and methylated control DNAs using restriction digestion. The primers did not crossreact with human genomic DNA and can be used in various combinations with other gene-specific primers (FIG. 13b).

Example 3

Whole Genome Amplification of Bi-Sulfite Converted Genomic DNA

Using standard DNA polymerase, this approach takes advantage of the unique sequence feature of genomic DNAs after bisulfite treatment, i.e. all the un-methylated cytosines are converted to uracil. Therefore, the DNA template for amplification will only contain three bases, A, G and T, and will be single-stranded, as opposed to the regular gDNA template.

Genomic amplification can be performed with a mixture of two sets of primers that contain all possible combinations of three nucleotides, in particular a first set having A, T and C, but not G; and a second set having A, T and G, but not C. Primers from the first set will have higher affinity to the original bisulfite converted DNA strand, while primers from the second set will preferentially anneal to the newly synthesized complementary strand. This approach avoids the presence of G and C in the same primer, thus preventing the primers to cross over any CpG sites to be interrogated, but nevertheless allows both strands to be amplified. In a variation of this gene amplification method, a poly-A primer is used for the first strand synthesis in combination with primers, containing combinations of A, T and G, but not C, for the complementary strand. This variation avoids the bias that may be introduced by the un-balanced annealing efficiency of primers corresponding to the two alleles (C or T).

Alternatively, the genomic amplification can be performed with primer sequences that contain only Adenines (As). The homopoly-A primers, for example, 6-mer, 9-mer, or longer, can be used for the first strand synthesis. After that, a homopoly-T tail can be added to the 3'-ends of the first strand products, using terminal deoxyribonucleotide transferase (TdT). A standard PCR is used to amplify the bisulfite converted genomic DNAs using a poly-A primers. It was estimated that the poly-T frequencies in the genome after bisulfite conversion are, on average, such that the physical distance between any two poly-(T)n sequences (n>=9) is 330 bp, which is a convenient amplicon size range.

Briefly, for the sodium bisulfite reaction, reagents should be fresh prepared before use.

To prepare 2 M NaOH 400 mg NaOH pellets are dissolved in 5 ml $H_2O$. A 2.5 M metabisulfite solution (corresponding to a free bisulfite concentration of 5M as follows: 1.9 g of sodium metabisulfite ($Na_2S_2O_4$, Sigma) are mixed with 2 ml sterile $H_2O$ and 0.7 ml 2M NaOH and the mixture is shaken for 10-15 minutes. Simultaneously, 350 mg of hydroquinone are mixed with 1 ml sterile $H_2O$ to yield a saturated solution. Subsequently, 500 ul of hydroquinone solution are added to the bisulfite solution and shaking of the mixture is continued. The pH is checked using indicator paper and adjusted, if necessary, to pH 5.0 with 2M NaOH. The final volume is adjusted to 4 ml using sterile $H_2O$ (~200 ul).

Samples of 100 ul final volume, 3 M Bisulfite are prepared by starting with a 36 ul sample (~1 ug GDNA) and 4 ul 2N NaOH, incubating for 10 min at 37° C. and adding 60 ul 5M Bisulfite solution. The samples are subjected to thermocycling under the following conditions:

One cycle at 95° C. 90 sec, 50° C. for 1 hour; four cyles at 95° C. for 45 sec followed by 50° C. for 4 hours. The samples are then stored at 4° C.

To finish the bisulfite modifications a MultiScreen-PCR clean-up plate is used to clean the reactions from Bisulfite. The samples are transferred into the plate wells; and unused wells are covered with adhesive seal. The plates are placed on top of the MultiScreen manifold and a vacuum (manometer reads 15) is applied for 10 min or until wells have emptied. The filters appear shiny even after they are dry. The reaction mixtures are washed with 100 ul of dd$H_2O$, followed by addition of 50 ul of water to each well and vigorous mixing of the samples on a plate shaker (1750 rpm) for 5 minutes. The eluted DNA is transferred from each well into an Eppendorf tube followed by addition of 50 ul of 0.4 M NaOH to a final concentration of 0.2 M. The eluted DNA is incubated at RT for 20 min to desulfonate the pyrimidines followed by addition of ½ volume (50 ul) of 7.5 M ammonium acetate and 2.5 vol (375 ul) of 100% Ethanol. After centrifugation for 10 min at 12000 g, the pellets are washed with 70% EtOH, air-dried, and resuspended in 20 ul TE for biotinylation.

Example 4

Genome-Wide Calibration of Genomic DNA Methylation Measurement

For any given organism, a reference genomic DNA is amplified many fold, for example, 100 fold, 1000 fold or more. Any whole genome amplification method desired by the user can be utilized, for example, random hexamers, 9-mers, 11-mers, 13-mers or 15-mers, primed DNA amplification by enzymes including, but are not limited to, the Klenow fragment of DNA polymerase I, SEQUENASE 1.0 and SEQUENASE 2.0 (U.S. Biochemical), T5 DNA polymerase and Phi29 DNA polymerase or any other DNA polymerase, or Rubicon Genomics' OmniPlex technology. After this amplification, all the endogenous DNA methylations are diluted 100-fold, 1000-fold or more. The amplified genomic DNA serves as a fully "un-methylated" template. The amplified genomic DNA or the original un-amplified genomic DNA, or both are subsequently methylated in vitro, and then serve as a fully "methylated" template.

The fully un-methylated and methylated genomic DNA templates can be mixed at different ratios, for example, 0%, 10%, 20%, 30%, 40%, 50%, 60%, 70%, 80%, 90% and, 100% of methylated template, to constitute a gradient of methylated template concentration. Methylation assays performed on these mixed templates will allow for generation of a calibration curve for the quantitative methylation measurement in unknown samples. The mixed templates can also be used to determine the Limit of Detection (LOD) for any methylation detection method, in particular what percentage of the methylated template can be detected in the presence of un-methylated template.

This approach can also be used to evaluate the integrity of a methylation assay across the entire genome and thus facilitate the development of further methylation assays. For example, if an assay results in identical methylation measurements for both the un-methylated and the methylated templates, the integrity of the assay has been compromised.

Example 5

Genomic Amplification by Sodium Bisulfite Reaction

Briefly, for the sodium bisulfite reaction, reagents should be fresh prepared before use.

To prepare 2 M NaOH, 400 mg NaOH pellets are dissolved in 5 ml H2O. Subsequently, prepare a 2.5 M metabisulfite solution corresponding to a free bisulfite concentration of 5M as follows by mixing 1.9 g of sodium metabisulfite ($Na_2S_2O_4$, Sigina) with 2 ml sterile $H_2O$ and 0.7 ml 2M NaOH. The miture is shaken for 10-15 minutes. Simultaneously, 350 mg of hydroquinone are mixed with 1 ml sterile $H_2O$ to achieve a saturated solution. Then, 500 ul of hydroquinone solution are added to the bisulfite solution and shaking is continued. The pH is checked using indicator paper and adjusted, if necessary, to pH 5.0 with 2M NaOH. The final volume is adjusted to 4 ml using sterile H2O (~200 ul).

Samples of 100 ul final volume, 3 M Bisulfite are prepared by starting with a 36 ul sample (~1 ug gDNA) and 4 ul 2N NaOH, incubating for 10 min at 37° C. and adding 60 ul 5M Bisulfite solution. The samples are subjected to thermocycling under the following conditions:

One cycle at 95° C. 60 sec, 50° C. for 1 hour; four cycles at 95° C. each for 20 sec followed by 50° C. for 4 hours. The samples are then stored at 4° C.

To finish the bisulfite modifications a Micro-PCR clean-up plate and in-plate desulfonation are used to clean the reactions from Bisulfite. The samples are transferred into the plate wells; and unused wells are covered with adhesive seal. The plates are placed on top of the Millipore manifold and a vacuum (manometer reads 20) is applied for 8 minutes or until wells have emptied. The filters appear shiny even after they are dry. The reaction mixtures are washed with 100 ul of dd$H_2O$ for 5 to 6 minutes. Subsequently, 20 ul of 0.1 N NaOH are added to each well and the samples are mixed vigorously on a plate shaker (1750 rpm) for 10 minutes, followed by addition of 10 ul of 7.5 M ammonium acetate to neutralize samples in the plate.

A vacuum is applied for 6-8 min or until wells have emptied. The samples are subsequently washed with 100 ul of 10 mM Tris-HCl pH 8.0 and eluted in 20 ul TE-buffer on the shaker, followed by recovery of the eluted DNA.

All references are expressly incorporated herein by reference.

What is claimed is:

1. A method for multiplex detection of methylation in a population of double-stranded target nucleic acids comprising:
(a) providing a population of double-stranded target nucleic acids labeled with a purification tag, wherein said target nucleic acids comprise potentially methylated target sequences;
(b) cleaving said population of target nucleic acids with an enzyme, whereby said enzyme selectively cleaves at unmethylated target sequences in said population of target nucleic acids and does not cleave at methylated target sequences in said population of target nucleic acids, forming a population of cleaved target nucleic acids labeled with a purification tag and a population of non-cleaved target nucleic acids labeled with a purification tag;
(c) immobilizing said population of non-cleaved said target nucleic acids by said purification tag, thereby forming immobilized non-cleaved target nucleic acids; and
(d) detecting the presence of said immobilized non-cleaved target nucleic acids wherein said detecting step comprises:
contacting said immobilized non-cleaved target nucleic acids with a composition comprising a plurality of different target probes, each of said probes comprising:
a first region complementary to a first region of one of said immobilized non-cleaved target nucleic acids and a second region comprising a detection sequence complementary to one of said potentially methylated target sequences,
whereby selectively forming a plurality of different hybridization complexes between said immobilized non-cleaved target nucleic acids and said different target probes indicates the presence of methylation in said population of double-stranded target nucleic acids.

2. The method according to claim 1, wherein said purification tag comprises biotin.

3. The method according to claim 1, wherein said enzyme is HpaII.

4. A method for multiplex detection of methylation in a population of double-stranded target nucleic acids comprising:
(a) providing a population of double-stranded target nucleic acids labeled with a purification tag, wherein said target nucleic acids comprise potentially methylated target sequences;
(b) cleaving said population of target nucleic acids with an enzyme, whereby said enzyme selectively cleaves at unmethylated target sequences in said population of target nucleic acids and does not cleave at methylated target sequences in said population of target nucleic acids, forming a population of cleaved target nucleic acids labeled with a purification tag and a population of non-cleaved target nucleic acids labeled with a purification tag;
(c) immobilizing said population of non-cleaved said target nucleic acids by said purification tag, thereby forming immobilized non-cleaved target nucleic acids; and
(d) detecting the presence of said immobilized non-cleaved target nucleic acids, wherein said detecting step comprises:
(i) contacting said immobilized non-cleaved target nucleic acids with a composition comprising a plurality of different target probes and selectively forming a plurality of different hybridization complexes between said immobilized non-cleaved target nucleic acids and said different target probes, each of said probes comprising: a region complementary to a region of one of the non-cleaved target nucleic acid and at least a universal priming sequence;
(ii) amplifying said different hybridization complexes in the presence of a composition comprising:
a) at least first universal primers complementary to said universal priming sequence;
b) dNTPs; and
c) a polymerase,
thereby forming a plurality of different amplicons, whereby
detecting said plurality of different amplicons is an indication of the presence of methylation in said population of double-stranded target nucleic acids.

5. The method according to claim 4, wherein said purification tag comprises biotin.

6. The method according to claim 4, wherein said enzyme is HpaII.

* * * * *